United States Patent
Sahay et al.

(10) Patent No.: US 12,098,170 B2
(45) Date of Patent: Sep. 24, 2024

(54) SURFACE LAYER PROTEIN A (SlpA) AS A THERAPEUTIC AGENT FOR THE TREATMENT OF INFLAMMATORY DISEASES

(71) Applicants: UNIVERSITY OF FLORIDA RESEARCH FOUNDATION, INCORPORATED, Gainesville, FL (US); RISE THERAPEUTICS, LLC, Rockville, MD (US)

(72) Inventors: Bikash Sahay, Gainesville, FL (US); Gary Fanger, Rockville, MD (US); Jyoti Jha, Clarksburg, MD (US); Christian Furlan Freguia, Germantown, MD (US)

(73) Assignees: UNIVERSITY OF FLORIDA RESEARCH FOUNDATION, INCORPORATED, Gainesville, FL (US); RISE THERAPEUTICS, LLC, Rockville, MD (US)

( * ) Notice: Subject to any disclaimer, the term of this patent is extended or adjusted under 35 U.S.C. 154(b) by 0 days.

(21) Appl. No.: 18/568,888

(22) PCT Filed: Jun. 10, 2022

(86) PCT No.: PCT/US2022/032938
§ 371 (c)(1),
(2) Date: Dec. 11, 2023

(87) PCT Pub. No.: WO2022/261393
PCT Pub. Date: Dec. 15, 2022

(65) Prior Publication Data
US 2024/0262873 A1    Aug. 8, 2024

Related U.S. Application Data

(60) Provisional application No. 63/209,426, filed on Jun. 11, 2021.

(51) Int. Cl.
*C07K 14/335* (2006.01)
*A61K 38/16* (2006.01)
*A61K 45/06* (2006.01)

(52) U.S. Cl.
CPC .......... *C07K 14/335* (2013.01); *A61K 38/164* (2013.01); *A61K 45/06* (2013.01)

(58) Field of Classification Search
CPC ..... C07K 14/335; A61K 45/06; A61K 38/164
See application file for complete search history.

(56) References Cited

U.S. PATENT DOCUMENTS

| | | | |
|---|---|---|---|
| 10,562,943 B2 | 2/2020 | Lightfoot et al. | |
| 11,028,135 B2 | 6/2021 | Lightfoot et al. | |
| 11,098,088 B2 | 8/2021 | Lightfoot et al. | |
| 2005/0112612 A1* | 5/2005 | Klaenhammer | A23C 19/0323 435/320.1 |
| 2011/0039765 A1 | 2/2011 | Connor | |
| 2020/0207814 A1 | 7/2020 | Lightfoot et al. | |
| 2021/0300973 A1 | 9/2021 | Lightfoot et al. | |

FOREIGN PATENT DOCUMENTS

WO    WO 2004/096992    11/2004

OTHER PUBLICATIONS

Seq Id No. 60 in US 20050112612 A1, from http://score.uspto.gov/ScoreAccessWeb/viewSeqIdResult?docId=b58a5371-8245-4305-8262-580986af784e&appId=10831070&maxSeqCount=308&versionNo=1.1&seqNums=60, accessed May 17, 2024, pp. 1-2.*
Written Opinion in International Application No. PCT/US2022/032938, Nov. 2, 2022, pp. 1-6.

* cited by examiner

*Primary Examiner* — Li N Komatsu
(74) *Attorney, Agent, or Firm* — SALIWANCHIK, LLOYD & EISENSCHENK

(57) ABSTRACT

The current invention provides a recombinant bacterium, the recombinant bacterium being genetically modified to synthesize surface layer protein A (SlpA). Efficacious therapies for a subject suffering from an inflammation mediated disease are also provided. The methods of the current invention comprise administering to a subject in need thereof a therapeutically effective amount of the recombinant bacterium, for example *L. lactis* cells, or a therapeutically effective amount of the isolated SlpA. The recombinant bacteria cells or SlpA isolated from the recombinant bacteria can be in a pharmaceutical composition comprising a pharmaceutically acceptable carrier and/or excipient.

12 Claims, 30 Drawing Sheets
Specification includes a Sequence Listing.

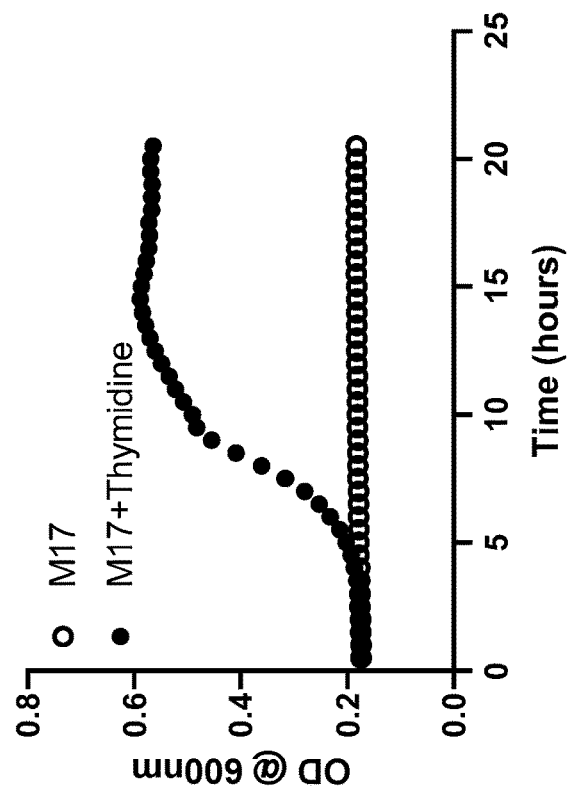
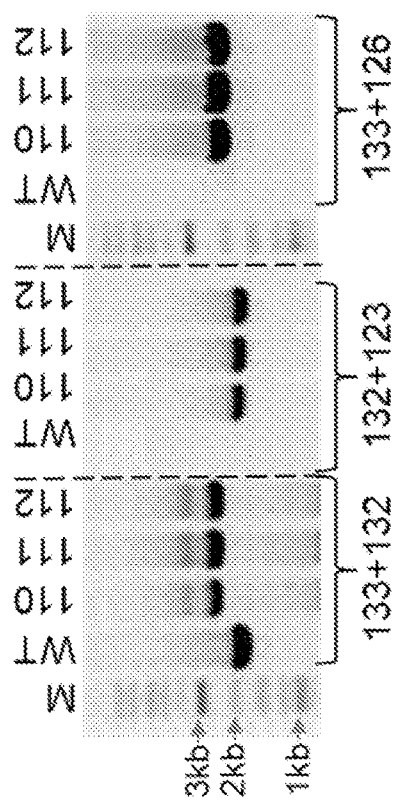
FIG. 1A
FIG. 1B

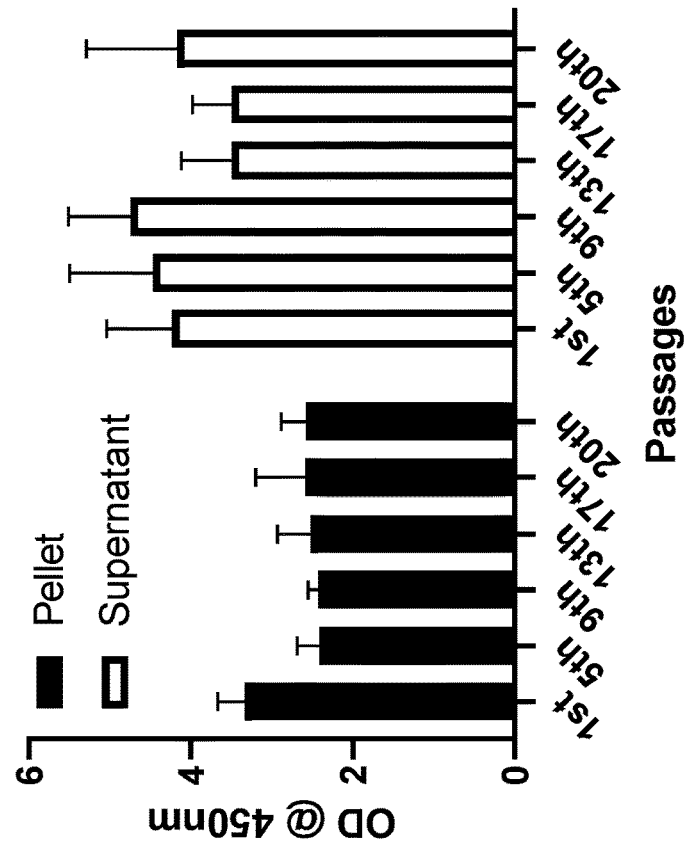
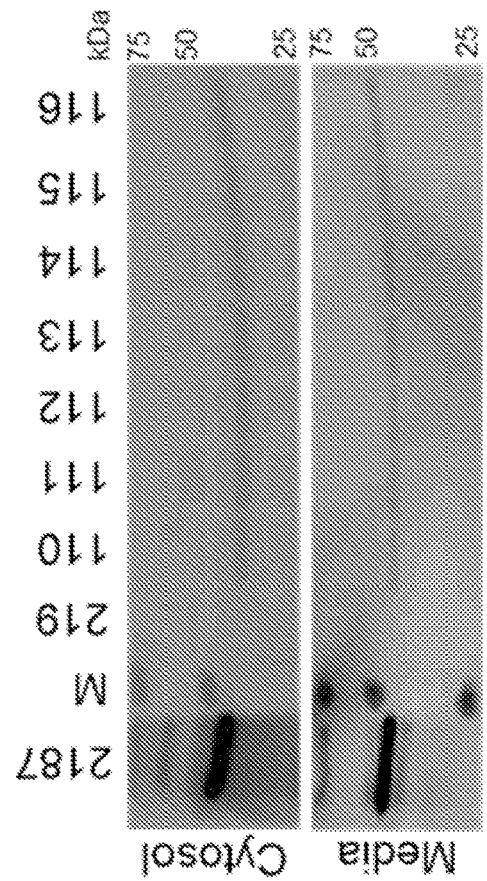
FIG. 1C
FIG. 1D

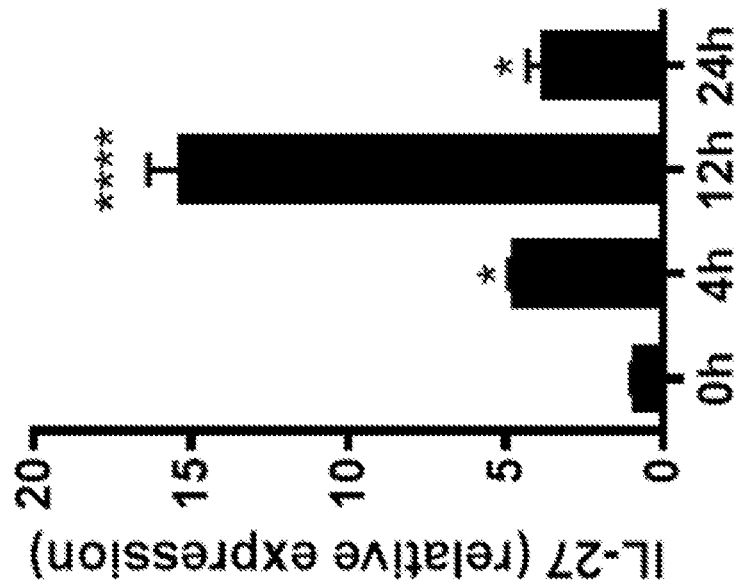
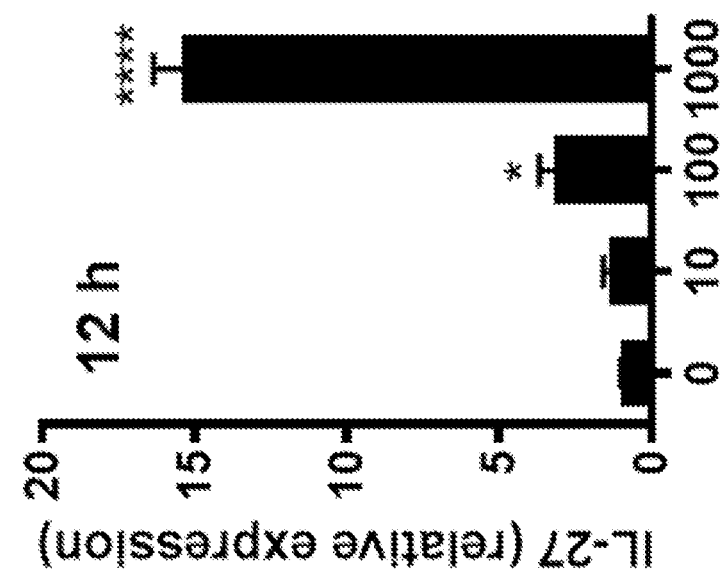
FIG. 9A
FIG. 9B

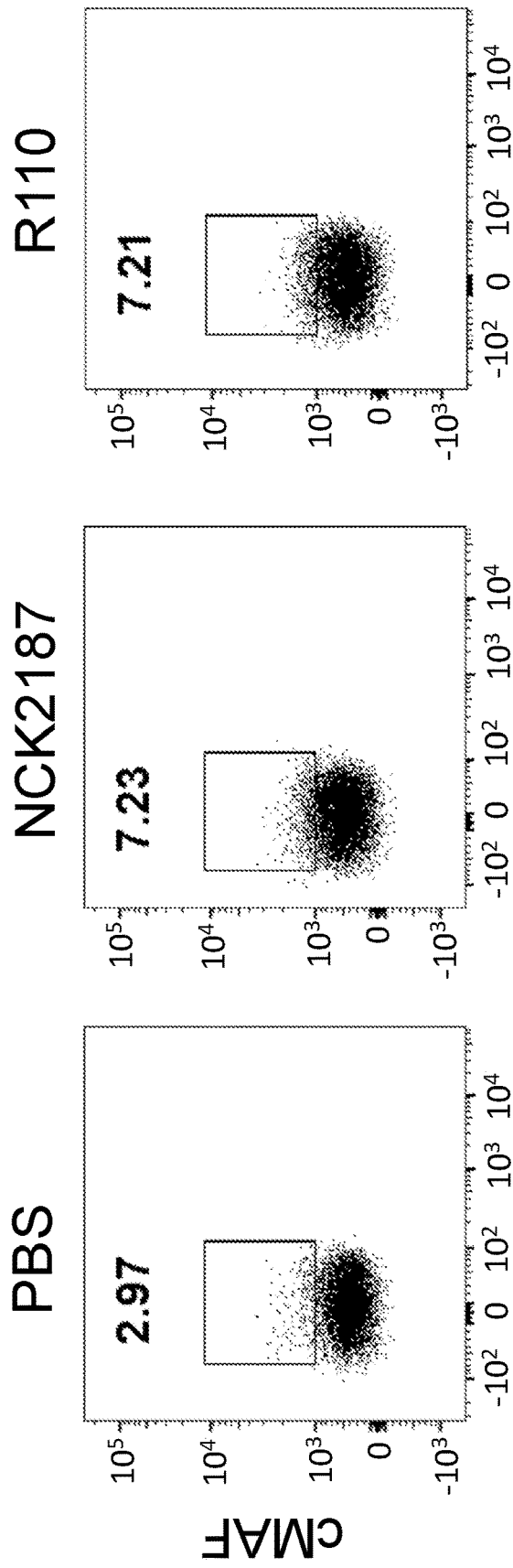
FIG. 10C
FIG. 10D
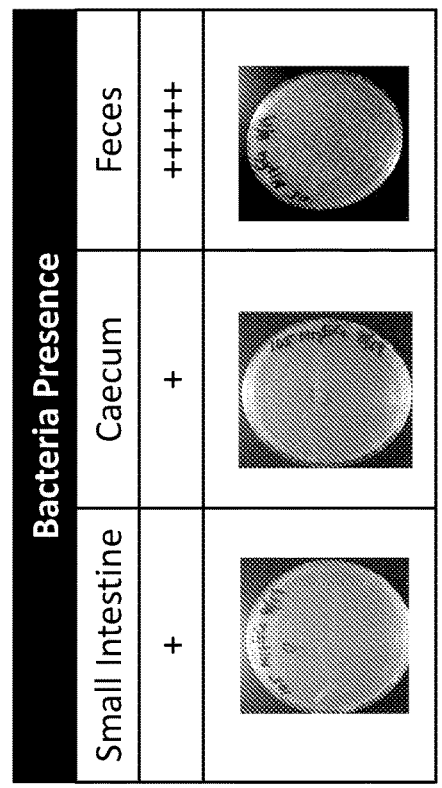
FIG. 11

SURFACE LAYER PROTEIN A (SlpA) AS A THERAPEUTIC AGENT FOR THE TREATMENT OF INFLAMMATORY DISEASES

CROSS-REFERENCE TO RELATED APPLICATIONS

This application is the U.S. National Stage Application of International Patent Application No. PCT/US2022/032938, filed on Jun. 10, 2022, which claims the benefit of U.S. Provisional Application Ser. No. 63/209,426, filed Jun. 11, 2021, the disclosure of which is hereby incorporated by reference in its entirety, including all figures, tables and amino acid or nucleic acid sequences.

GOVERNMENT SUPPORT

This invention was made with government support under DK117726 awarded by The National Institutes of Health. The government has certain rights in the invention.

STATEMENT REGARDING SEQUENCE LISTING

The Sequence Listing for this application is labeled "Seq-List.txt" which was created on Jun. 9, 2022 and is 43 KB. The entire content of the sequence listing is incorporated herein by reference in its entirety.

BACKGROUND OF THE INVENTION

Inflammatory bowel disease (IBD) is a chronic intestinal ailment affecting 6.8 million individuals globally [1]. In the US, 77 children and 478 adults per 100,000 are affected by the disease [2]. Typically, IBD is characterized into two major groups: Crohn's disease (CD) and ulcerative colitis (UC). In UC, the intestinal inflammation is typically superficial, involving only the mucosal layer, confined to the colon. In CD, the inflammation is transmural, extending through the intestinal wall to the serosal layer, affecting the entire gastrointestinal (GI) tract. The distal ileum and ascending colon are the most common sites of involvement. While the significant area of pathology and the most responsible for the patients' symptoms is the GI tract, inflammatory mediators can also leak into the systemic circulation and affect other organs, such as the musculoskeletal system [3-6], and their disease progression is linked to the gut pathology. The systemic inflammation ameliorates with improvement of GI health [7,8]. Treatment of IBD includes untargeted therapies (e.g., amino-salicylates, glucocorticoids) and targeted biologics (e.g., anti-tumor necrosis factor antibodies), signaling inhibitors (e.g., Janus Kinase inhibitors), or lymphocyte trafficking modulators (e.g., anti-α4β7 integrin antibodies). Unfortunately, none of these therapies are effective in all the patients, and biological therapies often fail over time due to immunogenicity, providing an opportunity to develop a new IBD treatment.

Gut microbiota plays a critical role in the homeostatic maintenance of health. Commensal bacteria function to maintain integrity of the intestinal epithelial barrier, as well as regulate innate and adaptive immune cell function [9]. Perturbation of the gut microbiome is associated with several diseases, including IBD. IBD patients' gut microbiome is characterized by dysbiosis and leaky gut [10]; hence, there is an opportunity to leverage the gut microbiota as a treatment for IBD. Several attempts have been made to overhaul the microbial components using fecal microbial transfer (FMT) treatment, which provided good protective responses in few cases; however, safety is an issue as there is always a chance to introduce antibiotic-resistant bacteria or other unwanted microbes in the recipients [11, 12]. As an alternative to FMT, several groups have proposed using a consortium of selected bacterial species to reduce gastrointestinal inflammation. Single bacterial species were also tested in colitis management. Overall, all these strategies have not yielded consistently positive results [13]. A promising and potentially safer approach to the treatment of IBD is to leverage the body's own natural immune regulatory mechanisms that reside in the interactions between commensal microbial products with host immune cells lining the gut epithelial layer.

BRIEF SUMMARY OF THE INVENTION

The current invention provides a recombinant bacterium, for example, a recombinant *Lactococcus* (*L.*) *lactis*, that is genetically modified to express surface layer protein A (SlpA). A better strategy to deliver SlpA orally can be to engineer a food-grade, safe probiotic, such as *L. lactis* for the expression of SlpA. The slpA gene can be inserted into the thymidylate synthase (thyA) gene, thus providing a containment strategy such that the organism will not grow after being excreted from the body. Additionally, the SlpA can be made a secretory protein to increase its interaction with immune cells.

The current invention also provides an efficacious therapy for a subject suffering from an inflammation mediated disease (inflammatory diseases), for example, an autoinflammatory disease, such as IBD or other inflammatory diseases, such as allergies, ankylosing spondylitis, Crohn's disease, diabetes, Type I diabetes, gastroesophageal reflux disease, Hashimoto's thyroiditis, hyperthyroidism, hypothyroidism, interstitial cystitis (IC), Lofgren's syndrome, lupus erythematosis, myasthenia gravis, multiple sclerosis, osteoarthritis, polymyalgia rheumatica, prostatitis, psoriasis, psoriatic arthritis, Raynaud's syndrome/phenomenon, reactive arthritis (Reiter syndrome), restless leg syndrome, reflex sympathetic dystrophy (RSD), rheumatoid arthritis, scleroderma, Sjögren's syndrome, ulcerative colitis, uveitis, acute respiratory distress syndrome (ARDS), asthma, bronchiectasis, bronchiolitis obliterans, bronchitis, chronic bronchitis, COPD, Coccidioidomycosis, Coronaviruses, COVID-19, eosinophilic granulomatosis, hypersensitivity pneumonitis, influenza, interstitial lung disease, pneumonia, MERS, pulmonary artery hypertension, RSV, sarcoidosis, and SARS. The methods of the current invention comprise administering to a subject in need thereof a therapeutically effective amount of recombinant bacteria, such as *L. lactis* cells, or a therapeutically effective amount of purified surface layer protein A (SlpA), for example, SlpA isolated from *L. lactis*. In one embodiment, the *L. lactis* cells are *L. lactis* strain R110 which is a bacterium genetically modified to express SlpA.

The recombinant bacterial cells (e.g., *L. lactis* cells) or SlpA isolated from *L. lactis* can be formulated into a pharmaceutical composition comprising a pharmaceutically acceptable carrier and/or excipient (optionally in combination with other therapeutic agents). In an embodiment of the invention, the pharmaceutical composition is administered orally. SlpA-expressing bacteria can lead to an enrichment of beneficial bacteria in the gut and can reduce pro-inflammatory mediators, increase expression of anti-inflammatory mediators, can restore the gut barrier and a more normal microbiome makeup, and overall balance the host immune response.

BRIEF DESCRIPTION OF THE DRAWINGS

FIGS. 1A-1D: Generation of a SlpA-expression bacterial strain. (FIG. 1A) PCR primers used to screen for SlpA+ and Thy– colonies. The primers used were 132 (5'-GACCGCCTTTCCGTTATTATCC-3', SEQ ID NO: 1) and 133 (5'-TGGGGCGGAAGTGGAAATACTTATGG-3', SEQ ID NO: 2), which amplify both the WT (~2 Kb band) and the SlpA (~2.6 Kb band) colonies; 132 and 123 (5'-GCATGCTCGAGTCTAGAAGTCTTATAACTATAC-3', SEQ ID NO: 3), which is specific for the SlpA cells; and 133 and 126 (5'-GTCGACCGGTTTATCGAAAATTAGC-TACTTTTAC-3', SEQ ID NO: 4), which is specific for the SlpA cells. Representative results of PCR for three different clones, 110, 111, and 112. (FIG. 1B) Representative growth curve of clone 110 in M17 media with and without thymidine supplementation. Bacteria were incubated with the proper medium in a 96 well plate, and growth was measured by OD660$_{nm}$ overnight. (FIG. 1C) Stability of the SlpA cassette was demonstrated by culturing the bacteria for 20 generations. Expression of SlpA was detected in the cell pellet and supernatants from passages 1, 5, 9, 13, 17, and 20 by ELISA; the experiment was run in triplicate; mean+SD. (FIG. 1D) Western blot demonstrating that SlpA is secreted from the R110 bacteria.

(FIG. 3A) Each mouse was weighed every 20 week, and the weight changes were depicted using the weight at the initiation of the experiment as 100 percent. (FIG. 3D) Mice were fed with FITC-dextran, and four hours later serum from euthanized mice was tested for FITC fluorescence. The data is compared with the C57BL/6 mice without colitis (open bar). (FIG. 3E) Serum albumin was measured in the fecal material at the end of the experiment. (FIG. 3F) Feces were collected every week to evaluate the fecal occult blood in the feces using a commercial kit. (FIG. 3B) Colon lengths were measured at the end of the experiment. (FIG. 3C) The colon of mice was stained with hematoxylin and eosin stain to observe the structure and infiltrating cells. Data represent three individual experiments and are shown as mean±SEM. n=5 mice/group. *$P<0.05$, @$P<0.01$, #$P<0.001$, $$P<0.0001$.

FIG. 5A), IL-10 (FIG. 5B), and IL-17 (FIG. 5C) from Rag1-deficient mice after 8 weeks post initiation. Data are shown as mean SEM and are representative of three different experiments. *$P<0.05$, #$P<0.001$, $$P<0.0001$.

(FIG. 7A) Phylum-wise genera were clustered to show the differential accumulation of bacterial genera in the different treatment groups. (FIG. 7B) Linear discriminant analysis (LDA) shows the genus and species of the bacteria that are differentially present between the mice fed with R110 or PBS. (FIG. 7C) LDA to show the genus and species of the differentially present bacteria between the mice fed with R110 or NCK2187.

(FIG. 8A) A Venn diagram shows the numbers of differentially expressed genes in different situations. Heat maps showing the differential expression of important (FIG. 8B) cell surface receptors (left two columns, R110; center two columns, unstimulated; right two columns, wild type *L. lactis*), (FIG. 8C) cytokines and chemokines (left two columns, R110; center two columns, wild type *L. lactis*; right two columns, unstimulated), (FIG. 8D) immunomodulating enzymes (left two columns, unstimulated; center two columns, R110; right two columns, wild type *L. lactis*), and (FIG. 8E) interferon-related genes in response to SlpA expressing *L. lactis* (left two columns, R110; center two columns, unstimulated; right two columns, wild type *L. lactis*).

FIGS. 9A-9B: SlpA leads to increase expression of IL-27 and cMAF in murine DC. Murine bone marrow cells differentiated into dendritic cells using GMCSF. (FIG. 9A) Murine dendritic cells were incubated with increasing concentration of SlpA (0, 10, 100, and 1000 ng/ml) for 12 h. (FIG. 9B) Murine dendritic cells were exposed to 1000 ng/ml for 4, 12, and 24 hours. Total RNA was isolated and converted to cDNA for using them as a template for evaluation of IL-27 transcript. GAPDH was used as endogenous control. *P<0.05, ****P<0.0001.

FIGS. 10A-10D. Rag1$^{-/-}$ mice were introduced with the 10$^6$ naive CD4 T cells for induction of colitis. Mice were gavaged with R110 and NCK2187 every week for a month. Colonic dendritic cells (CD45$^+$CD11c$^+$MHC$^{Hi}$) were analyzed for IL-27 production; (FIG. 10A) histogram and (FIG. 10B) geometric mean of the fluorescence for the phycoerythrin (PE) channel representing IL-27. Colonic CD4 T cells stained for cMAF; (FIG. 10C) dot plots and (FIG. 10D) bar diagram showing the percentage of CD4 T cells expressing cMAF. *P<0.05.

FIG. 11: Mice were gavaged with SlpA expressing *L. lactis* resistant to erythromycin at dose of 10$^9$ CFU; 24 h later, mice were euthanized to collect contents from the small intestine, caecum, and feces. Intestinal contents and feces were dissolved with sterile PBS (100 mg/ml) and plated 100 μl of the contents on M17-erythromycin plates (5 μg/ml). The plates were incubated at 30° C. for 48 h, and then the plates were photographed.

(FIG. 13A) The data showed all the unique genes differentially expressed in DC exposed to R110 (left two columns, R110; center two columns, Wild type *L. lactis*; right two columns, unstimulated). (FIG. 13B) The data show all the six genes that are differentially expressed in DC exposed to WT *lactis* (left two columns, unstimulated; center two columns, wild type *L. lactis*; right two columns, R110). A selection threshold of P-value ≤0.05 and log 2-fold change ≥1 was used for analysis. Duplicate samples were used for each condition.

FIG. 16A) FoxP3-eGFP mice were orally administered with R110 or WT *L. lactis* before LPS administration. Treg were measured in homogenized lung tissue by flow cytometry. FIGS. 16B-16C) Lung injury was triggered as above in C57Bl/6, Rag1$^{-/-}$ mice, or IL27$^{-/-}$ mice. Lung neutrophils were measured by flow cytometry. *p<0.05.

BRIEF DESCRIPTION OF THE SEQUENCES

Figures 2A, 2B, 2C:
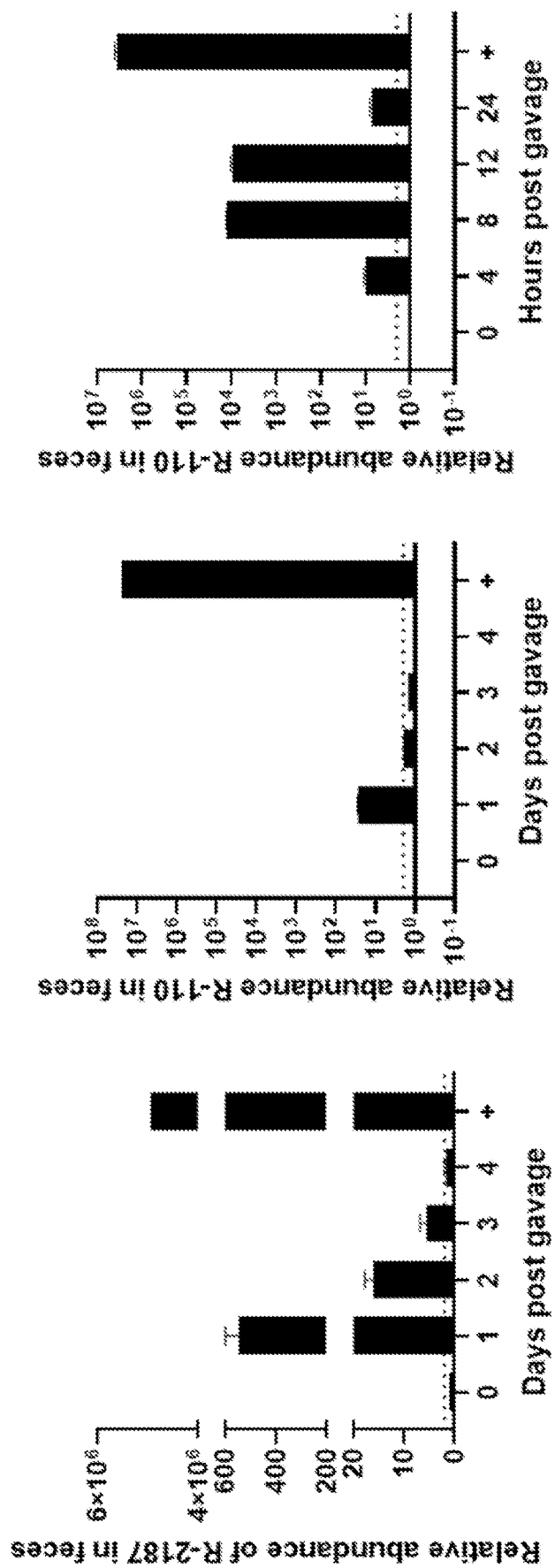
FIGS. 2A-2C: Intestinal availability of SlpA-expressing bacteria. Mice were fed with $10^9$ CFU of *Lactobacillus acidophilus* NCFM with SlpA expressed on its surface (NCK2187) or R110, and feces were collected every day (FIG. 2A, FIG. 2B) or at 4, 8, 12, and 24 hours post gavage (FIG. 2C). Total DNA was isolated, and the presence was detected using primers specific for SlpA in NCK2187 or R110. The presence of eubacteria was used as an internal control against which the presence of NCK2187 and R110 was calculated using the formula: $2^{\wedge-\Delta cT}$. n=3.

SEQ ID NO: 1: Oligonucleotide primer 132.
SEQ ID NO: 2: Oligonucleotide primer 133.
SEQ ID NO: 3: Oligonucleotide primer 123.
SEQ ID NO: 4: Oligonucleotide primer 126.
SEQ ID NO: 5: Recombinant SlpA amino acid sequence.
SEQ ID NO: 6: Recombinant slpA nucleotide sequence.
SEQ ID NO: 7: SlpA Uniprot Access Number C2HR60.
SEQ ID NO: 8: SlpA Uniprot Access Number P35829.
SEQ ID NO: 9: SlpA Uniprot Access Number G1UE81.
SEQ ID NO: 10: SlpA Uniprot Access Number Q9Z4J9.
SEQ ID NO: 11: SlpA Uniprot Access Number H6VTN4.
SEQ ID NO: 12: SlpA Uniprot Access Number Q09FM2.
SEQ ID NO: 13: SlpA Uniprot Access Number L7YE91.
SEQ ID NO: 14: SlpA Uniprot Access Number K8DVK7.
SEQ ID NO: 15: SlpA Uniprot Access Number F0NUB7.
SEQ ID NO: 16: Signal Peptide of Recombinant SlpA of SEQ ID NO: 5.
SEQ ID NO: 17: Mature Protein of Recombinant SlpA of SEQ ID NO. 5.
SEQ ID NO: 18: Forward primer amplifying SlpA gene of *L. lactis* R110.
SEQ ID NO: 19: Reverse primer amplifying SlpA gene of *L. lactis* R110.
SEQ ID NO: 20: Forward primer amplifying SlpA gene of *Lactobacillus acidophilus* NCK2187.
SEQ ID NO: 21: Reverse primer amplifying SlpA gene of *Lactobacillus acidophilus* NCK2187.

DETAILED DISCLOSURE OF THE INVENTION

The current invention provides SlpA as an effector molecule expressed by bacteria, for example, *L. lactis* and its in vivo protective role in inflammation mediated diseases (inflammatory diseases), for example, inflammation mediated diseases of the gastrointestinal tract or lung such as IBD or other inflammatory diseases, such as allergies, ankylosing spondylitis, Crohn's disease, diabetes, Type I diabetes, gastroesophageal reflux disease, Hashimoto's thyroiditis, hyperthyroidism, hypothyroidism, Irritable Bowel Syndrome (IBS), interstitial cystitis (IC), Lofgren's syndrome, lupus erythematosis, myasthenia gravis, multiple sclerosis, osteoarthritis, polymyalgia rheumatica, prostatitis, psoriasis, psoriatic arthritis, Raynaud's syndrome/phenomenon, reactive arthritis (Reiter syndrome), restless leg syndrome, reflex sympathetic dystrophy (RSD), rheumatoid arthritis, scleroderma, Sjögren's syndrome, ulcerative colitis, acute respiratory distress syndrome (ARDS), asthma, bronchiectasis, bronchiolitis obliterans, bronchitis, chronic bronchitis, COPD, Coccidioidomycosis, Coronaviruses, COVID-19, eosinophilic granulomatosis, hypersensitivity pneumonitis, influenza, interstitial lung disease, pneumonia, MERS, pulmonary artery hypertension, RSV, sarcoidosis, SARS, lung inflammatory disease, bacterial pneumonia, viral pneumonia, and uveitis.

A bacterium, for example, a lactic acid bacterium, can be genetically modified to express SlpA or orthologs of SlpA (i.e., protein homologs that are present within different species and have very similar or identical function) and used in the methods disclosed herein. Such bacteria can be referred to as "recombinant bacteria".

The genetic modifications resulting in increased expression or initiated synthesis of polypeptides include, but are not limited to, adding the entire coding region of the gene or a portion of the coding nucleotide sequence, introducing a frame shift mutation, a missense mutation, a substitution, an insertion, or by combinations of any of the aforementioned mutations. Additional mutations which would lead to increased or initiated expression of a polypeptide of interest and methods of introducing such mutations into a bacterium are well known to a person of ordinary skill in the art and such embodiments are within the purview of the claimed invention.

In a certain embodiment, the recombinant bacterium is a lactic acid bacterium, such as a *Lactococcus* bacterium or a *Lactobacillus* bacterium. These bacterial cells may also be referred to as probiotic bacterial cells. Non-limiting examples of such lactic acid bacteria include, but are not limited to, *Lactococcus chungangensis, Lactococcus formosensis, Lactococcus fujiensis, Lactococcus hircilactis, Lactococcus garvieae* (including, for example, *Lactococcus garvieae* subsp. *garvieae* and *Lactococcus garvieae* subsp. *bovis*), *Lactococcus lactis* (including, for example, *Lactococcus lactis* subsp. *cremoris, Lactococcus lactis* subsp. *hordniae, Lactococcus lactis* subsp. *lactis*, and *Lactococcus lactis* subsp. *tructae*), *Lactococcus laudensis, Lactococcus nasutitermitis, Lactococcus piscium, Lactococcus plantarum, Lactococcus raffinolactis,* and *Lactococcus taiwanensis.* In certain other embodiments, the lactic acid bacterium is a *Lactobacillus.* These bacterial cells may also be referred to as probiotic bacterial cells. Non-limiting examples of such lactic acid bacteria include, but are not limited to, *Lactobacillus acidophilus, Lactobacillus amylolyticus, Lactobacillus amylovorus, Lactobacillus brevis* (including, for example, *Lactobacillus brevis* ssp. *gravesensisi*), *Lactobacillus buchneri, Lactobacillus crispatus, Lactobacillus gallinarum, Lactobacillus gigeriorum, Lactobacillus helveticus suntoryeus, Lactobacillus hilgardii, Lactobacillus kefiranofaciens, Lactobacillus pasteurii, Lactobacillus plantarum,* and *Lactobacillus ultunensis.*

An embodiment provides a composition comprising the recombinant bacterium of the current invention and a pharmaceutically acceptable carrier and/or excipient.

The bacteria of the current invention provide protective role in inflammation mediated diseases, for example, inflammation mediated diseases of gastrointestinal tract, such as IBD. Accordingly, certain embodiments of the current invention provide methods of treating and/or preventing an inflammation mediated disease of the gastrointestinal system in a subject, the method comprising, administering to the subject a therapeutically effective amount of the bacterium of the current invention. In other embodiments, this invention deals with methods to treat systemic inflammatory diseases, such as lung inflammation. In one embodiment, the bacterium is orally administered to the subject.

As used herein, the term "nucleic acid" or "polynucleotide" refers to deoxyribonucleic acids (DNA) or ribonucleic acids (RNA) and polymers thereof in either single- or double-stranded form. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, single nucleotide polymorphisms (SNPs), and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)). The term nucleic acid is used interchangeably with gene, cDNA, and mRNA encoded by a gene.

As used herein, the term "isolated nucleic acid" molecule refers to a nucleic acid molecule that is separated from other nucleic acid molecules that are usually associated with the isolated nucleic acid molecule. Thus, an "isolated nucleic acid molecule" includes, without limitation, a nucleic acid molecule that is free of nucleotide sequences that naturally flank one or both ends of the nucleic acid in the genome of the organism from which the isolated nucleic acid is derived (e.g., a cDNA or genomic DNA fragment produced by PCR or restriction endonuclease digestion). Such an isolated nucleic acid molecule is generally introduced into a vector (e.g., a cloning vector or an expression vector) for convenience of manipulation or to generate a fusion nucleic acid molecule. In addition, an isolated nucleic acid molecule can include an engineered nucleic acid molecule such as a recombinant or a synthetic nucleic acid molecule. A nucleic acid molecule existing among hundreds to millions of other nucleic acid molecules within, for example, a nucleic acid library (e.g., a cDNA or genomic library) or a gel (e.g., agarose, or polyacrylamide) containing restriction-digested genomic DNA, is not an "isolated nucleic acid".

As used herein, the term "gene" means the segment of DNA involved in producing a polypeptide chain; it includes regions preceding and following the coding region (leader and trailer) involved in the transcription/translation of the gene product and the regulation of the transcription/translation, as well as intervening sequences (introns) between individual coding segments (exons).

In this application, the terms "polypeptide", "peptide", and "protein" are used interchangeably herein to refer to a polymer of amino acids. The terms apply to amino acid polymers in which one or more amino acid residues are artificial chemical mimetic of a corresponding naturally occurring amino acids, as well as to naturally occurring amino acid polymers and non-naturally occurring amino acid polymers. As used herein, the terms encompass amino acid chains of any length, including full-length proteins, wherein the amino acid residues are linked by covalent peptide bonds.

As used herein, the terms "identical" or percent "identity", in the context of describing two or more polynucleotide or amino acid sequences, refer to two or more sequences or subsequences that are the same or have a specified percentage of amino acid residues or nucleotides that are the same (for example, a variant protein used in the method of this invention has at least 70% sequence identity, preferably 80%, 85%, 90%, 91%, 92%, 93%, 94%, 95%, 96%, 97%, 98%, 99%, or 100% identity, to a reference sequence), when compared and aligned for maximum correspondence over a comparison window, or designated region as measured using one of the following sequence comparison algorithms or by manual alignment and visual inspection. Such sequences are then said to be "substantially identical". With regard to polynucleotide sequences, this definition also refers to the complement of a test sequence. The comparison window, in certain embodiments, refers to the full length sequence of a given mRNA sequence or polypeptide. For the purposes of this disclosure, variant slpA proteins include contain one or more of the first four amino acids of SEQ ID NO: 17 or their counterparts found in SEQ ID NO: 5 (amino acid positions 31-34 of SEQ ID NO: 5). Thus, variant proteins within the scope of this disclosure include 1, 2, 3 or all 4 of these amino acids (K, S, R and/or M).

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which depends in part on how the value is measured, i.e., the limitations of the measurement system. In the context of compositions containing amounts of ingredients where the terms "about" is used, these compositions contain the stated amount of the ingredient with a variation (error range) of 0-10% around the value (X±10%). In other contexts the term "about" is provides a variation (error range) of 0-10% around a given value (X±10%). As is apparent, this variation represents a range that is up to 10% above or below a given value, for example, X±1%, X±2%, X±3%, X±4%, X±5%, X±6%, X±7%, X±8%, X±9%, or X±10%.

In the present disclosure, ranges are stated in shorthand to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values. When ranges are used herein, combinations and subcombinations of ranges (e.g., subranges within the disclosed range) and specific embodiments therein are explicitly included.

An endogenous nucleic acid is a nucleic acid that is naturally present in a cell. For example, a nucleic acid present in the genomic DNA of a cell is an endogenous nucleic acid.

An exogenous nucleic acid is any nucleic acid that is not naturally present in a cell. For example, a nucleic acid vector introduced into a cell constitutes an exogenous nucleic acid. Other examples of an exogenous nucleic acid include the vectors comprising a heterologous promoter linked to an endogenous nucleic acid, e.g., a nucleic acid encoding a kinase.

The subject invention provides for the use of "homologous nucleic acid sequences" or "homologs of nucleic acid sequences". Homologs of nucleic acid sequences will be understood to mean any nucleotide sequence obtained by mutagenesis according to techniques well known to persons skilled in the art, and exhibiting modifications in relation to the parent sequences. For example, mutations in the regulatory and/or promoter sequences for the expression of a polypeptide that result in a modification of the level of expression of a polypeptide according to the invention provide for a "homolog of a nucleotide sequence". Likewise, substitutions, deletions, or additions of nucleic acid to the polynucleotides of the invention provide for "homologs" of nucleotide sequences. In various embodiments, "homologs" of nucleic acid sequences have substantially the same biological activity as the corresponding reference gene, i.e., a gene homologous to a native gene would encode for a protein having the same biological activity as the corresponding protein encoded by the naturally occurring gene. Typically, a homolog of a gene shares a sequence identity with the gene of at least about 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%. These percentages are purely statistical and differences between two nucleic acid sequences can be distributed randomly and over the entire sequence length.

In certain embodiments of the invention a subject is a mammal. Non-limiting examples of a mammal treatable according to the methods of the current invention include mouse, rat, dog, guinea pig, cow, horse, cat, rabbit, pig, monkey, ape, chimpanzee, and human. Additional examples of mammals treatable with the methods of the current invention are well known to a person of ordinary skill in the art and such embodiments are within the purview of the current invention.

For the purposes of the current invention, a probiotic food refers to a food which contains microorganisms associated with beneficial effects to humans and animals upon ingestion of the probiotic food. Non-limiting examples of probiotic food include yogurt, fermented vegetable, kefir, sauerkraut, miso soup, pickle, tempeh and kimchi.

For the purposes of this invention the term "inflammation mediated disease" or "inflammatory disease" refers to a disease characterized by a dysregulation of the normal immune response. Inflammation mediated diseases (inflammatory diseases) can cause organ damage, and are associated with increased morbidity and/or mortality. An example of immune dysregulation is the inappropriate activation of inflammatory cytokines, such as IL-12, IL-6, tumor necrosis factor (TNF) alpha, IL-10, IL-27, and IL-1 (including IL-1β and IL-1α); actions of said cytokines can lead to pathological consequences. Additionally, transcriptions factors can affect cytokine signaling, such as, for example, cMAF, which can be expressed upon IL-27 signaling and control behavior of T cells by suppressing Th17 and augmenting Tregs and IL-10 production.

For the purposes of this invention the terms "treatment, treating, treat" or equivalents of these terms refer to healing, alleviating, relieving, altering, remedying, ameliorating, improving, or affecting the condition or the symptoms of a subject suffering with a disease, for example, a gastrointestinal or lung disorder. The subject to be treated can be suffering from or at risk of developing the disorder, for example, a gastrointestinal or lung disorder, including, for example, an IBD or ARDS or be at risk of developing an IBD or ARDS. When provided therapeutically, the bacterium is provided at (or after) the onset of a symptom. The therapeutic administration of the substance serves to attenuate any actual symptom.

For the purposes of this invention, the terms "preventing, preventive, prophylactic" or equivalents of these terms are indicate that the recombinant bacterium is provided in advance of any disease symptoms and are a separate aspect of the invention (i.e., an aspect of the invention that is distinct from aspects related to the terms "treatment, treating, treat" or equivalents of these terms which refer to healing, alleviating, relieving, altering, remedying, ameliorating, improving, or affecting the condition or the symptoms of a subject suffering with an inflammatory disease, for example, a gastrointestinal or lung disorder). The prophylactic administration of the recombinant bacterium serves to prevent, reduce the likelihood, or attenuate one or more subsequent symptoms or disease.

By "therapeutically effective dose," "therapeutically effective amount", or "effective amount" is intended to be an amount of a recombinant bacterium disclosed herein or the amount of SlpA that, when administered to a subject, decreases the inflammatory response, or reduces any increase in an inflammatory response, or improve the clinical course of the disease as compared to untreated subjects. "Positive therapeutic response" refers to, for example, improving the condition of at least one of the symptoms of an inflammatory disorder.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual. Generally, the dosage of recombinant bacteria will vary depending upon such factors as the patient's age, weight, height, sex, general medical condition and previous medical history. In specific embodiments, it may be desirable to administer the bacterium in the range of about $10^4$ to about $10^{12}$ CFU, $10^5$ to $10^{11}$ CFU, $10^6$ to $10^{10}$ CFU, $10^8$ to $10^{10}$ CFU, $10^8$ to $10^{12}$ CFU, or $10^{10}$ to $10^{14}$ CFU.

In some embodiments of the invention, the method comprises administration of multiple doses of the bacterium. The method may comprise administration of 1, 2, 3, 4, 5, 6, 7, 8, 9, 10, 15, 20, 25, 30, 35, 40, or more therapeutically effective doses of a composition comprising the bacterium as described herein. In some embodiments, doses are administered over the course of 1 day, 2 days, 3 days, 4 days, 5 days, 6 days, 7 days, 10 days, 14 days, 21 days, 30 days, or more than 30 days. The frequency and duration of administration of multiple doses of the compositions is such as to reduce or prevent an inflammatory response and thereby treat or prevent a gastrointestinal or lung disorder. Moreover, treatment of a subject with a therapeutically effective amount of the recombinant bacterium of the invention can include a single treatment or can include a series of treatments. It will also be appreciated that the effective dosage of a bacterium used for treatment may increase or decrease over the course of a particular treatment. Changes in dosage may result and become apparent from the results of diagnostic assays for detecting inflammation known in the art and described herein. In some embodiments of the invention, the method comprises administration of the bacterium at several time per day, including but not limiting to 2 times per day, 3 times per day, and 4 times per day.

The present invention also includes combinations of the recombinant bacteria with one another, and/or with one or more other agents useful in the treatment of an inflammation mediated disease of the GI tract or lung. For example, bacteria of the invention may be administered in combination with effective doses of conventional anti-inflammatory agents, such as sulfasalazine, cyclosporine, prednisone, methylprednisone, budesonide, mesalamine, azathioprine, TNF inhibitors, methotrexate, or 6-mercaptopurine, a corticosteroid, infliximab or combinations thereof, for treatment of inflammation mediated diseases of the GI tract or lung. The term "administration in combination" refers to both concurrent and sequential administration of the active agents. The combination therapies are of course not limited to the agents provided herein, but include any composition for the treatment of inflammatory disorders, such as lung inflammatory disorders. Other agents useful in the treatment of an inflammation mediated disease can also include one or more viable probiotic microorganisms, including, for example, but not limited to yeasts such as *Saccharomyces* spp. *Debaromyces* spp., *Candida* spp., *Pichia* spp. and *Torulopsis* spp.; molds such as *Aspergillus* spp., *Rhizopus* spp., *Mucor* spp., *Penicillium* spp. and *Torulopsis* spp.; and bacteria such as *Bifidobacterium* spp., *Clostridium* spp., *Fusobacterium* spp., *Melissococcus* spp., *Propionibacterium* spp., *Streptococcus* spp., *Enterococcus* spp., *Lactococcus* spp., *Staphylococcus* spp., *Peptostrepococcus* spp., *Bacillus* spp., *Pediococcus* spp., *Micrococcus* spp., *Leuconostoc* spp., *Weissella* spp., *Aerococcus* spp., Oenococcus spp., and *Lactobacillus* spp. or compounds that induce the growth of said probiotics (prebiotics).

In certain embodiments, the inflammation mediated disease treated according to the current invention is IBD. IBD is an umbrella term that is used to describe disorders that involve chronic inflammation of the digestive tract. Non-limiting examples of IBD include Crohn's disease or ulcerative colitis. Additional examples of IBD are well known to a person of ordinary skill in the art and such embodiments are within the purview of the current invention. As discussed above, the disclosed methods and compositions are aimed at improving the condition of at least one of the symptoms of an inflammatory disorder, such as IBD.

In certain embodiments, the inflammation mediated disease treated according to the current invention is lung inflammation, including, for example, acute respiratory distress syndrome (ARDS), asthma, bronchiectasis, bronchiolitis obliterans, bronchitis, chronic obstructive pulmonary disease (COPD) (including chronic bronchitis and emphysema), eosinophilic granulomatosis, hypersensitivity pneumonitis, interstitial lung disease, pulmonary artery hypertension, and sarcoidosis. In further embodiments, pathogenic agents can lead to lung inflammation that can be treated by methods of the subject invention, including viral and bacterial agents that induce pneumonia. Pathogenic agents can include coronaviruses, including Middle East Respiratory Syndrome coronavirus (MERS-CoV), Severe Acute Respiratory Syndrome (SARS)-CoV-2 and SARS-CoV; influenza viruses; respiratory syncytial virus (RSV); and *Coccidioides* (the causative agent of Coccidioidomycosis).

The current invention provides SlpA as an effector molecule expressed by bacteria and which provide protective role in inflammation mediated diseases, for example, inflammation mediated diseases of gastrointestinal tract and lung, such as ARDS and IBD. Accordingly, certain embodiments of the current invention provide an isolated bacterial SlpA protein or a variant thereof.

An example of bacterial SlpA protein is provided by a protein having the sequence of SEQ ID NO: 5 or SEQ ID NO: 17 or a variant protein having at least 90% sequence identity to the sequence of SEQ ID NO: 5. As discussed above, such variant proteins include one or more of the first four amino acids of SEQ ID NO: 17 or one, two, three or four of the amino acids found at positions 31-34 of SEQ ID NO: 5. In certain embodiments, the presence of the first four amino acids of SEQ ID NO: 17 or the amino acids found at positions 31-34 of SEQ ID NO: 5 can enable the secretion of the SlpA protein. In certain embodiments, the SlpA protein is provided by a protein encoded by a nucleotide sequence having the sequence of SEQ ID NO: 6. Certain other examples of SlpA protein are provided by Uniprot access numbers C2HR60 (SEQ ID NO: 7), P35829 (SEQ ID NO: 8), G1UE81 (SEQ ID NO: 9), Q9Z4J9 (SEQ ID NO: 10), H6VTN4 (SEQ ID NO: 11), Q09FM2 (SEQ ID NO: 12), L7YE91 (SEQ ID NO: 13), K8DVK7 (SEQ ID NO: 14) and F0NUB7 (SEQ ID NO: 15) (each of which is hereby incorporated by reference in its entirety). Further, each of the aforementioned SlpA proteins has an annotated signal peptide. Any variation from SEQ ID NOs: 5-15 can be in the annotated signal peptide, the mature SlpA protein, or a combination thereof. Additional examples of SlpA proteins are well known to a person of ordinary skill in the art and such embodiments are within the purview of the current invention for use in formulation of the compositions disclosed herein as well as the methods of using such compositions for the treatment of inflammatory diseases.

For the purposes of this invention a variant protein indicates that the variant protein is different than its naturally occurring counterpart in some manner. Certain examples of modifications which can distinguish a variant protein from its naturally occurring counterpart include mutations in the amino acid sequences (e.g., point mutations or the introduction of one or more glycosylation site into the protein), non-naturally occurring post-translational modifications (e.g. glycosylation or phosphorylation patterns), attachment to the protein of extraneous molecules (e.g. molecular labels, such as radioisotopes or fluorescent labels, polyethyleneglycol (PEG), etc.). Additional examples of such modifications are well known to a person of ordinary skill in the art and such embodiments are within the purview of the current invention.

In one embodiment, the SlpA variant protein according to the current invention comprises a molecular label conjugated to a bacterial SlpA protein, for example, SlpA protein having the sequence of SEQ ID NO: 5 or the protein having at least 70%, 75%, 80%, 85%, 90%, 91%, 92%, 93%, 94%, 95%, 96%, 97%, 98%, or 99% sequence identity to the sequence of SEQ ID NO: 5. In one embodiment, the non-naturally occurring SlpA variant protein according to the current invention comprises a molecular label conjugated to a bacterial SlpA protein, for example, SlpA protein encoded by the nucleotide sequence of SEQ ID NO: 6 or the protein having at least 70%, 75%, 80%, 85%, 90%, 91%, 92%, 93%, 94%, 95%, 96%, 97%, 98%, or 99% sequence identity to the sequence of SEQ ID NO: 5. The label can be a radiolabel, fluorescent label, affinity label, targeting label.

In another embodiment, the SlpA variant protein according to the current invention comprises a protein having one or more mutations in the amino acid sequence of a bacterial SlpA protein, for example, SlpA protein having a sequence of SEQ ID NO: 5 or having a sequence at least 70%, 75%, 80%, 85%, 90%, 91%, 92%, 93%, 94%, 95%, 96%, 97%, 98%, or 99% identical to the sequence of SEQ ID NO: 5. In certain embodiments, the SlpA variant protein comprises about 1 to about 50 mutations, about 1 to about 25 mutations, about 3 to about 15 mutations, or about 5 to about 10 mutations. In another embodiment, the mutations do not negatively affect the ability of the SlpA variant protein of the current invention of protecting against inflammation mediated diseases, for example, inflammation mediated diseases of gastrointestinal tract, such as IBD, or lungs, such as ARDS. Such protein variants will contain one or more of the amino acids at positions 1-4 or SEQ ID NO: 17 or one or more of the amino acids at positions 31-34 of SEQ ID NO: 5.

Naturally occurring and variant SlpA proteins can have signal peptides. The signal peptides can be cleaved from the remaining amino acid sequence, resulting in the mature SlpA protein sequence. In certain embodiments, the current invention comprises a protein having one or more mutations in the signal peptide of the SlpA, for example, SlpA signal peptide having a signal sequence of SEQ ID NO: 16 or having a sequence at least 70%, 75%, 80%, 85%, 90%, 91%, 92%, 93%, $_{94}$%, 95%, 96%, 97%, 98%, or 99% identical to the signal sequence of SEQ ID NO: 16. The signal peptide can have about 1 to about 30 mutations, about 2 to about 29 mutations, about 5 to about 15 mutations, or about 5 to about 10 mutations. In certain embodiments, the protein of the current invention comprises the mature SlpA protein sequence that can be identical to the mature protein sequence of SEQ ID NO: 17. In alternative embodiments, the protein variants of the current invention comprises a mature SlpA protein that can have about 1 to about 30 mutations, about 5 to about 20 mutations, or about 5 to about 20 mutations to the mature protein sequence of SEQ ID NO: 5. Such protein variants will contain one or more of the amino acids at positions 1-4 or SEQ ID NO: 17 or one or more of the amino acids at positions 31-34 of SEQ ID NO: 5.

In certain embodiments, the signal peptide of SlpA is about 5, about 10, about 15, about 20, about 21, about 22, about 23, about 24, about 25, about 26, about 27, about 28, about 29, about 30, about 31, about 32, about 33, about 34, about 35, about 36, about 37, about 38, about 39, or about 40 amino acids in length. In certain embodiments, the mature SlpA protein can be about 400, about 401, about 402, about 403, about 404, about 405, about 406, about 407, about 408, about 409, about 410, about 411, about 412, about 413, about 414, about 415, about 416, about 417, about 418, about 419, about 420, about 421, about 422, about 423, about 424, about 425, about 426, about 427, about 428, about 429, or about 430 amino acids in length. In preferred embodiments, the signal peptide of SlpA can be the first 30 amino acids of SEQ ID NO: 5, and the mature protein can be the last 417 amino acids of SEQ ID NO: 5. In more preferred embodiments, the signal peptide of SlpA can be the amino acid sequence of SEQ ID NO: 16, and the mature protein can be the amino acid sequence of SEQ ID NO: 17. In certain embodiments, the variants of the mature protein of SlpA has the first four amino acids of SEQ ID NO: 17 or amino acids 31 to 34 of SEQ ID NO: 5.

In certain embodiments, the bacterial cell, preferably *L. lactis*, that synthesizes the SlpA protein can secrete SlpA. The secretion of the SlpA can permit a more efficient means of purifying the SlpA protein from the bacterial cells when compared to purifying SlpA from bacteria that express SlpA on the surface of the bacterial cell. The secretion of SlpA can also more effectively treat inflammatory diseases than SlpA that is not actively or passively secreted by the bacterial cell synthesizing said SlpA protein.

In certain embodiments, the bacterial cell, preferably *L. lactis*, which synthesizes the SlpA protein can have other genes modified. Examples of genes involved in generating auxotrophic cell lines include but are not limited to ade1, tyrS.d8, BipARS.d6, argD, bioAB, fabH, fab, bioH, leuA, nadA, hisBF, cysC, argBH, leuB frdD, upAI, and thyA gene modifications. These genes can be deleted entirely or have a portion of the gene or promoter region of said gene modified, for example, by a recombination event that inserts a genetic construct encoding SlpA or other genes. The genes can also be mutated to reduce or eliminate the transcription of said genes. In some embodiments, the genes can be modified to prevent the bacteria from growing outside of a desired location. For example, nucleotide supplementation of the bacterial cells can be required for growth. In other embodiments, genetic modifications can result in improving bacteria fitness, survivability, or gastric transit time. In other embodiments, additional therapeutic genes can be added to the *L. lactis* genome.

An embodiment of the current invention also provides a composition comprising a SlpA variant protein and a pharmaceutically acceptable carrier and/or excipient.

The pharmaceutically acceptable carrier and/or excipient comprise substances, such as an inert vehicle, or pharmaceutical acceptable adjuvants, preservatives etc. Examples pharmaceutically acceptable substances are well known to a person of ordinary skill in the art and such embodiments are within the purview of the current invention.

The pharmaceutical composition may be a liquid formulation or a solid formulation. When the pharmaceutical composition is a solid formulation it may be formulated as a tablet, a sucking tablet, a chewing tablet, a chewing gum, a capsule, a sachet, a powder, a granule, a coated particle, a coated tablet, an enterocoated tablet, an enterocoated capsule, a melting strip or a film. When the pharmaceutical composition is a liquid formulation it may be formulated as an oral solution, a suspension, an emulsion or syrup. Said composition may further comprise a carrier material independently selected from, but not limited to, the group consisting of lactic acid fermented foods, fermented dairy products, resistant starch, dietary fibers, carbohydrates, proteins, and glycosylated proteins.

Pharmaceutical compositions, as disclosed herein, can be formulated in accordance with standard pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York) known by a person skilled in the art. Pharmaceutical composition according to the invention may also be formulated to release active agents substantially immediately upon administration or at any predetermined time or time period after administration.

For oral administration, the composition can be formulated into conventional oral dosage forms such as tablets, capsules, powders, granules and liquid preparations such as syrups, elixirs, and concentrated drops. Non-toxic solid carriers or diluents may be used which include, for example, pharmaceutical grades of mannitol, lactose, starch, magnesium stearate, sodium saccharine, talcum, cellulose, glucose, sucrose, magnesium, carbonate, and the like. For compressed tablets, binders, which are agents which impart cohesive qualities to powdered materials are also necessary. For example, starch, gelatin, sugars such as lactose or dextrose, and natural or synthetic gums can be used as binders. Disintegrants are also necessary in the tablets to facilitate break-up of the tablet. Disintegrants include starches, clays, celluloses, algins, gums and cross-linked polymers. Moreover, lubricants and glidants are also included in the tablets to prevent adhesion to the tablet material to surfaces in the manufacturing process and to improve the flow characteristics of the powder material during manufacture. Colloidal silicon dioxide is most commonly used as a glidant and compounds such as talc or stearic acids are most commonly used as lubricants.

Pharmaceutical composition can also be formulated as a food composition, a dietary supplement, a functional food, a medical food or a nutritional product as long as the required effect is achieved, i.e. treatment and/or prevention of an inflammatory disorder of the gastrointestinal tract. Said food composition may be chosen from the group consisting of beverages, yogurts, juices, ice creams, breads, biscuits, crackers, cereals, health bars, spreads and nutritional products. The food composition may further comprise a carrier material, wherein said carrier material is chosen from the group consisting of lactic acid fermented foods, fermented dairy products, resistant starch, dietary fibers, carbohydrates, proteins and glycosylated proteins. In other embodiments, pharmaceutical composition can be formulated using beads and nanoparticles. In other embodiments, pharmaceutical composition can be formulated to provide an advantage to *L. lactis*, including, but not limited to, improved gastric survival, improved intestinal availability, or improved epithelial cell contact.

Accordingly, the current invention provides a method of treating or preventing an inflammation mediated disease of the gastrointestinal system or systemic inflammatory disorders in a subject, the method comprising, administering to the subject a therapeutically effective amount of the composition comprising the SlpA protein or a variant SlpA protein. In certain embodiments, the composition is orally administered to the subject. SlpA protein or a variant can be administered or formulated in combination with effective doses of conventional anti-inflammatory agents, such as sulfasalazine, cyclosporine, prednisone, methylprednisone, budesonide, mesalamine, azathioprine, TNF inhibitors, methotrexate, or 6-mercaptopurine, a corticosteroid, infliximab or combinations thereof, for treatment of inflammation mediated diseases of the GI tract or the lung. Non-limiting examples of such diseases include IBD and ARDS, for example, Crohn's disease or ulcerative colitis.

Thus, the bacterial cells, in some embodiments express a protein that has the amino acid sequence of SEQ ID NO: 5 or the variant protein has the amino acid sequence at least 70%, 75%, 80%, 85%, 90%, 91%, 92%, 93%, 94%, 95%, 96%, 97%, 98%, or 99% identical to the sequence of SEQ ID NO: 5 or 17, provided that the variant protein contains one or more of the amino acids corresponding to positions 31-34 of SEQ ID NO: 5 or amino acids 1-4 of SEQ ID NO: 17. In certain aspects of the invention, these bacterial cells are *Lactococcus* strains. Non-limiting examples include, but are not limited to, *L. chungangensis, L. formosensis, L. fujiensis, L. hircilactis, L. garvieae* (including, for example, *L. garvieae* subsp. *garvieae* and *L. garvieae* subsp. *bovis*), *L. lactis* (including, for example, *L. lactis* subsp. *cremoris, L. lactis* subsp. *hordniae, L. lactis* subsp. *lactis*, and *L. lactis* subsp. *tructae*), *L. laudensis, L. nasutitermitis, L. piscium, L. plantarum, L. raffinolactis*, and *L. taiwanensis*.

In certain embodiments, the presence and/or amount of SlpA protein can be monitored in the gastrointestinal system of the subject. The monitoring can occur before, during, or after administration of a composition comprising SlpA and/ or a bacteria synthesizing SlpA. In preferred embodiments, SlpA can be detected within about 24 to about 48 hours, about 12 to about 36 hours, or about 12 to about 24 hours after administration of the compositions of the subject invention. Fecal samples can be collected from the subject and the amount of SlpA in the sample can be determined using any protein detection and/or quantification technique known in the art that detects and/or quantifies a specific protein. Examples of acceptable protein detection and/or quantification techniques include, for example, high-performance liquid chromatography, liquid chromatograph-mass spectrometry, enzyme-linked immunosorbent assay (ELISA), protein immunoprecipitation, immunoelectrophoresis, Western blot, or protein immunostaining.

In certain embodiments, administration of a composition comprising SlpA and/or a bacteria synthesizing SlpA can modify the expression of cell surface receptors, cytokines, chemokines, enzymes, antiviral genes, or transcription factors including, for example, cell surface receptors CD38, CD40, CD80, IL-15RA, IL-2RA, CD300e, CCR7, and FFAR2; cytokines IL-27, IL36γ, IL-10, IL-12 IL-17, EBi3, CSF, GM-CSF, TNF, and LTA and chemokines CCL8, CXCL9, CCL5 (RANTES), Eotaxins (CCL11, CCL24, and CCL26), and CXCL10; enzymes ADA, SOCS3, SOD2KYNU, and ID01; antiviral genes IRF1, IFI44, IFI44L, OSA2, OSAL, ISG15, MX1, APOBEC3A, GBP4, and GBP5; and transcription factor RORγt. In specific embodiments, the levels of proinflammatory cytokines IL-12 (p70), IL-12 (p40), IL-17, TNF, Eotaxins and RANTES can be decreased and levels of IL-10 can be increased.

Materials and Methods

Generation of R110: The SlpA expression cassette was integrated in *L. lactis* genome using standard double homologous recombination methods [18, 19]. To direct chromosomal integration, we synthesized DNA encoding the slpA sequence flanked 5' and 3' by 500 bp overhangs homologous to the upstream and downstream thyA target gene sequence region (Blue Heron Biotech, Bothell, WA). SlpA-thyA was inserted into the multi cloning site (MCS) of the pRISE1.2 plasmid (Rise Therapeutics, Rockville MD), which contains a temperature-sensitive origin of replication. Transformation of the final plasmid was done by electroporation at 2000V (Eporator®, Eppendorf, Enfield, CT). Cells were initially grown at 30° C., and then the temperature was shifted to 37° C. to select for integrant cells. The thyA homologous sequences allowed stable slpA insertion at the thyA locus via a double crossover event, replacing thyA from the *L. lactis* chromosome. The purpose of targeting and deleting the thyA gene is to allow for containment; that is, the SlpA expressing *L. lactis* will not propagate without thymidine supplementation [20]. A positive selection system was utilized to identify clones containing the integrated slpA expression cassette as previously described [19, 21]. For positive selection, M17 medium (Millipore Sigma, Burlington, MA) was supplemented with 4 µg/ml of the dihydrofolate reductase (DHFR) inhibitor trimethoprim and 20 µg/ml of thymidine (Millipore Sigma, Burlington, MA). In the presence of trimethoprim, wild-type *L. lactis* containing a functional thyA led to tetrahydrofolate (THF) pool depletion and cell death through the inhibition of numerous THE dependent reactions. However, inactive thyA (via slpA cassette integration) allowed THF levels to remain high, even in the presence of trimethoprim. Thus, *L. lactis* containing a stably integrated SlpA expression cassette grew on minimal media supplemented with trimethoprim and thymidine. Stability of the integration event was confirmed by growing the selected clones under non-selective conditions in M17 media supplemented with 20 µg/ml thymidine for 100 generations. The selected clone was named R110.

Mice: Eight-week-old Rag1$^{-/-}$ (Jackson Laboratory; Stock #002216) and C57BL/6 (Jackson Laboratory Stock #00664) were housed in the Animal Care Facility at the University of Florida Gainesville. Food and water were provided ad libitum, and all animal procedures were approved by the Institutional Animal Care and Use Committee of the University of Florida.

Detection of R110 and NCK2187 in murine feces: Two sets of primers were designed to amplify the SlpA expressing cassette from NCK2187 or R110. The incorporating DNA for SlpA in R110 was codon-optimized for efficient expression; therefore, these primers were unique for identifying R110 and NCK2187 in DNA isolated from feces. Fecal DNA was isolated using Quick-DNA Fecal/Soil Microbe Microprep Kit (Zymo Research, Irvine, CA; Cat D6012) as per the manufacturer's instruction. 100 ng of DNA used for semiquantitative PCR with 200 nM primer concentration with SsoAdvanced Universal SYBR Green Supermix (Bio-Rad, Hercules, CA). PCR was run on a MIC PCR platform and data were analyzed using $2^{\wedge \Delta CT}$ method.

T cell colitis induction: For the initiation of colitis CD45RB$^{hi}$ CD4$^+$ T cells into Rag1$^{-/-}$ mice, spleen cell suspensions obtained from healthy C57BL/6 mice were pooled, and CD4$^+$ T cells were isolated using EasySep™ Mouse CD4$^+$ T Cell Isolation Kit (Stemcell Technology, Vancouver, BC, Canada; Cat #19852). Isolated CD4$^+$ T cells were stained with anti-CD45RB (Clone C363-16A), -CD3 (Clone 17A2), -CD4 (Clone GK1.5), and Zombie Violet™ Fixable Viability Kit (BioLegend, San Diego, CA) before sorting them on SONY SH800 cell sorter. Viable CD45RB$^{HI}$ cells were sorted and washed with PBS before injecting into the 8-week old Rag1$^{-/-}$ mice. All mice were injected with 5×10$^5$ cells/mouse via the intraperitoneal route.

Fecal Occult blood determination: Fecal occult blood was determined by using Hemoccult Sensa (Cat #64151; Beckman Coulter, Inc. Brea, CA). Mouse feces were smeared over the paper box provided in the kit and left for three days at room temperature. A drop of the developer was added onto the smeared feces, and the color development was noted after 30-sec. An arbitrary grade was decided based on the no color (0) to dark blue (4) to determine the level of fecal occult blood, as done previously [15].

FITC dextran assay Passive transepithelial absorption of FITC-labeled dextran (Sigma-Aldrich, St. Louis) in vivo was used to determine intestinal barrier function as previously described [15]. Mice were gavaged with FITC-dextran, MW 4,000 (60 mg/100 g body weight). Blood was collected retro-orbitally after proper anesthetization. Fluorescence intensity in the serum was measured with a fluorimeter (485 nm excitation, 519 nm emission). FITC-dextran concentrations in the mouse sera were determined from standard curves generated by serial dilution of FITC-dextran using blank subtraction in the test samples using sera from mice that were not gavaged with the permeability tracer.

Fecal albumin assay: Murine Feces were dissolved in dilution buffer (50 mM Tris, 0.14 M NaCl, 0.05% Tween 20, pH 8.0) to a concentration of 100 mg/ml. Albumin contents were measured using the mouse albumin ELISA Kit (Cat #E99-134; Bethyl Laboratory, Montgomery, TX) according to the manufacturer's instructions.

Isolation of colonic lamina propria cells: Freshly isolated colons were washed with PBS and then incubated with 15 mM EDTA solution in PBS for 30 mins on ice to remove epithelial cells. After a rinse with PBS, 0.5 cm long pieces of colon were digested with Collagenase VIII (250 µg/ml) and DNAseI (150 µg/ml) for 90 mins at 37° C., in 5% $CO_2$. The digested tissues were washed with cold PBS and resuspended in 40% percoll, and 80% percoll underlay before centrifugation at 1300×g for 20 minutes at room temperature. After removing the top fat- and epithelial cell-rich section, cells in the upper layer were collected, washed, and stained for flow cytometry.

Flow cytometry analysis of isolated cells: Colonic lamina propria cells were stained with LIVE/DEAD Aqua Dead Cell Stain kit (Molecular Probes, Life Technologies, Carlsbad, CA). Washed cells were incubated with Mouse Fc Blocking Reagent (Miltenyi Biotec, Auburn, CA) as per the manufacturer's instructions before staining with combinations of the following antibodies or their corresponding isotype controls: CD45 (30-F11), CD3 (145-2C11), CD4 (RM4-5), IL-17A (TC11-18H10.1)/Rat IgG1, κ, IL-10 (JES5-16E3)/Rat IgG2b, κ, RORγt (AFKJS-9)/Rat IgG2a, x. To detect intracellular cytokines, cells were fixed and permeabilized with BD Cytofix/Cytoperm (BD Biosciences, Franklin Lakes, NJ). Colonic T cells were stimulated with phorbol 12-myristate 13-acetate (PMA) (50 ng/ml) and ionomycin (2.5 µg/ml) in the presence of Brefeldin A (Biolegend) for 2.5 h. The Transcription Factor Fixation/Permeabilization Kit from eBioscience (San Diego, CA, USA) was used for FoxP3 staining. After staining, a BD LSRFortessa (BD Biosciences) cell analyzer was used to acquire fixed cells. Data were analyzed with FlowJo software (Tree Star, Ashland, OR, USA). Antibodies and their corresponding isotype controls were purchased from eBioscience, BioLegend, BD Pharmingen, or R&D Systems (Minneapolis, MN, USA).

Microbial composition analysis: Mice feces were sent to Novogene Corporation Inc. (Beijing, China) for microbiota analysis. The total fecal DNA was isolated and amplified using the primers specific for V3 and V4 regions of the 16s rRNA gene. The amplicons were sequenced using Illumina high throughput sequencer with paired-end sequencing strategy. The sequences were saved in FASTQ format for further analysis. The obtained sequences were identified from phylum to species levels using Silva database (version 2017.12).

Quantitative Real-Time PCR: Total RNA were isolated from the tissues or the cells using a combined protocol with Trizol and Aurum Total RNA Mini kit (Cat #7326820, BioRad). The concentration and purity of RNA samples were determined by measuring the absorbance (A260/A280) using a NanoDrop 2000 spectrophotometer (Thermo Fisher Scientific, Waltham, MA). 0.5 µg of RNA was converted into cDNA using Superscript III (Invitrogen Corporation, Carlsbad, CA). cDNA was used as the template for qPCR analysis. For the final 10-1 reaction, 0.1 µl of cDNA was mixed with 5 µl of SYBR green and 10 pmol of both forward and reverse primers. qPCR was performed on a MIC PCR platform, and differences in the transcripts were analyzed using the threshold cycle ($2^{-\Delta\Delta CT}$) method.

Murine dendritic cells experiment: Bone marrows from mice were isolated by flushing the femur and tibia. The bone marrow cells were cultured with 20 ng/ml of murine GMCSF (Cat #713704, Biolegend, San Diego, CA) for 18 h. Later, the suspended cells were removed, and fresh media with GMCSF was added to the attached cells. Three days after initiation, fresh GMCSF was added to the culture. After a week, cells in suspension were collected, washed, and stimulated with purified SlpA.

Human dendritic cells experiment: Human peripheral blood monocytes were isolated from two human donors using the lymphocyte separation medium (LSM, Corning Scientific, Tewksbury, MA). Monocytes were isolated from PBMCs using CD14 MicroBeads (Miltenyi, CA). $CD14^+$ monocytes were cultured in Mo-DC differentiation medium for seven days and in maturation medium for additional three days. Human DCs were co-incubated with the wild-type L. lactis or SlpA expressing L. lactis (R110) at a ratio of 1:1 overnight at 37° C. The supernatant was then used for analysis.

RNAseq analysis: RNA-seq was performed using the paired-end sequencing according to standard Illumina protocols. The quality of RNA-Seq fastq data was checked using the FasQC program. Data passing the quality control were imported into CLC Genomics Workbench (Version 20) for RNA-Seq analysis. The Gene expression table was generated by using the *Homo sapiens* (hg38) genome as the reference sequence. Significantly differential expression genes were determined with a selection threshold of P-value ≤0.05 and log 2-fold change ≥1. Duplicate samples were used for each condition.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1—Generation of *Lactococcus lactis* Expressing a Secreted Version of SlpA We previously published that SlpA expressed on the surface of *Lactobacillus acidophilus* NCFM (NCK2187) protects from murine colitis [15]. To further increase the expression of SlpA and use a more acceptable delivery platform for human studies, we develop an L. lactis probiotic expressing high levels of secreted SlpA to deliver the protein at the inflammatory intestinal mucosae. Since prior work relied on NCK2187 L. acidophilus, which does not encode a containment mechanism to control the genetically modified organism's environmental growth after excretion, we generated a new L. lactis strain that expresses SlpA from a genome integrated cassette. The R110 cell line was generated by integrating the SlpA expression cassette into the L. lactis genome using double homologous recombination methods. We employed a proprietary plasmid (pRISE 1.2, Rise Therapeutics), which contains a temperature-sensitive origin of replication and the SlpA gene flanked by 500 bp sequences 5' and 3' of thyA coding region [19, 21]. When transformed into *L. lactis* and growth temperature shifted to 37° C., the SlpA expression cassette is inserted at the thyA locus via a double crossover event, replacing the *L. lactis* thyA from the chromosome (this *L. lactis* strain is designated as R110). The purpose of targeting and deleting the thyA gene is to enable an already vetted containment strategy [20, 22, 23]; that is, when R110 is excreted, it will not propagate due to the lack of thymidine. The *L. lactis* clones containing a stably integrated SlpA expression cassette were selected on minimal media supplemented with trimethoprim and thymidine, as previously described [24, 25]. The stability of the integration event was confirmed by growing the clones under non-selective conditions for 100 generations. A PCR strategy was used to screen clones for proper SlpA gene integration. Three pairs of unique primers representing sequence from either slpA or the flanking thyA untranslated regions were used for the PCR screening (FIG. 1A).

Example 2—R110 Clinical Candidate Growth, SlpA Expression, and Stability

To confirm that the SlpA cassette integration and protein expression did not alter the bacterium growth characteristics, SlpA-expressing *L. lactis* clone 110 was grown in M17 medium with or without thymidine-supplementation and compared to the wild type *L. lactis* (WT) and the thyA gene deleted *L. lactis* strains wild type as control. Individual colonies were selected from freshly plated samples and the growth of each strain was followed in duplicate. Clone R110 demonstrated growth comparable to the wild-type *L. lactis* strain when the culture medium was supplemented with thymidine (data not shown). As expected, in the absence of thymidine, clone R110 did not grow as well as the WT *L. lactis* strain (FIG. 1B). The advantage of genome integration is to obtain a cell line that expresses the SlpA protein more stably and consistently from passage to passage. To confirm SlpA stable expression, R110 was subjected to continuous culture for 20 passages. Culture samples were taken at passage 1, 5, 9, 13, 17, and 20, cells were pelleted, and lysates were generated. SlpA protein expression levels were measured by a quantitative ELISA on both cell lysate and supernatant (FIG. 1C). R110 SlpA expression levels remained similar throughout the 20 passages tested, a feature of a stable clone. This was also confirmed by Western blot analysis (FIG. 1D).

Example 3—R110 does not Permanently Colonize the Mouse Gut and has a More Limited Intestinal Availability than NCK2187

The survival and maintenance of gut microbiota is complex, and an intricate balance between the host and the microbe is needed. Therefore, the introduction of new bacteria often changes the composition and may affect the host's health. To test whether the orally administered bacteria would colonize the gut, we gavaged mice with $1 \times 10^9$ CFU of R110 and NCK2187. Mice feces were collected every day for four days, total DNA isolated, and the presence of bacteria was detected using a quantitative real-time PCR targeting slpA. As previously reported, NCK2187 was detected for three days post administration in the feces (FIG. 2A). In contrast, surprisingly R110 was detected in feces on day one but not on subsequent days (FIG. 2B). We then repeated the experiment with earlier time points to verify excretion. R110 started to be detected as early as four hours post-administration and peaked between 8 to 12 hours (FIG. 2C). To test whether R110 engrafts in the gut, a new *Lactococcus* line expressing SlpA from a plasmid carrying erythromycin cassette was constructed (R105). The R110 was fed to mice and one-day post gavage mice were euthanized to collect fecal, caecal, and small intestinal contents, which were dissolved in sterile PBS and plated on M17 agar plates containing erythromycin (5 µg/ml). We did not observe many erythromycin-resistant bacteria from the intestinal and caecal contents; however, the fecal sample had higher numbers of erythromycin-resistant colonies, suggesting that the majority of R110 transits through the colon more quickly than NCK2187 (FIG. 11).

Example 4—Increased Protection from T Cell-Mediated Colitis in Mice Administered with R110 Compared to NCK2187

Figure 3B:
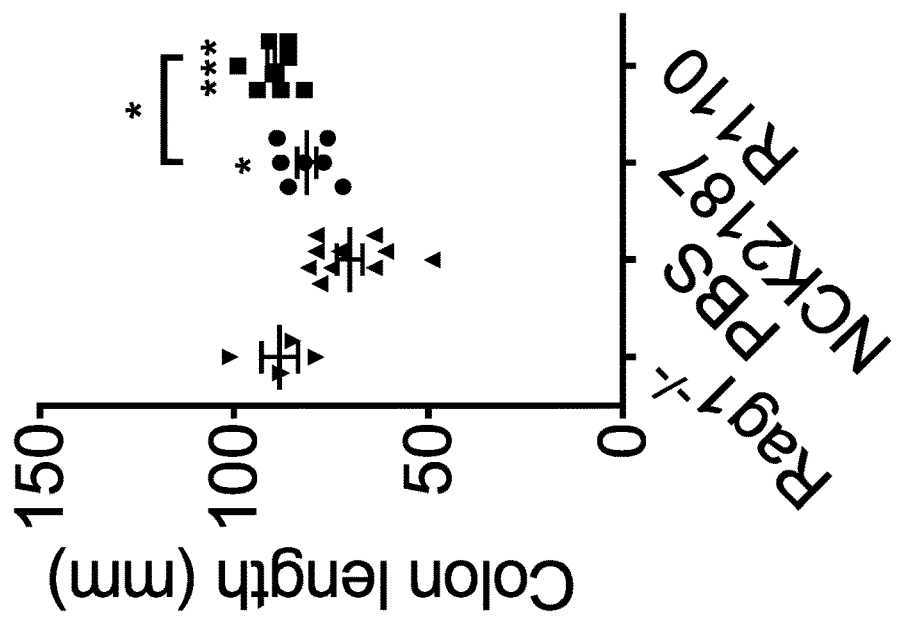
FIGS. 3A-3F: SlpA-expressing bacteria mitigate colitis. C57BL/6 Rag1$^{-/-}$ mice were injected with $10^6$ CD4$^+$ CD45RB$^{Hi}$ T cells and then orally gavaged with NCK2187 (square), R110 (triangle), or PBS (circle), 3 days after transfer, and once a week for the next seven consecutive weeks. Colitis severity was determined by weight loss, gut permeability, (fecal occult blood) FOB, colon length, and histopathology.
Figure 3A:
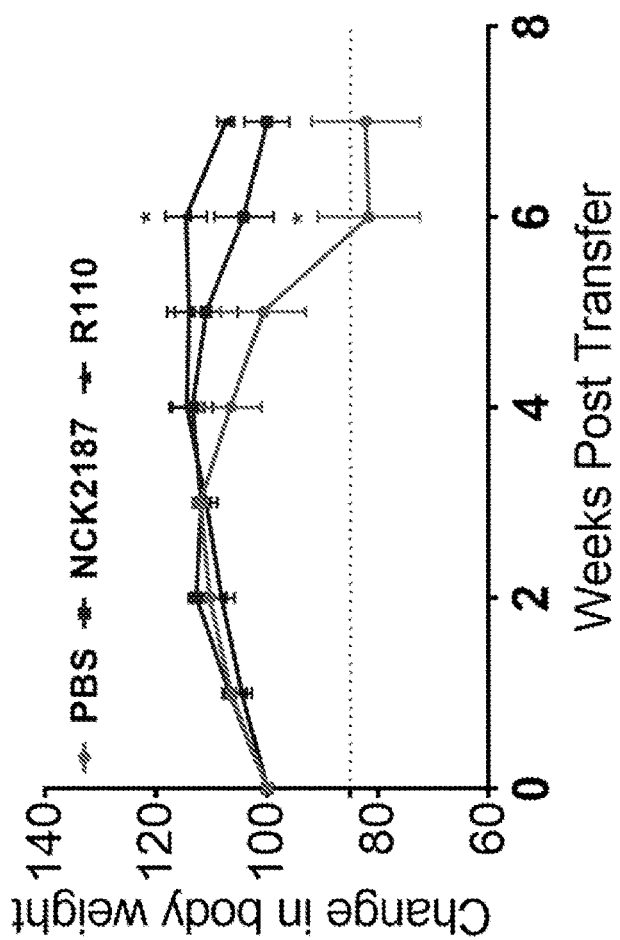

We tested R110 in the T cell adoptive transfer model of colitis, which shares the pathophysiology of human Crohn's disease. Rag1-deficient mice were injected with $5 \times 10^5$ naïve T cells (CD3$^+$CD4$^+$CD45RB$^{Hi}$) to induce colitis. Mice were fed with $1 \times 10^9$ CFU of freshly prepared R110 every week, starting four days before introducing naïve T cells. A group of mice was also provided with $1 \times 10^9$ NCK2187 as a positive control, and PBS as a negative control. Mice were weighed every week for eight weeks for evaluation of the disease outcome, and feces were collected weekly to evaluate the fecal occult blood as a measure of colitis severity. Mice fed with R110 or NCK2187 resisted the weight loss (FIG. 3A). In contrast, mice fed with PBS lost more than 15% of their initial weight (p<0.05 compared to RHO and NCK2187) after six weeks, and some mice in this group succumbed (data not shown).

Figure 3F:
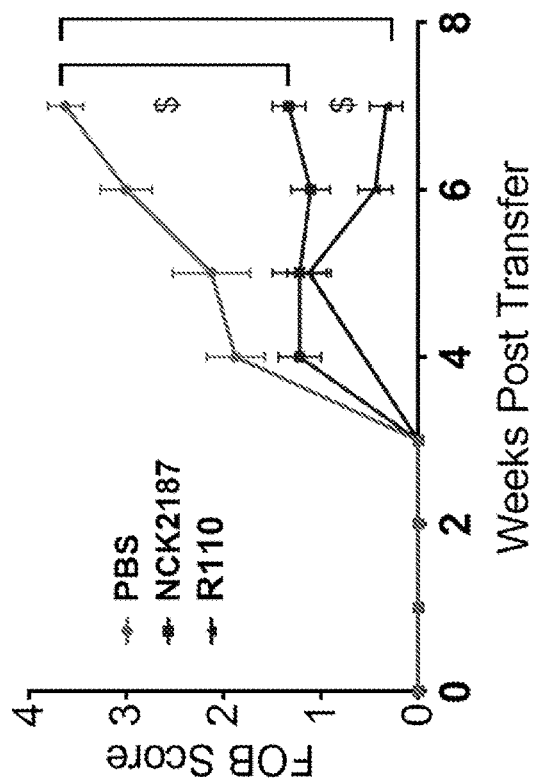
Figure 3C:
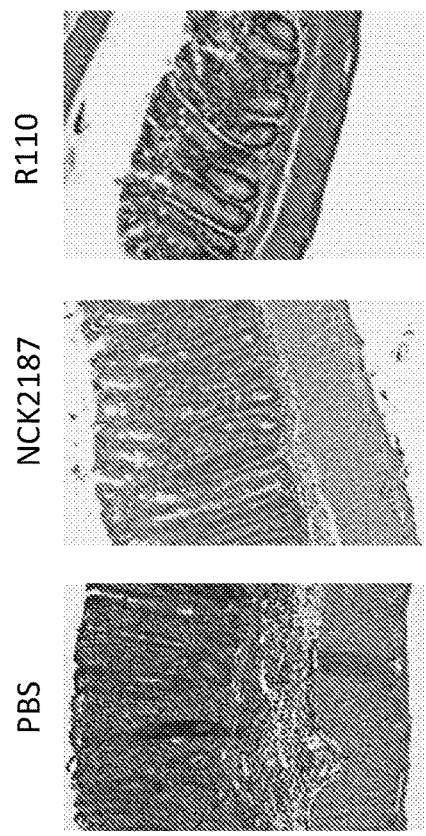
Figure 3E:
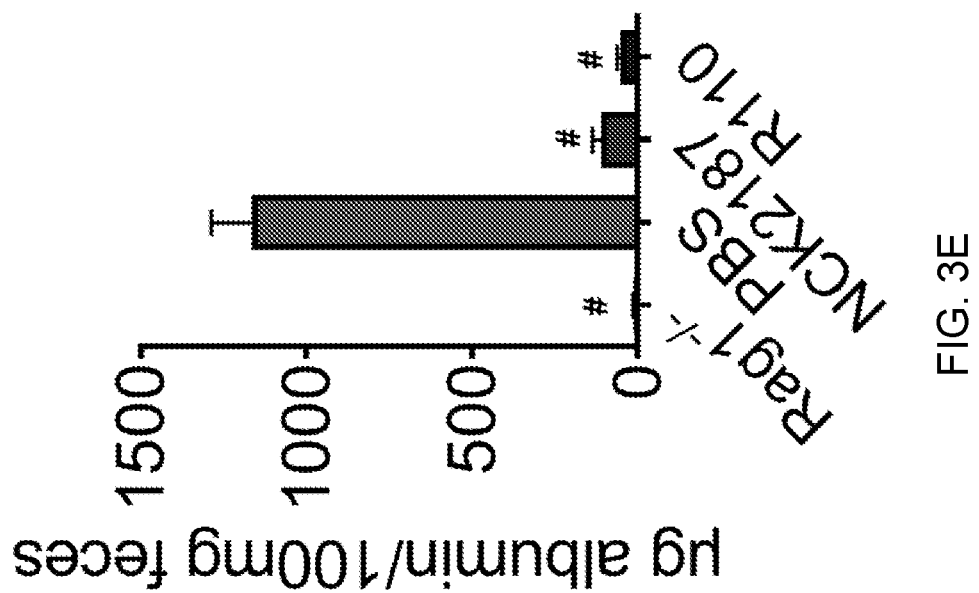
Figure 12:
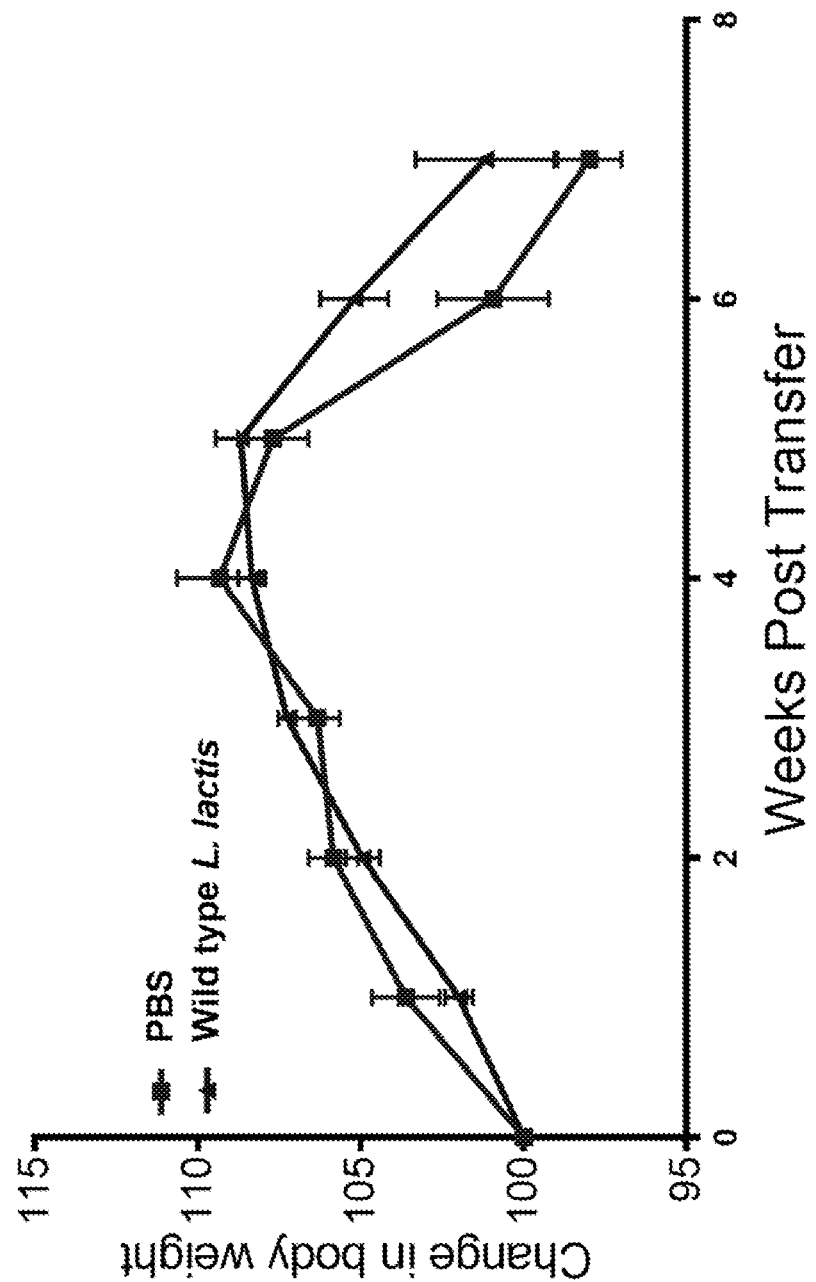
FIG. 12: C57BL/6 Rag1$^{-/-}$ mice were injected with 10$^6$ CD4$^+$CD45RB$^{Hi}$ T cells and then orally gavaged with WT *lactis* (triangle) or PBS (square) 3 days before transfer, and subsequently once a week for seven consecutive weeks. Each mouse was weighed every week, and the changes were depicted using the weight at the initiation of the experiment as 100 percent.

Mitigation of colitis by SlpA was also seen at tissue level. Eight weeks after introducing naïve T cells, mice were sacrificed, and colon length was measured. During colitis, the colon shrinks and becomes fragile due to infiltrating cells and ongoing inflammation. Upon measurement of the colon length, treatment with R110 or NCK2187 restored the colon to their standard length, with an unexpected and statistically significant increase in colon length in mice treated with R110 compared to NCK2187, indicating that R110 is more efficacious in preventing colitis (FIG. 3E). Histopathological evaluation of colonic tissues showed a sharp reduction in inflammatory cells in the colon of mice fed with R110 or NCK2187 (FIG. 3F), but not in control mice. Overall, oral treatment with R110 significantly protected mice from colitis. Similar studies were carried out using the wild-type *L. lactis*; however, the wild-type strain did not protect the mice from colitis-mediated weight loss in mice (FIG. 12).

Figure 3D:
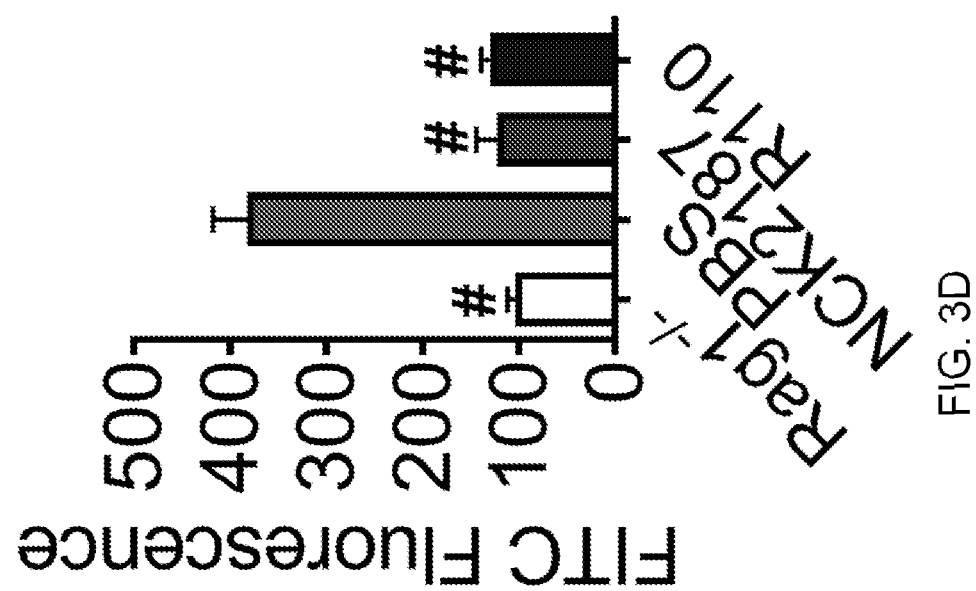

IBD patients display several defects in the many specialized components of the mucosal barrier, from the mucus layer composition to the adhesion molecules that regulate paracellular permeability [10]. At the end of eight weeks, four mice on each group were fed with FITC-dextran and euthanized four-hour post-gavage to collect serum for detection of gut permeability by FITC dextran (FIG. 3B). Feces at the eight weeks post-treatment were also tested for serum albumin levels to confirm gut permeability findings (FIG. 3C). The results showed that oral delivery of R110 significantly mitigated gut barrier leakage, as demonstrated by reduced FITC-dextran in the circulation and lower level of albumin in the feces. NCK2187 also reduced FITC-dextran levels and albumin but at a lower magnitude than R110, demonstrating once again the R110 is superior in protecting mice from IBD. Inflammation and increase permeability also led to blood oozing in the feces, which was detected by measuring hemoglobin in feces using fecal occult blood (FOB) detection kit (FIG. 3D). The data showed that R110 significantly reduced the FOB compared to the untreated mice, or mice treated with PBS or NCK2187 ($p<0.05$).

Example 5—R110 Induces Positive Changes in the Transciptome of Colon Tissue

Figure 4:
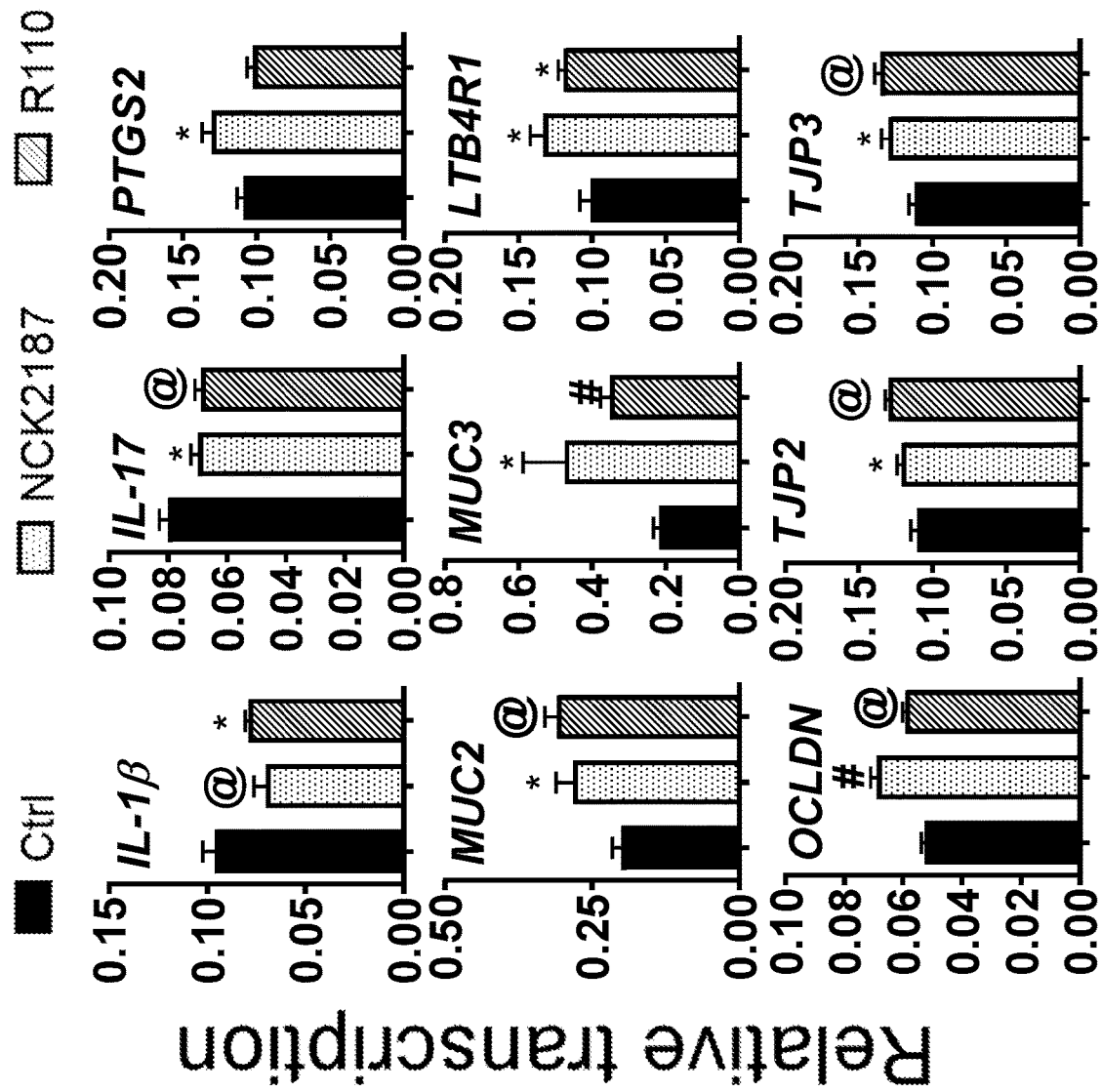
FIG. 4: SlpA reduces local inflammation and leaky gut. Total RNA was isolated from the distal colon of mice from Rag1-deficient mice after eight weeks of T cell-mediated colitis initiation. Mice without colitis were used as a reference. Relative changes in transcripts were tested for IL-1β, IL-17, PTGS2, MUC2, MUC3, LTB4R1, OCLDN, TJP2, TJP3. Results represent mean±SEMs from three independent experiments. *$P<0.05$, @$P<0.01$, #$P<0.001$.

We next assessed changes at the transcriptomic level. Two mm long distal colon pieces were excised, and total RNA was isolated and converted to cDNA for detection of target genes (FIG. 4). Transcripts from inflammatory cytokines, such as IL-10 and IL-17, were significantly reduced in mice treated with R110 or NCK2187 than in the control group. The colon separates host tissue from the gut microbiota by the presence of mucins. The major mucins present in the colorectal area are mucin 1 (Muc1), mucin 2 (Muc2), mucin 3 (Muc3), and mucin 4 (Muc4). Out of these four mucins, Muc2 and Muc3 have been shown to play a significant role in a healthy colon [26-28]. In mice treated with SlpA-expressing bacteria (R110 or NCK2187), expression of Muc2 and Mfuc3 where significantly increased compared to the control. Occludin and tight junction proteins act as adhesives among the intestinal epithelial cells to aid in the barrier function. Also, in this case, occludin and tight junction proteins 2 and 3 levels were significantly elevated by SlpA treatment. Unexpectedly, we noticed several differences between R110 and NCK2187 in the magnitude of changes. We then noted a similar increase in LTB4R1 expression only in mice treated with SlpA-expressing bacteria. LTB4R1 is essential for IgA production in the gut and acts as a protective means for gut microbial homeostasis. Surprisingly, the gene for prostaglandin-endoperoxide synthase (PTGS), which is responsible for Cox2 enzyme expression was upregulated by NCK2187 but not by R110, denoting a big difference in the mechanism of action of these two bacteria. Overall, these data corroborate the protective role of SlpA in diminishing inflammation and restoring gut barrier integrity, and further support the unexpected differential mechanism of protection conferred by R110 and NCK2187. Hence, protein secretion (R110) and not solely membrane expression (NCK2187) is key in mediating these effects.

Example 6—R110 Induces IL-10 and Reduces Rorγt and IL-17 Expression

Figure 5A:
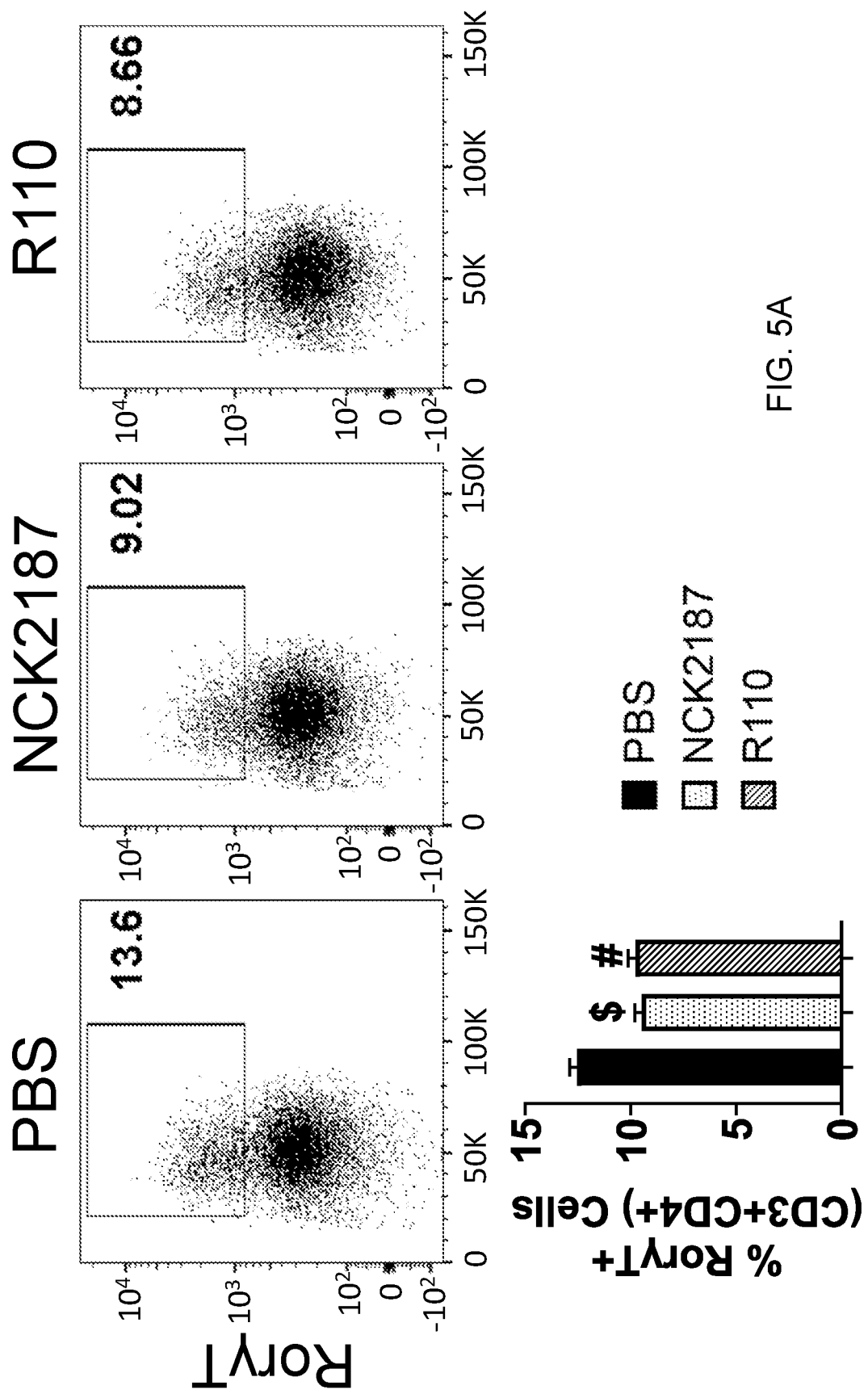
FIGS. 5A-5C: SlpA modifies T cell response in colitis mice. Colonic cells isolated and stained for RORγt (RORγT.
Figure 5B:
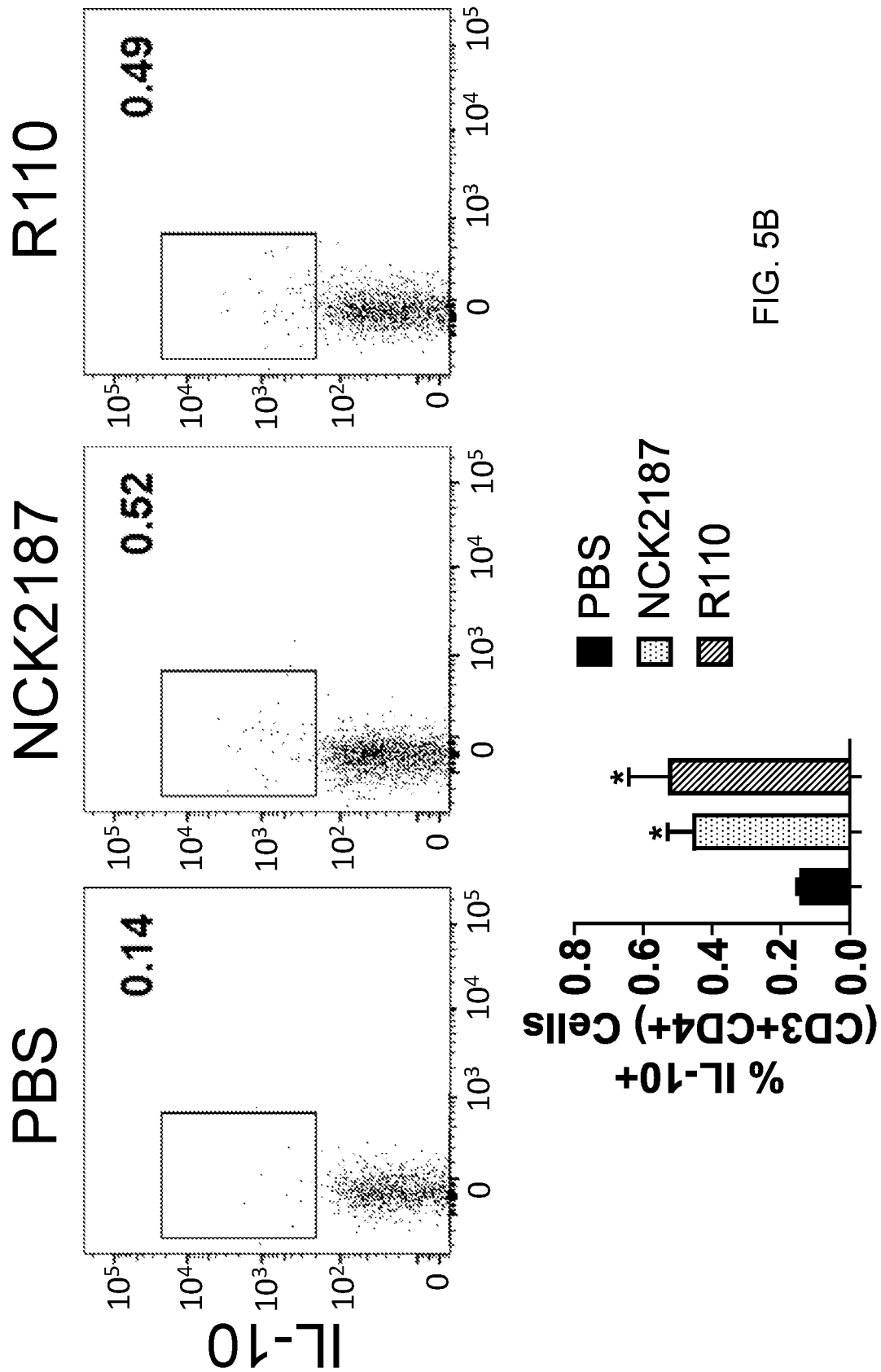
Figure 5C:
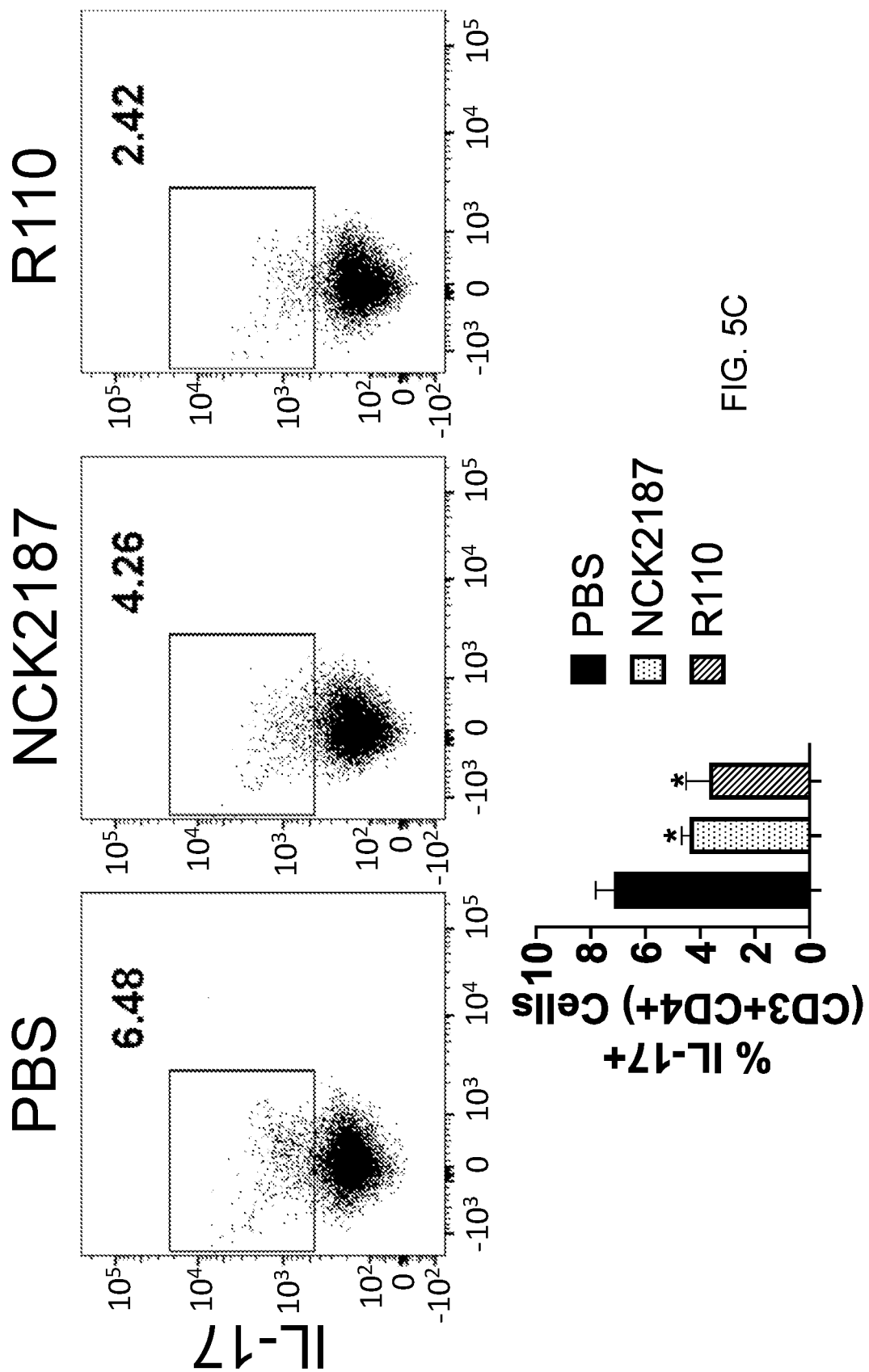

The transcriptomic changes suggest a role of SlpA in modulating the gut immune response. Therefore, we sought to understand the role of T cell in this model. Rag1-deficient mice were injected with one million CD45RB$^{hi}$ cells and then were treated with R110, NCK2187 or PBS once a week, as indicated before. Four weeks post-introduction of T cells, mice were euthanized to collect the colonic lamina propria cells. The isolated cells were selected for CD4+ and then stained for RORγt, IL-17, and IL-10 expression. CD4+ T cells isolated from mice treated NCK2187 or R110 showed a significant decrease in inflammatory RORγt and IL-17 producing T cells, and an increase in anti-inflammatory IL-10 producing T cells in the colonic lamina propria compared to control mice (FIG. 5), further supporting the ability of SlpA to engage the immune system leading to a diminution of inflammation.

Example 7—R110 Reduces Critical Inflammatory Cytokines in Sera of Diseased Mice

Figure 6:
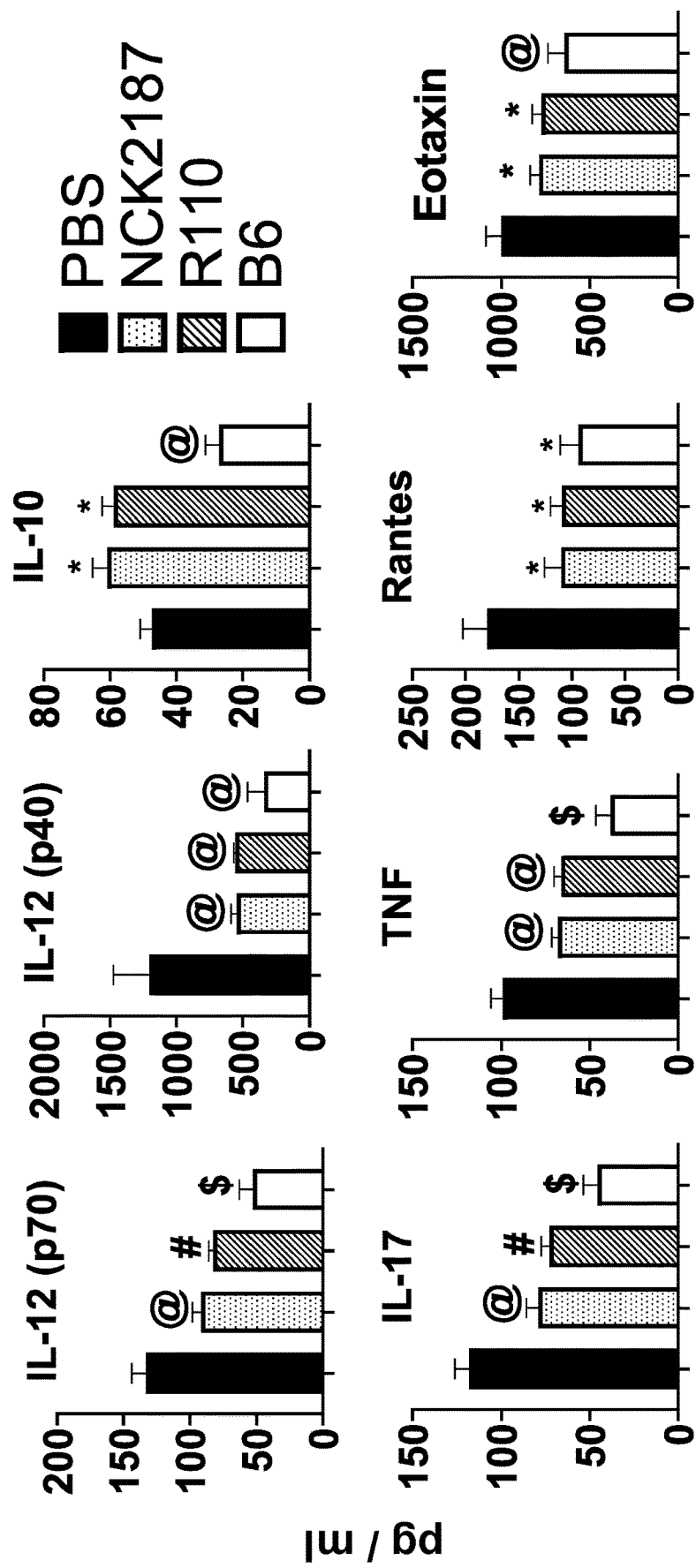
FIG. 6: SlpA engage the gut immune cell to reduce systemic inflammation. Serum collected from mice from Rag1-deficient mice after 8 weeks of T cell-mediated colitis initiation. Serum from mice without colitis was used as a reference. Results represent means SEMs from three independent experiments. *$P<0.05$, @$P<0.01$, #$P<0.001$, $$P<0.0001$.

To test whether R110 also reduces systemic proinflammatory cytokines, mice were euthanized after four weeks post-introduction of naïve T cells. The serum was tested for 23 cytokines (Eotaxin, G-CSF, GM-CSF, IFN-γ, IL-1α, IL-1β, IL-2, IL-3, IL-4, IL-5, IL-6, IL-9, IL-10, IL-12 (p40), IL-12 (p70), IL-13, IL-17A, KC, MCP-1, MIP-1α, MIP-1β, RANTES, TNF-α). The results showed that treatment with SlpA expressing bacteria significantly reduced the levels of proinflammatory cytokines (IL-12 (p70), IL-12 (p40), IL-17, TNF, Eotaxin and RANTES) and increased levels of IL-10 (FIG. 6).

Example 8—Differential Protection of the Gut Microbiota by R110 and NCK2187

Figure 7A:
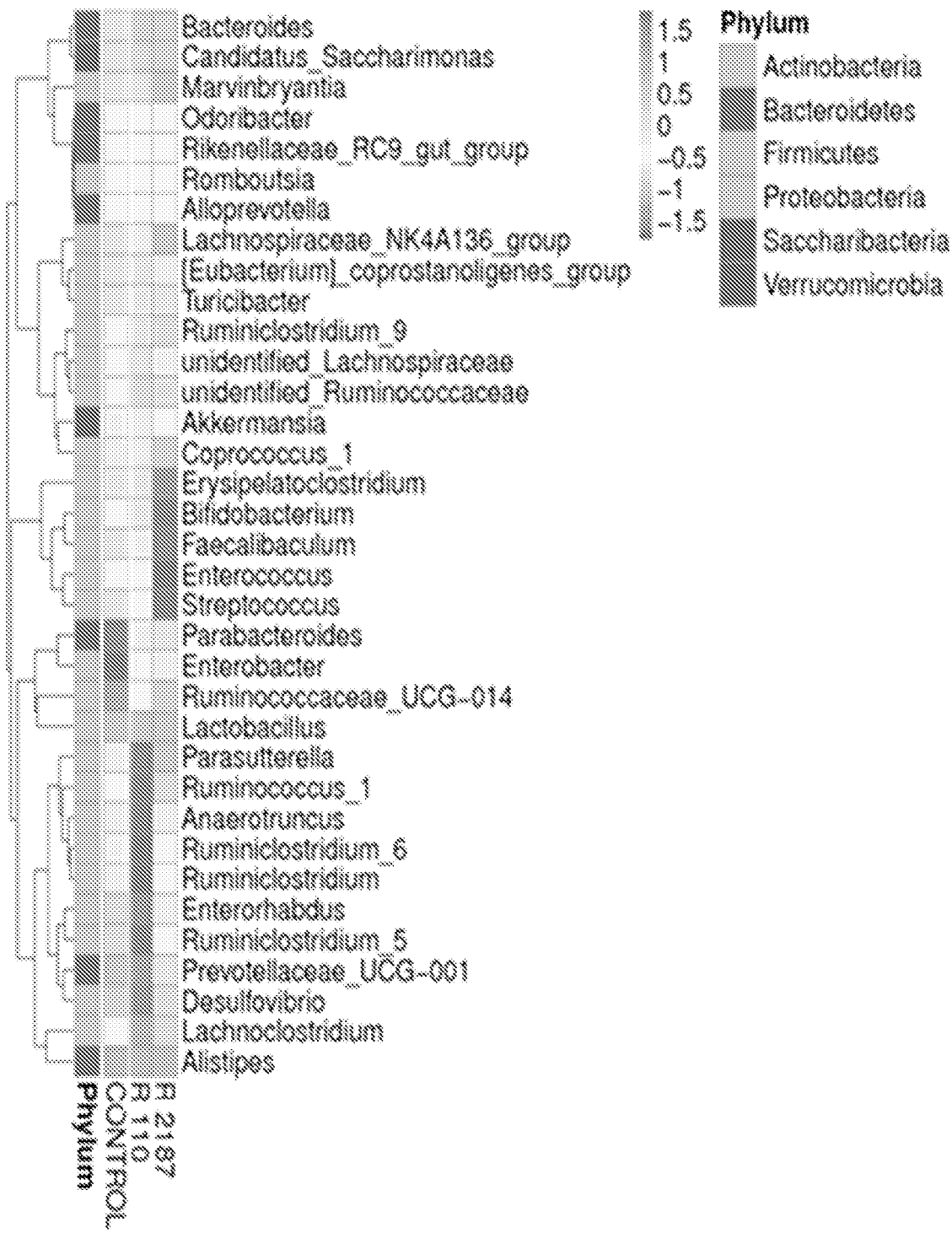
FIGS. 7A-7C: Protection of the gut microbiome by SlpA. Fecal DNA was isolated from Rag1-deficient mice after four weeks of T cell-mediated colitis initiation. Amplicons were generated using specific primers (R110 Forward: AATGCAACCATAACTGCCGC (SEQ ID NO: 18) and Reverse: TGTTGCGCCTGAGGTAACAT (SEQ ID NO: 19); NCK2187 Forward: CCAGCTATTGCCGGTAACCTT (SEQ ID NO: 20) and Reverse: AACGGCAGTAGTGC-TACCAG (SEQ ID NO: 21)) for SlpA gene. The amplicon was sequenced using Illumina high throughput sequencer with a paired-end sequencing strategy.
Figure 7B:
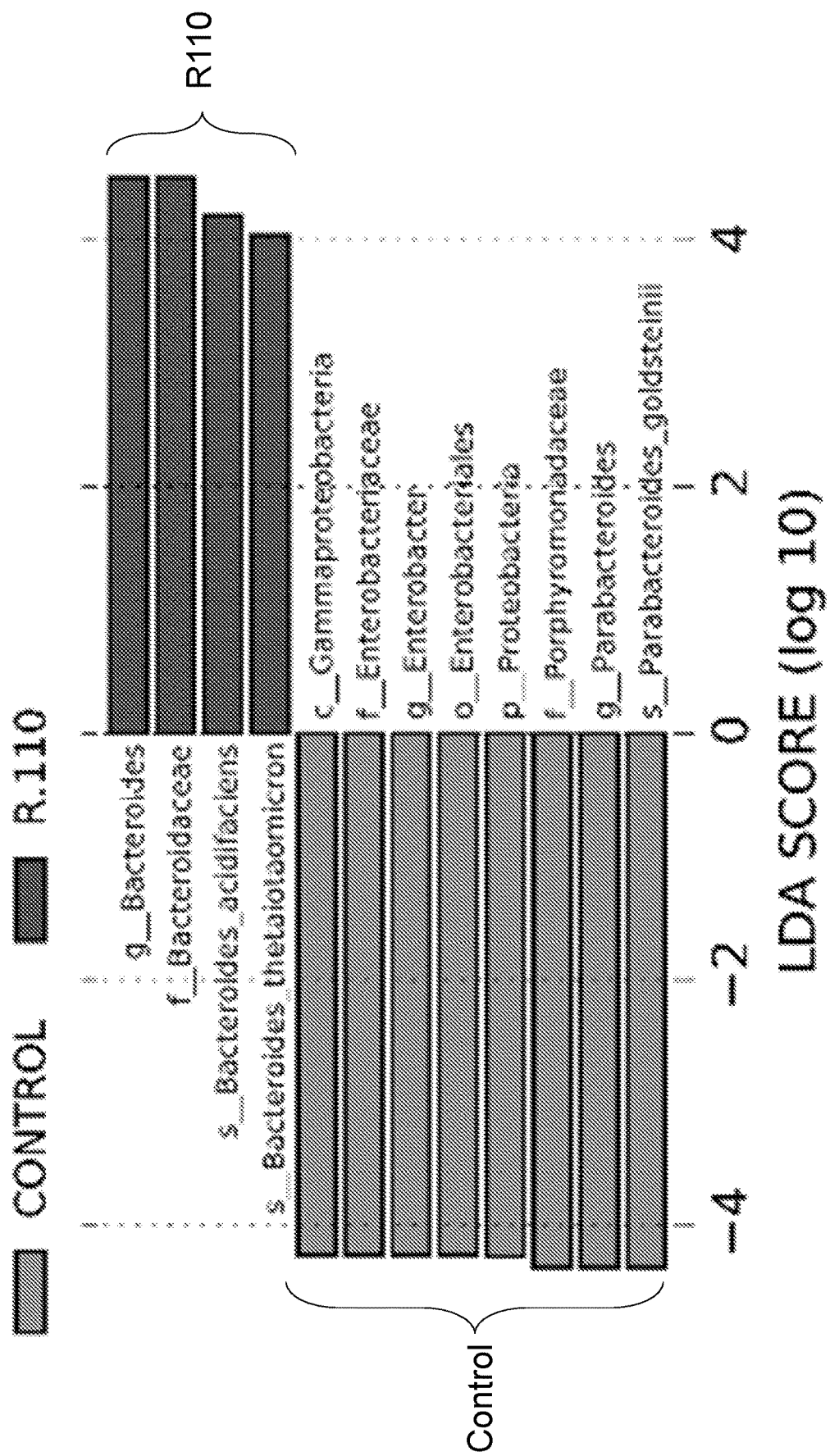
Figure 7C:
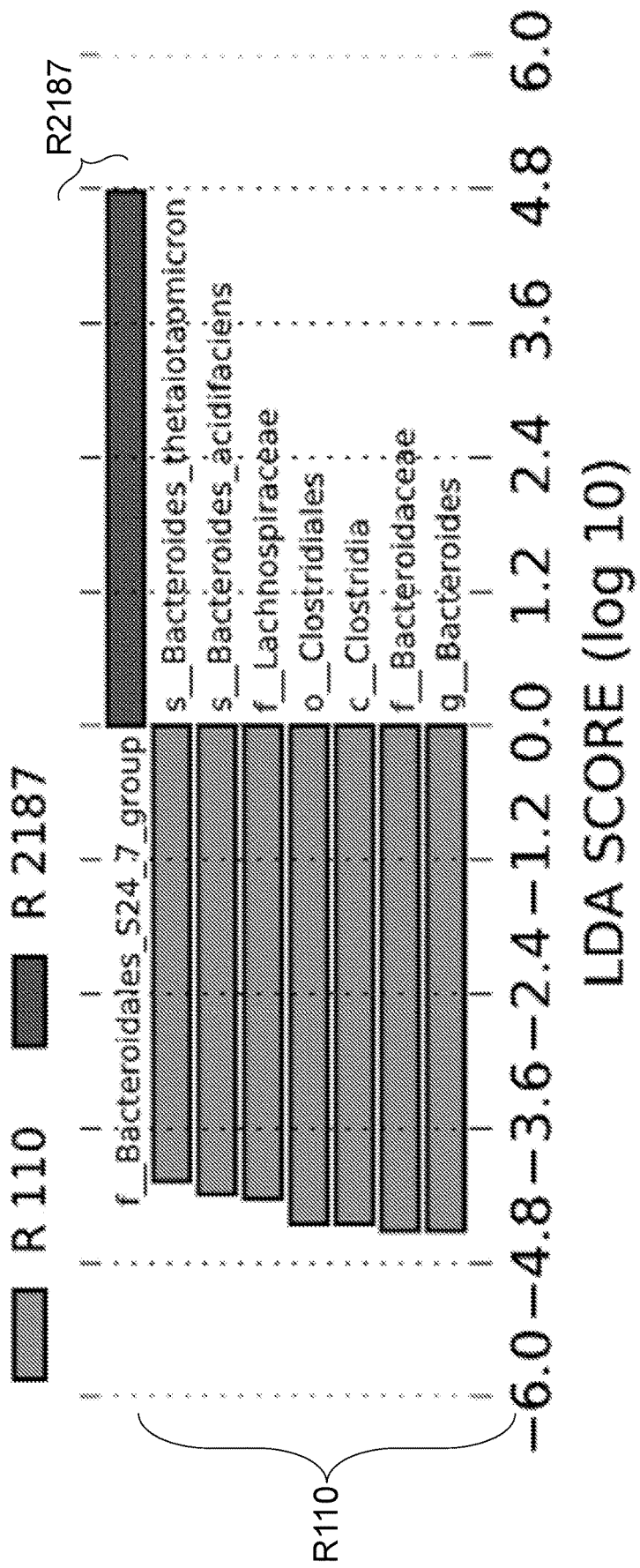

Microbiota harboring the gut plays a critical role in health and disease. We collected feces from colitis mice that were treated with R110, NCK2187, or PBS with daily oral administration for a month. Total DNA was isolated and the V3-V4 region of the bacterial DNA was sequenced using amplicon sequencing. As expected, the results showed a decreased in bacteria relative abundance in control mice, which was mitigated by R110 or NCK2187 administration, suggesting a protection of the gut microbiome richness by SlpA (FIG. 7). In addition, administration of SlpA-expressing bacteria favored taxa that are associated with gut health. The most significant changes were found in six major phyla, Actinobacteria, Bacteroidetes, Firmicutes, Proteobacteria, Saccharibacteria and Verrucomicrobia. Surprisingly, given that both bacteria belong to the Lactic acid group, R110 and NCK2187 differentially protected the gut microbiome. Mice treated with R110 enriched bacteria belonging to family *Parasutterella, Ruminicoccus, Anaerotruncus, Ruminiclostridium, Enterorhabdus, Prevotellaceae, Desulfovibrio,* and *Lachnoclostridium*. On the other hand, NCK2187 fed mice showed an increase in Erysipelatoclostridium, *Bifidobacterium, Enterococcus,* and *Streptococcus* (FIG. 7A). At a species level, a linear dimensional analysis (LDA) revealed that R110 fed mice were enriched in two bacterial species, *Bacteroides acidifaciens* and *Bacteroides thetaiotamicron* (FIG. 7B), whereas NCK2187 fed mice showed an increase in bacteria from Bacteroidales S24-7 group (FIG. 7C). This result once again demonstrates the significant difference between R110 and NCK2187, which are the base of the superior protection of R110.

Example 9—R110 Induces Regulatory Cytokines in Human Dendritic Cells

Figures 8A, 8B:
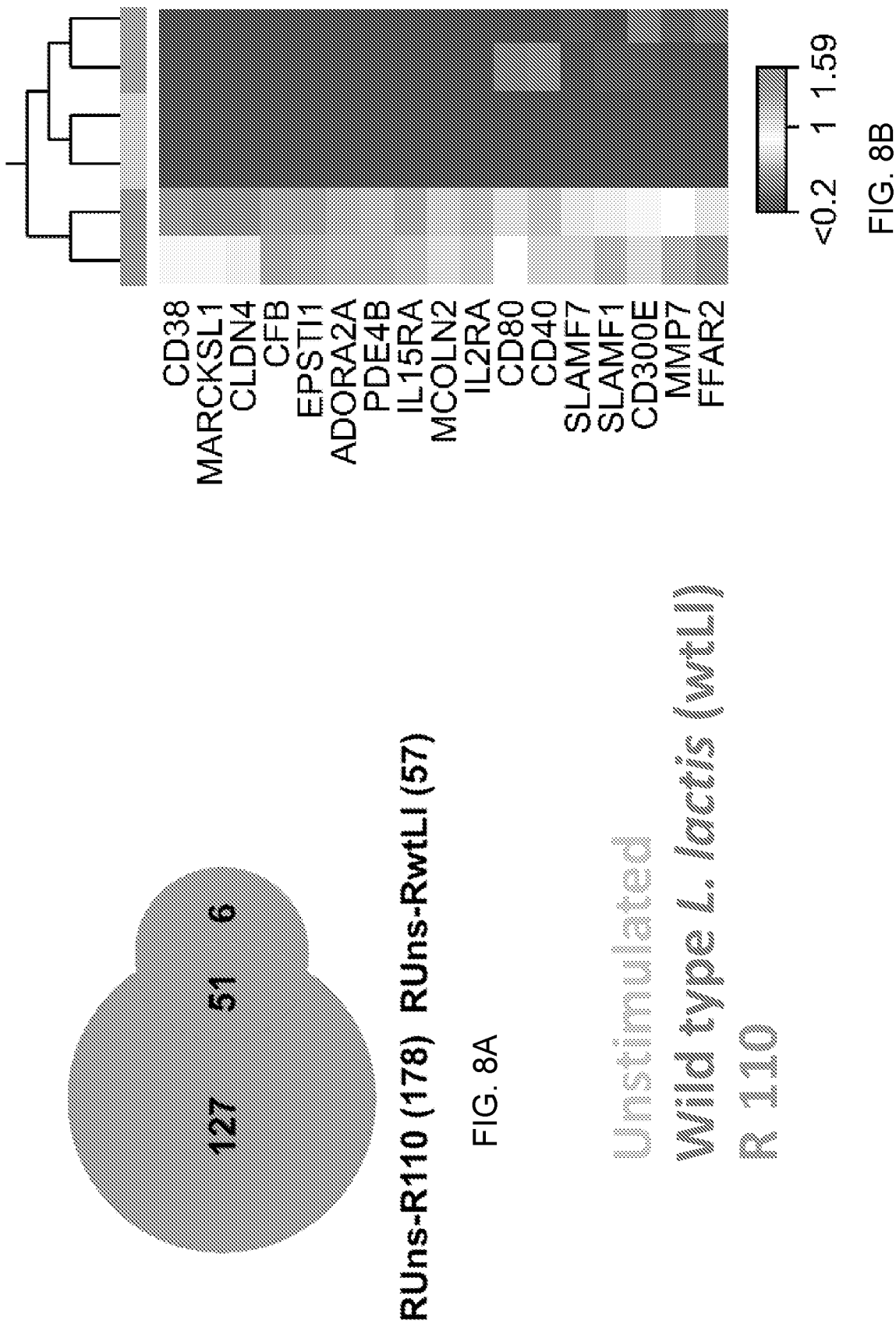
FIGS. 8A-8E: SlpA engages human dendritic cells (DC) to trigger differential gene expression. Human dendritic cells were stimulated with R110, WT *Lactococcus lactis* at a 1:1 ratio, or left unstimulated. Total isolated RNA was sequenced using Novaseq (Illumina, San Diego, CA) at a commercial site. The transcriptomic data were analyzed using CLC genomic workbench V 20 (Qiagen, Hilden, Germany). Differential expression genes were determined with a selection threshold of P-value ≤0.05 and log 2-fold change ≥1. Duplicate samples were used for each condition.
Figures 8C, 8D:
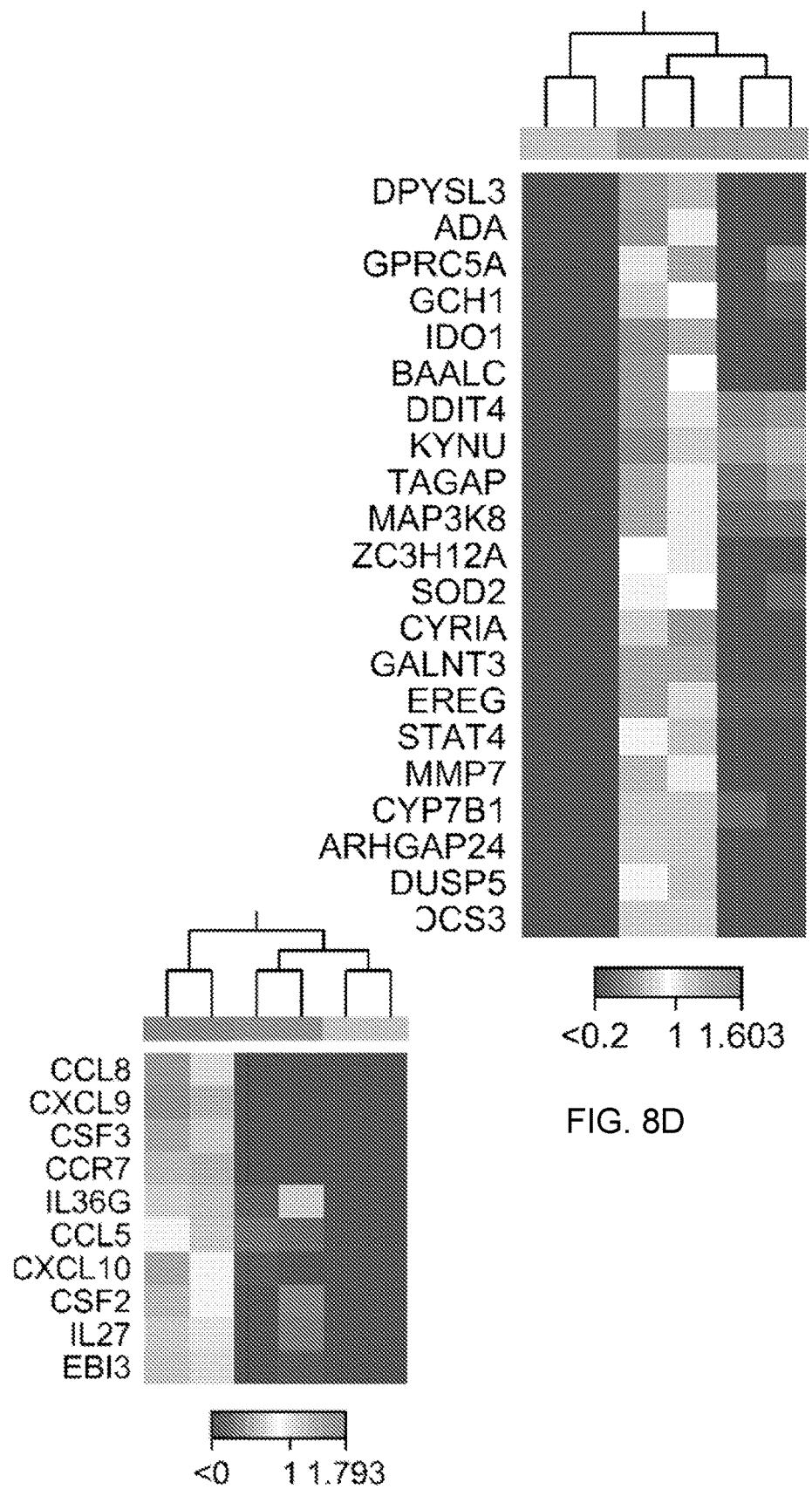
Figure 8E:
Figure 13A:
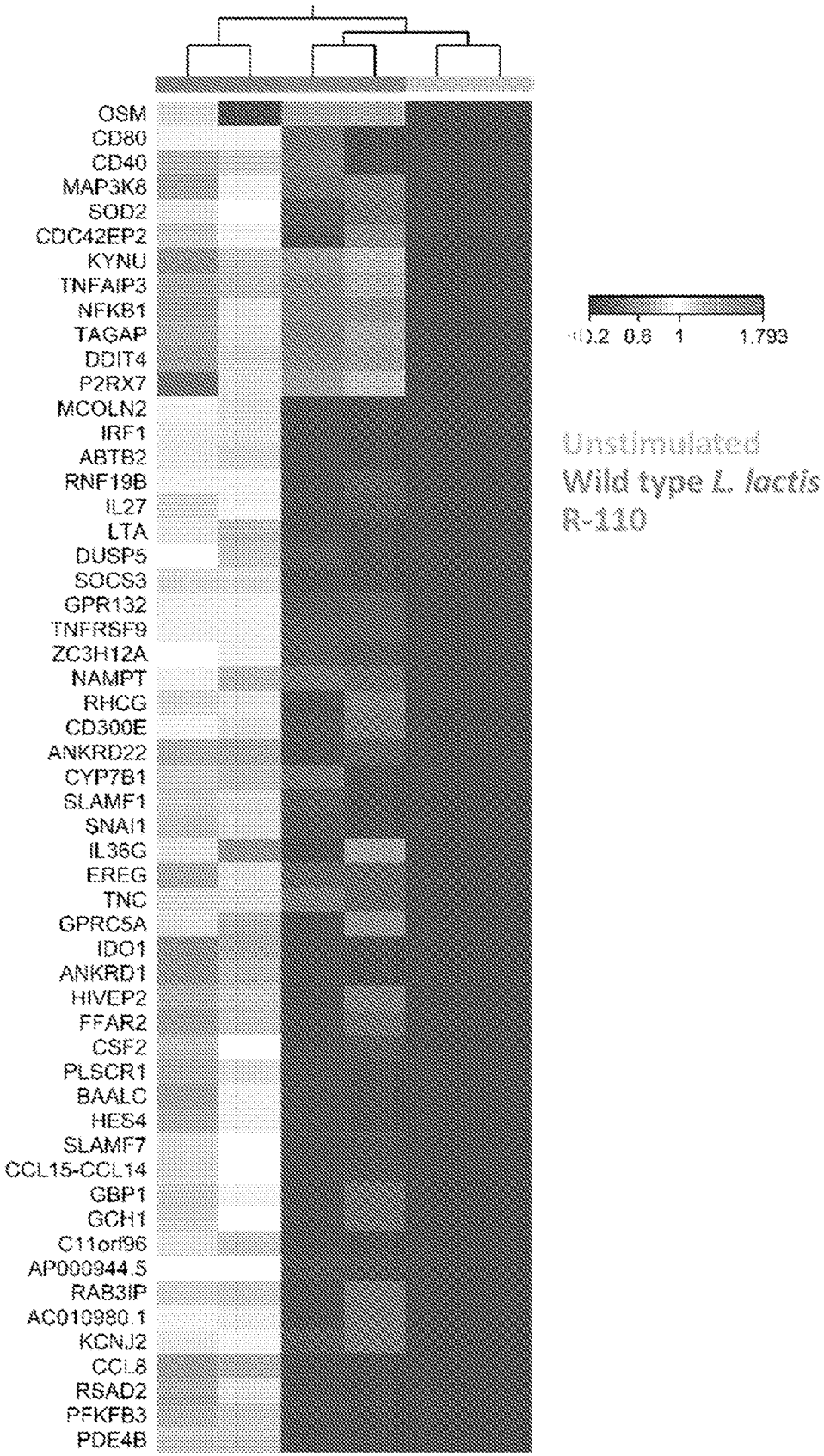
FIGS. 13A-13B: Human dendritic cells were stimulated with R110, WT *Lactococcus lactis* lines at a 1:1 ratio, or left unstimulated. Total isolated RNA was sequenced using Novaseq at a commercial site. The transcriptomic data were analyzed using CLC genomic workbench V 20.
Figures 13A, 13B:
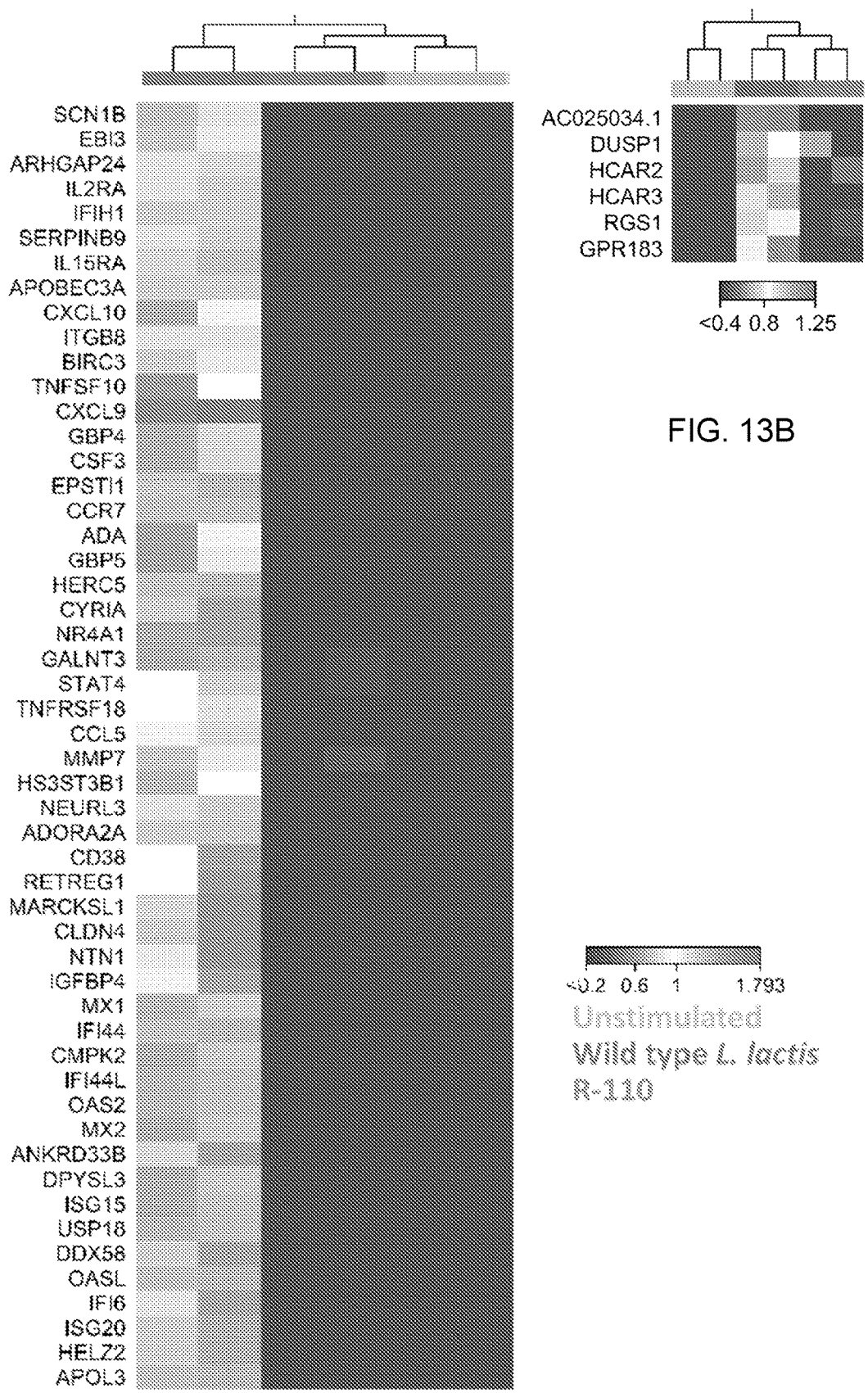

SlpA has shown incredible efficacy to treat colitis in mice. To confirm its activity in humans, we cocultured human monocyte-derived dendritic cells with the WT *L. lactis* strain or R110 at the MOI of 1 for 12 hours. Total RNA was isolated from these samples and sent for the entire exome RNA sequencing. The three groups (unstimulated, stimulated with WT or R110) were compared against each other and among themselves. WT *L. lactis* stimulated a total of 57 genes in dendritic cells, whereas R110 stimulated 178 genes; 51 genes were common, which are the genes stimulated by *Lactococcus* (FIG. 8A and FIG. 13A). Six genes were only stimulated by the WT strain but not by R110 (FIG. 13B). The 127 genes that were specifically stimulated by the R110 included 74 coding genes and 53 noncoding genes. The 74 genes were grouped in four primary categories: cell surface receptors (CD38, CD40, CD80, IL-15RA, IL-2RA, CD300e, CCR7, FFAR2); cytokine (IL-27, IL36γ, EBi3, CSF, GM-CSF, and LTA) and chemokines (CCL8, CXCL9, CCL5, CXCL10); enzymes (ADA, SOCS3, SOD2KYNU, IDO1, etc.) and antiviral genes (IRF1, IFI44, IFI44L, OSA2, OSAL, ISG15, MX1, APOBEC3A, GBP4, GBP5, etc.). We also observed an increase in 18 noncoding RNAs, which may have a broader impact on dendritic cell behavior. The wild-type *L. lactis* induced 6 genes, AC025034.1, DUSP1, HCAR2, HCAR3, RGS1 and GPR183. The expression of some of these genes was confirmed by real time PCR (data not shown).

Example 10—R110 Induces IL-27 in Murine Dendritic Cells

Figure 10B:
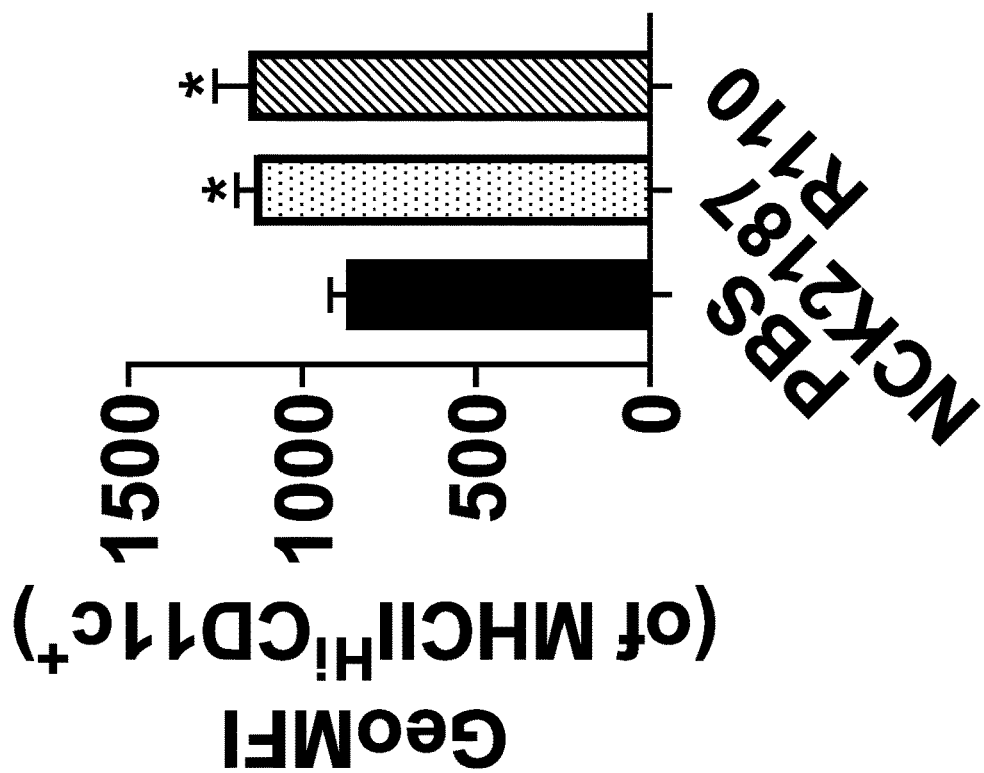
Figure 10A:
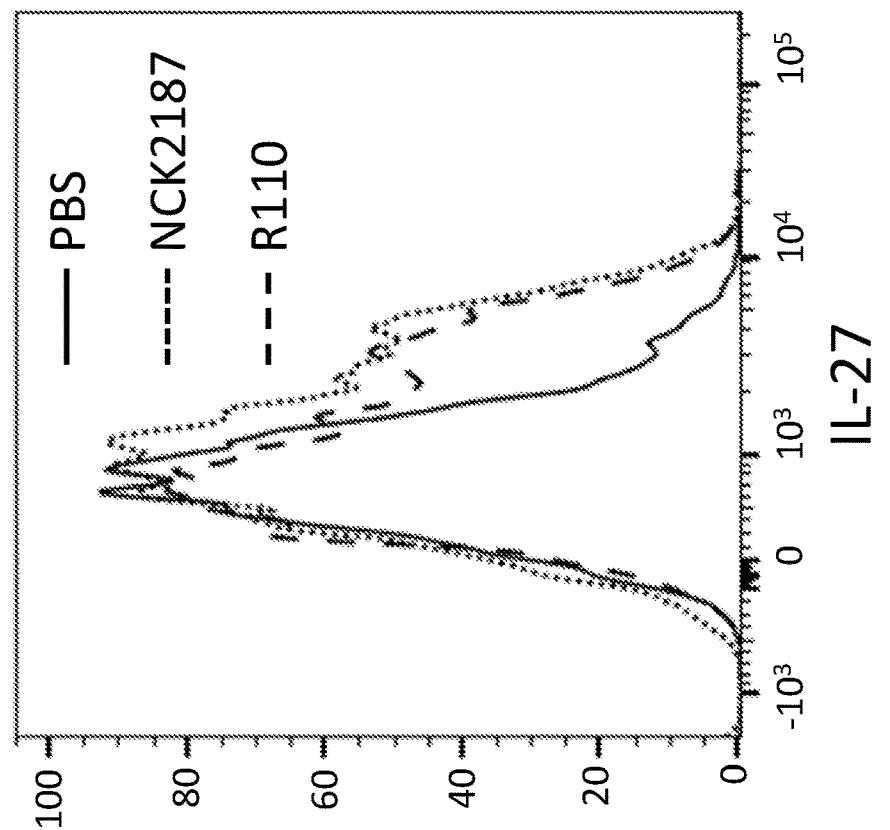

We further evaluated the transcription of IL-27 in bone marrow derived dendritic cells in response to the SlpA. Murine dendritic cells were generated from the isolated bone marrow cells and exposed with the isolated SlpA with increasing concentration. Total RNA was isolated from the dendritic cells after 12 h post incubation and subjected to quantitative real time PCR using GAPDH as an internal control. We observed a dose-dependent increase in IL-27 transcript in the cells exposed to SlpA (FIG. 9A). To know the kinetics of IL-27 transcription, we repeated the experiment using the highest concentration (1000 ng/ml). The data showed maximum accumulated transcripts were found in 12 h post exposure; however, we can detect IL-27 transcripts in 4 h post incubation as well (FIG. 9B). To observe the increase in SlpA-mediated IL-27, we gavaged R110 and NCK2187 to colitis induced mice as earlier for four weeks. Later, mice were euthanized and colonic cells were stained for IL-27 expressing dendritic cells (CD45$^+$CD11c$^+$MHCII$^{Hi}$) using flow cytometry. We detected colonic dendritic cells in mice fed with R110 express more IL-27 (FIGS. 10A and 10B). The heterodimeric receptor for IL-27 (IL-27R) is expressed on variety of cells including T cells. In the same experiment, we also evaluated cMAF, a transcription factor that are expressed upon the IL-27 signaling and controls behavior of T cells by, suppressing Th17 and augmenting Tregs and IL-10 production. In mice fed with NCK2187 or R110, presence of cMAF on the T cells was increased (FIGS. 10C and 10D), suggesting IL-27R signaling on these cells.

Example 11—Oral Administration of R110 Reduces Neutrophilia in the Lung

Patients with viral-induced ARDS present a hyperactivated immune response characterized by cytokine storm, reduction of regulatory T cells, and increased neutrophil levels both systemically and in the lung. Clearly patients that develop ARDS after viral infection lack fundamental immune regulatory mechanisms that contribute to misdirected hyperinflammation.

Figure 14:
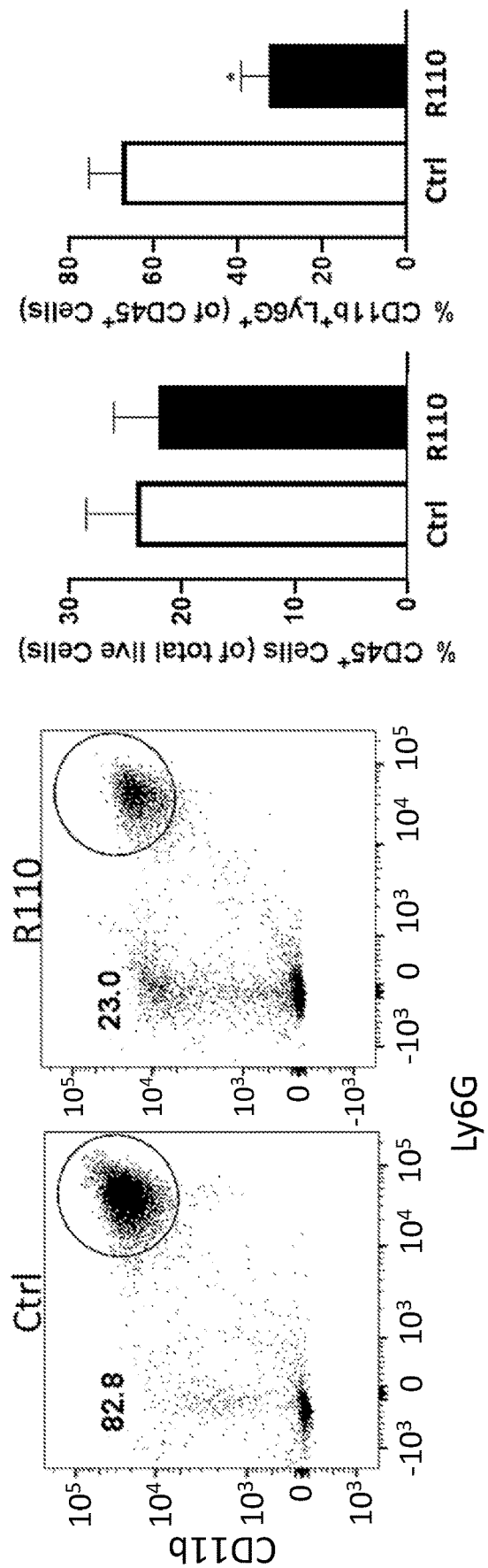
FIG. 14. Oral administration of R110 reduces neutrophilia in the lung. C57B/6 mice were gavaged with 1×10$^9$ CFU of R110 four times every third day. Two days post last gavage, LPS (5 ng/g) was instilled intranasally. Four hours later mice were euthanized to collect the lungs after flushing the circulating blood. Lungs were digested and stained with antibodies against murine CD45, CD11b and Ly6G. 1×10$^6$ cells were analyzed on BD Fortessa and data were generated using FlowJo.

We employed a murine acute lung injury model, in which ARDS is triggered by intranasal administration of LPS. Mice were orally administered $1 \times 10^9$ CFU of R110 every third day (four times total) prior to LPS challenge. A group of mice were used as control. Two days after the last gavage, mice received intranasal administration of LPS. Four hours later mice were euthanized, and the lungs were collected and used to assess neutrophil infiltration by flow cytometry. Results are displayed in FIG. 14. Unexpectedly, oral administration of R110 significantly diminished LPS-induced neutrophil count in the lung compared to controls.

These results confirm that targeting the gut microbiome DC can lead to systemic rebalancing of immune responses. Oral administration of RHO engages intestinal DCs to diminish inflammation and rebalance the overall immune response, not only locally in the gut, but also systemically, reaching the lung. Hence, modulation of the immune repertoire by engaging the host-microbiome immune interaction in the gut with R110 represents a novel strategy to mitigate ARDS severity.

Example 12

Figure 15:
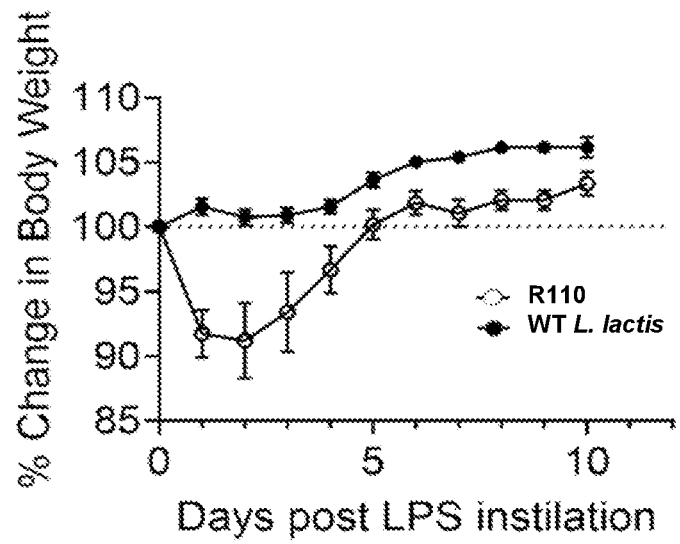
FIG. 15. R110 mitigates disease severity in a lung injury murine model. C57BL/6 mice received daily doses of R110 or the WT *L. lactis* at 1×10$^9$ CFU. Mice weight was recorded daily for 10 days post LPS challenge.

We employed a murine model of acute lung inflammation, in which lung injury is triggered by intranasal administration of LPS to test protraction of oral R110. In the first set of experiments, C57BL/6 mice were gavaged with R110 or WT *L. lactis* as control at $1 \times 10^9$ CFU/dose. Mice were dosed daily starting at four days before LPS challenge and continued for entire length of the study, which was 10 days. LPS was administered by intranasal administration at dose of 3.75 µg/g mouse. Upon LPS challenge, there was a significant weight loss in mice treated with the WT control strain. In contrast, oral administration of R110 rescued this phenotype and weight loss did not occur (FIG. 15).

Figure 16A:
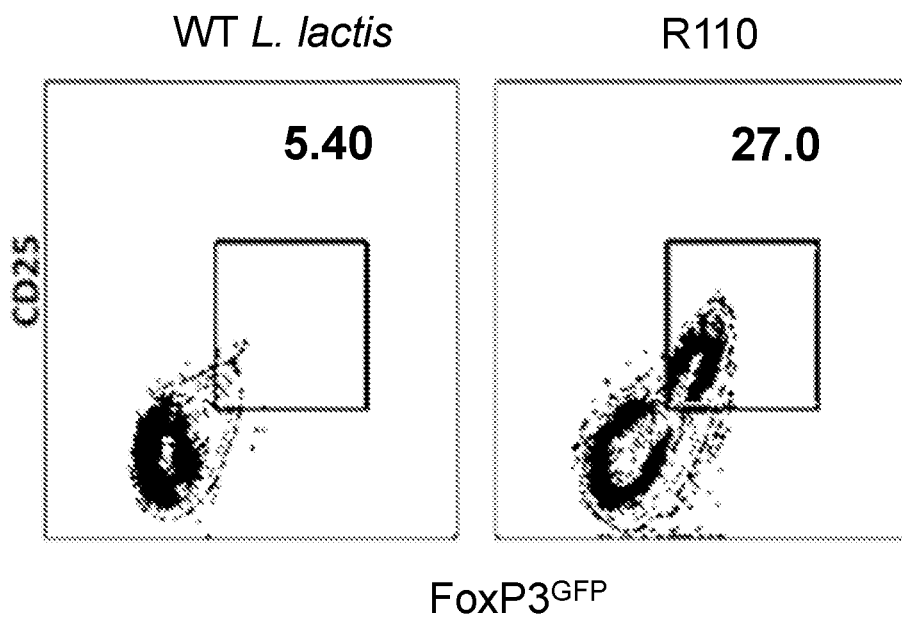
FIGS. 16A-16C. R110 works by modulating the immune response and restores airway epithelial barrier integrity.
Figure 16B:
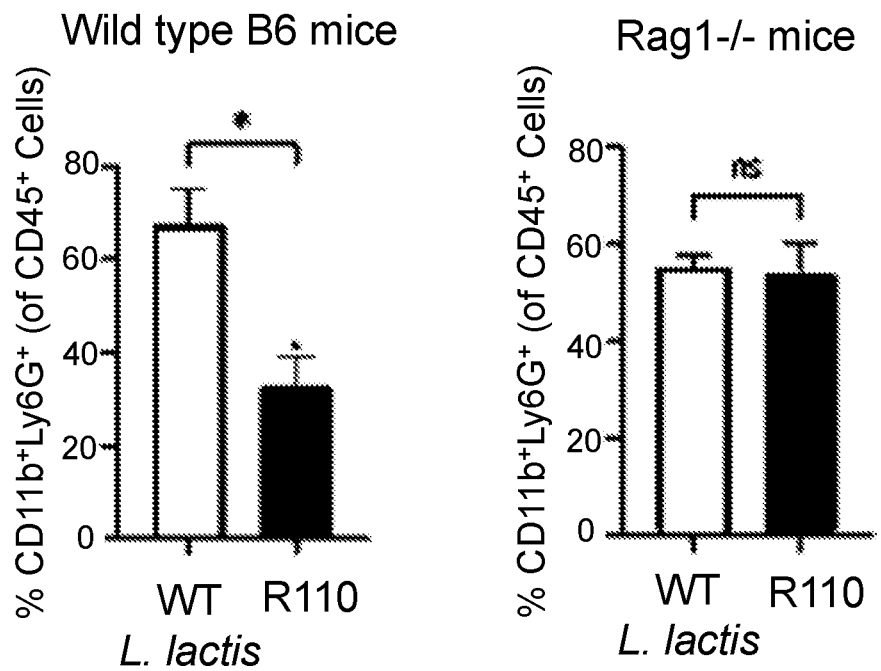
Figure 16C:
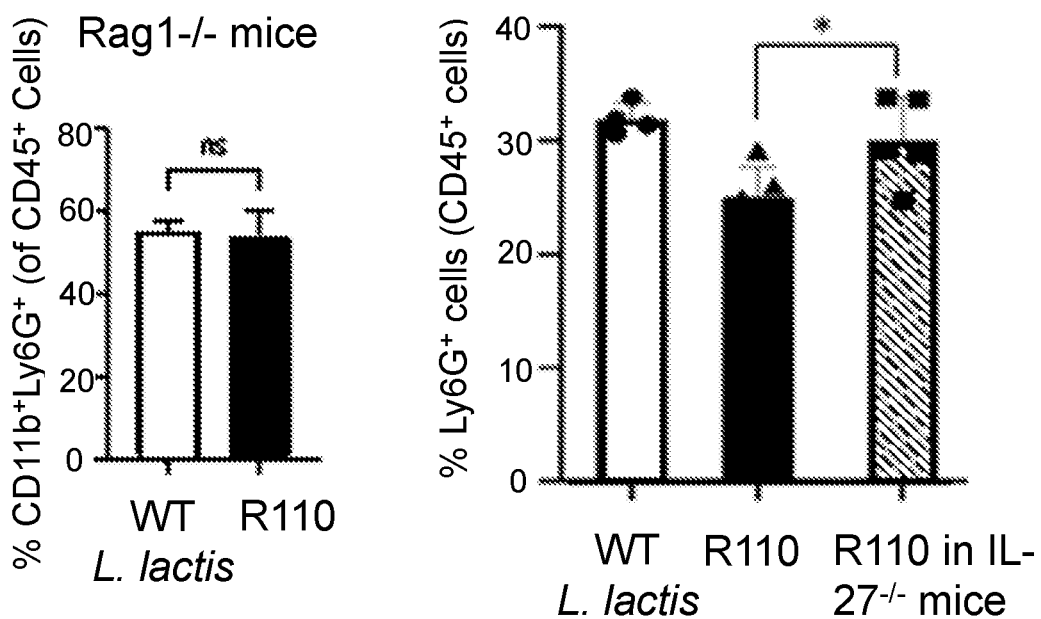

Example 13 Protection of Oral R110 was Tested in an Acute Murine Lung Injury Model C57BL/6 mice were orally administered with $1 \times 10^9$ CFU of R110 every third day (four times total) prior to LPS challenge. A group of mice were used as control and received the WT *L. lactis*. Two days post last gavage, mice received intranasal administration of LPS (5 ng/g of body weight). Four hours later mice were euthanized, lung collected and used to assess neutrophil infiltration and Tregs by flow cytometry. Results are displayed in FIGS. 16A-16C. Lung cellular analysis revealed that oral administration of R110 and not the WT strain significantly upregulated CD25$^+$FoxP3$^+$Treg in this acute lung injury model (FIG. 16A). LPS intranasal administration resulted in robust infiltration of CD11b$^+$Ly6G$^+$ neutrophils in the lung, which was significantly attenuated by oral R110 administration (FIG. 16B). The experiment above was repeated using Rag1$^{-/-}$ and IL-27$^{-/-}$ mice. Rag1$^{-/-}$ and IL-27$^{-/-}$ mice were orally administered with $1 \times 10^9$ CFU of R110 every third day (four times total) prior to LPS challenge. A group of mice were used as control and receive the WT *L. lactis*. Two days post last gavage, mice received intranasal administration of LPS (5 ng/g of body weight). Four hours later mice were euthanized, lung collected, and used to assess neutrophil infiltration by flow cytometry. As shown in FIG. 16B, R110 did not protect against neutrophil infiltration in the lung in Rag1$^{-/-}$ mice, suggesting that Treg induction mediated by R110 may play a role in protecting against inflammatory induction in the lung. Similarly, absence of IL-27 abrogated R110 efficacy, suggesting that R110 signals via IL-27 (FIG. 16C).

Example 14

Figure 17:
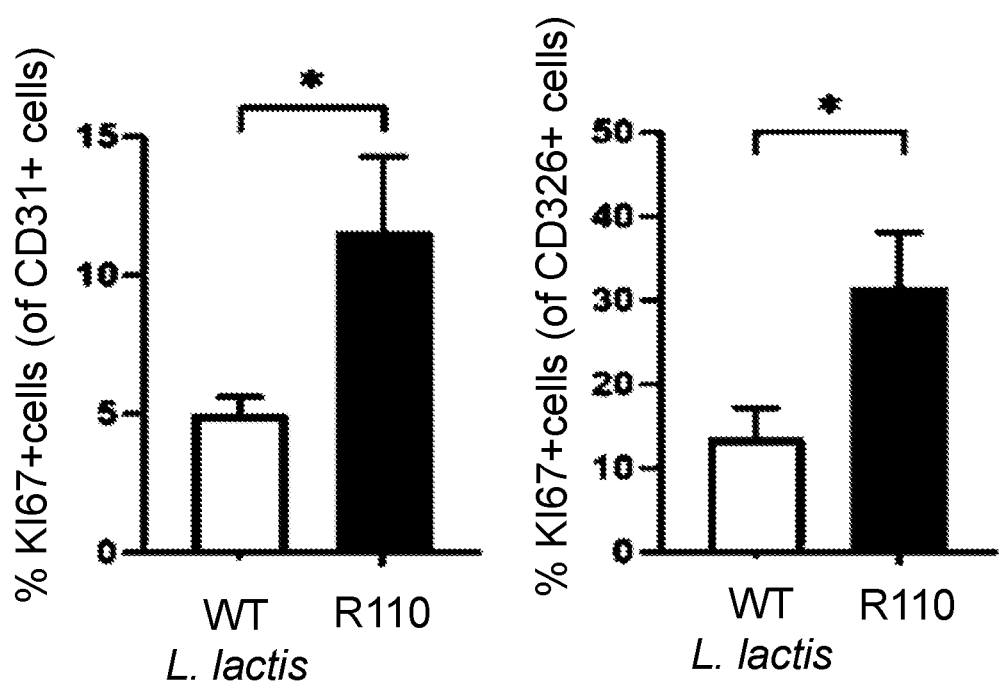
FIG. 17. R110 maintains the airway epithelial barrier. Using the LPS lung model as described above, lungs were harvested, and markers of epithelial proliferation were measured by qPCR. *P<0.05.

In the same animal model of acute lung inflammation, we investigated the ability of R110 to restore airways epithelial barrier integrity. C57BL/6 mice were orally administered with $1 \times 10^9$ CFU of R110 every third day (four times total) prior to LPS challenge. A group of mice were used as control and received the WT *L. lactis*. Two days post last gavage, mice received intranasal administration of LPS (5 ng/g of body weight). Four hours later mice were euthanized, lung collected and used to assess neutrophil infiltration and Tregs by flow cytometry. Oral administration of R110 but not the WT strain upregulated markers of epithelial proliferation, suggesting that R110 aids in maintaining a healthy lung epithelial barrier (FIG. 17).

Example 15

Figure 18B:
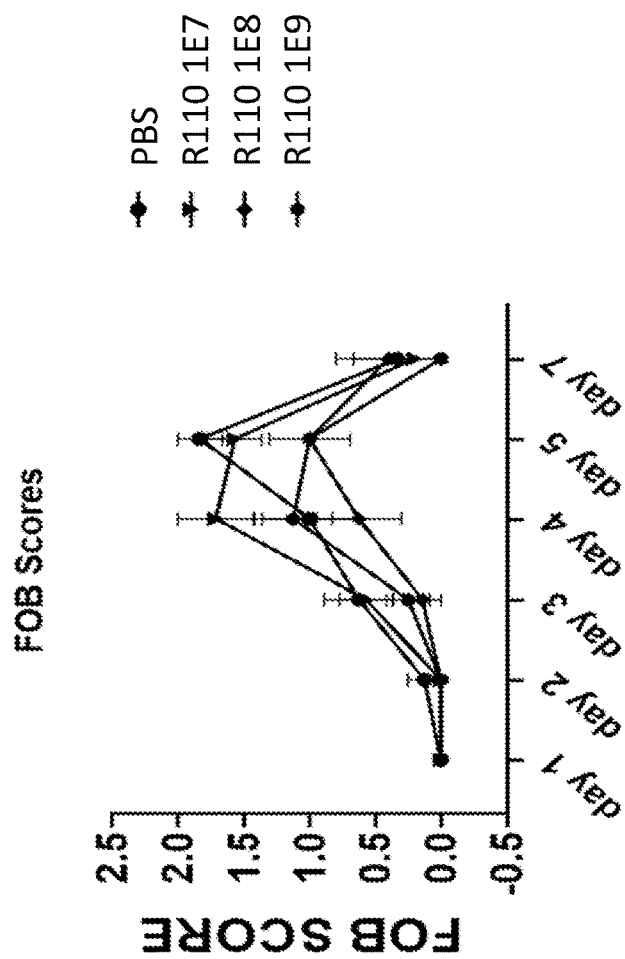
FIGS. 18A-18B. Oral administration of R110 protects mice from colitis. Colitis was induced in C57Bl/6 mice by 3% DSS added to the cage water from Day 0 to Day 4. R110 was orally dosed from Day -4 until the end of the study every other day Body weight (FIG. 18A) and fecal occult blood (FOB) were measured every day from Day 0 (FIG. 18B). *=p<0.05.
Figure 18A:
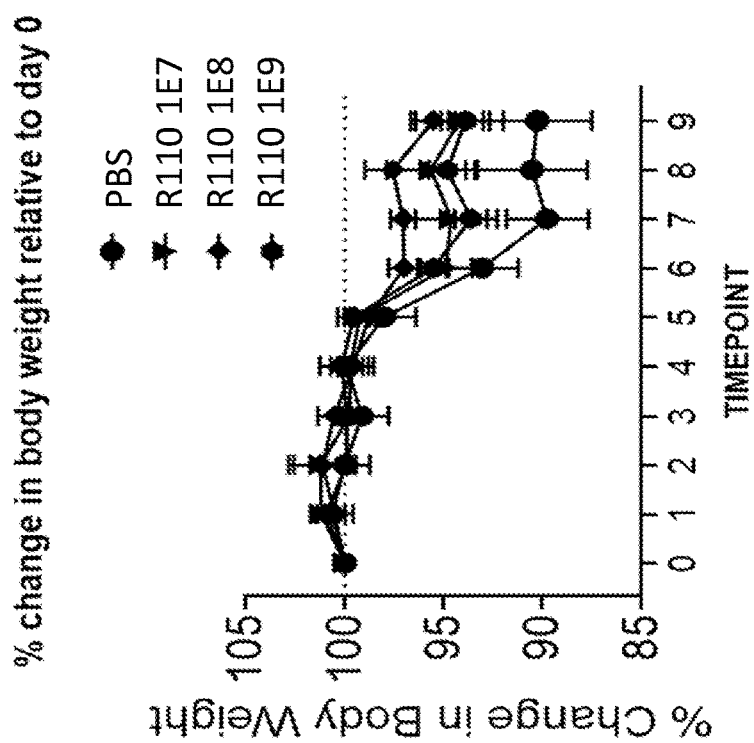
Figure 19:
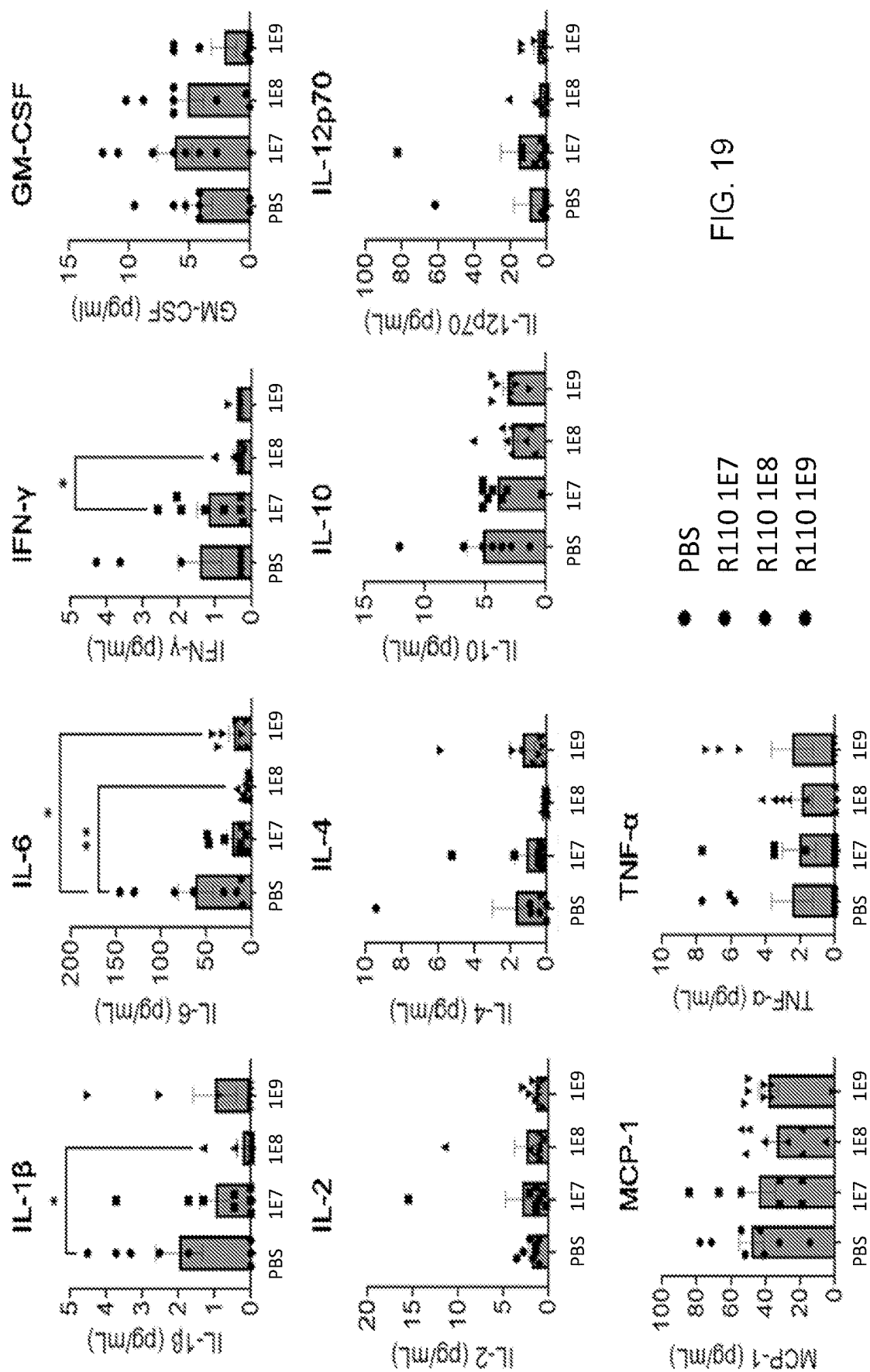
FIG. 19. Oral administration of R110 diminish systemic inflammation. Colitis was induced in C57Bl/6 mice by 3% DSS added to the cage water from Day 0 to Day 4. R110 was orally dosed from Day -4 until the end of the study every other day. Blood was collected from mice at Day 10 post DSS administration and analyzed for cytokine by multiplex ELISA. *=p<0.05; **=p<0.01.
Figure 20:
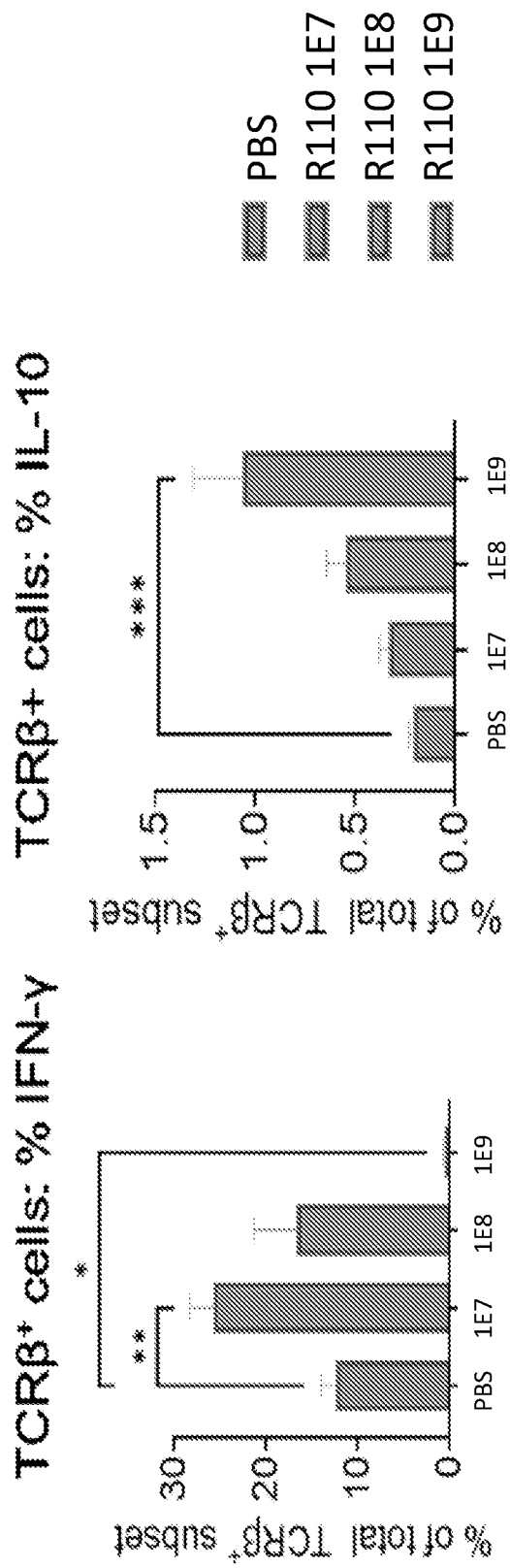
FIG. 20. Oral administration of R110 diminish colonic inflammation. Colitis was induced in C57Bl/6 mice by 3% DSS added to the cage water from Day 0 to Day 4. R110 was orally dosed from Day -4 until the end of the study every other day. Colonic tissues were collected from mice at Day 10 post DSS administration and T cells were analyzed by flow cytometry. *=p<0.05; **=p<0.01.
Figure 20:
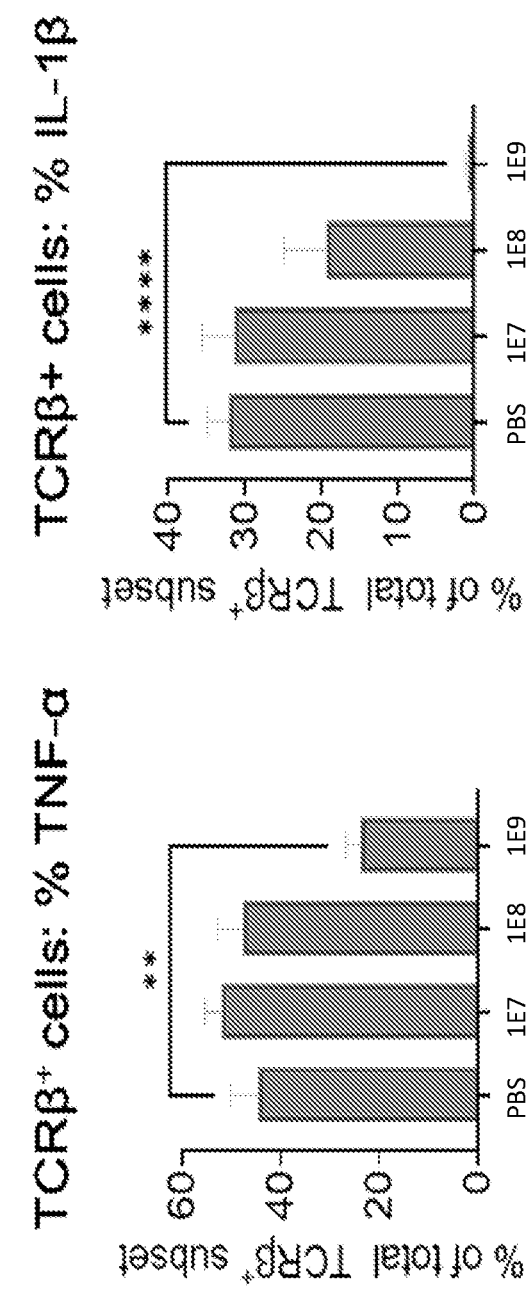

To assess R110 protection in intestinal inflammation, a DSS-induced colitis murine model was employed. C57Bl/6 mice were given 3% DSS in the drinking water for 5 days. On day 4 after clinical signs of IBD were evident, mice were orally gavaged with R110 (or PBS as control) every other day at doses of $1\times10^9$ CFU, $1\times10^8$ CFU, and $1\times10^7$ CFU. Body weight and fecal occult blood (FOB) score were measured daily. Mice were sacrificed on day 10, blood withdrew for immunophenotyping by flow cytometry, and serum used for cytokine evaluation. Dosing with R110 protected mice from weight loss compared to PBS treated mice (FIG. 18A). Similarly, R110 reduced FOB in mice with colitis (FIG. 18B). Systemic inflammation was also assessed in blood from mice at Day 10 and showed reduction of inflammatory cytokines in animal treated with R110 compared to controls (FIG. 19). Colonic tissues were harvested and used to assess T cell activation. Oral administration of R110 decreased pro-inflammatory T cells while upregulating anti-inflammatory T cells (FIG. 20).

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

1. Collaborators GBDIBD. The global, regional, and national burden of inflammatory bowel disease in 195 countries and territories, 1990-2017: a systematic analysis for the Global Burden of Disease Study 2017. Lancet Gastroenterol Hepatol. 2020; 5(1):17-30. Epub 2019/10/28. doi: 10.1016/52468-1253(19)30333-4. PubMed PMID: 31648971; PubMed Central PMCID: PMCPMC7026709.
2. Ye Y, Manne S, Treem W R, Bennett D. Prevalence of Inflammatory Bowel Disease in Pediatric and Adult Populations: Recent Estimates From Large National Databases in the United States, 2007-2016. Inflamm Bowel Dis. 2020; 26(4):619-25. Epub 2019/09/11. doi: 10.1093/ibd/izz182. PubMed PMID: 31504515.
3. Leirisalo-Repo M, Turunen U, Stenman S, Helenius P, Seppala K. High frequency of silent inflammatory bowel disease in spondylarthropathy. Arthritis Rheum. 1994; 37(1):23-31. Epub 1994/01/01. doi: 10.1002/art.1780370105. PubMed PMID: 8129761.
4. Di Jiang C, Raine T. IBD considerations in spondyloarthritis. Ther Adv Musculoskelet Dis. 2020; 12:1759720X20939410. Epub 2020/07/23. doi: 10.1177/1759720X20939410. PubMed PMID: 32695235; PubMed Central PMCID: PMCPMC7350041.
5. Fragoulis G E, Liava C, Daoussis D, Akriviadis E, Garyfallos A, Dimitroulas T.
   Inflammatory bowel diseases and spondyloarthropathies: From pathogenesis to treatment. World J Gastroenterol. 2019; 25(18):2162-76. Epub 2019/05/31. doi: 10.3748/wjg.v25.i18.2162. PubMed PMID: 31143068; PubMed Central PMCID: PMCPMC6526158.
6. Orchard T R, Wordsworth B P, Jewell D P. Peripheral arthropathies in inflammatory bowel disease: their articular distribution and natural history. Gut. 1998; 42(3):387-91. Epub 1998/05/13. doi: 10.1136/gut.42.3.387. PubMed PMID: 9577346; PubMed Central PMCID: PMCPMC1727027.
7. Bernstein C N, Benchimol E I, Bitton A, Murthy S K, Nguyen G C, Lee K, et al. The Impact of Inflammatory Bowel Disease in Canada 2018: Extra-intestinal Diseases in IBD. J Can Assoc Gastroenterol. 2019; 2 (Suppl 1):S73-S80. Epub 2019/07/12. doi: 10.1093/jcag/gwy053. PubMed PMID: 31294387; PubMed Central PMCID: PMCPMC6512250.
8. Pouillon L, Bossuyt P, Vanderstukken J, Moulin D, Netter P, Danese S, et al. Management of patients with inflammatory bowel disease and spondyloarthritis. Expert review of clinical pharmacology. 2017; 10(12):1363-74. Epub 2017/09/08. doi: 10.1080/17512433.2017.1377609. PubMed PMID: 28879780.
9. McDermott A J, Huffnagle G B. The microbiome and regulation of mucosal immunity. Immunology. 2014; 142 (1):24-31. Epub 2013/12/18. doi: 10.1111/imm.12231. PubMed PMID: 24329495; PubMed Central PMCID: PMCPMC3992044.
10. Glassner K L, Abraham B P, Quigley E M M. The microbiome and inflammatory bowel disease. The Journal of allergy and clinical immunology. 2020; 145(1):16-27. Epub 2020/01/09. doi: 10.1016/j.jaci.2019.11.003. PubMed PMID: 31910984.
11. DeFilipp Z, Bloom P P, Torres Soto M, Mansour M K, Sater M R A, Huntley M H, et al. Drug-Resistant *E. coli* Bacteremia Transmitted by Fecal Microbiota Transplant. N Engl J Med. 2019; 381(21):2043-50. Epub 2019/10/31. doi: 10.1056/NEJMoa1910437. PubMed PMID: 31665575.
12. Singh R, de Groot P F, Geerlings S E, Hodiamont C J, Belzer C, Berge I, et al. Fecal microbiota transplantation against intestinal colonization by extended spectrum beta-lactamase producing Enterobacteriaceae: a proof of principle study. BMC research notes. 2018; 11(1):190. Epub 2018/03/24. doi: 10.1186/s13104-018-3293-x. PubMed PMID: 29566738; PubMed Central PMCID: PMCPMC5863815.
13. Basso P J, Camara N O S, Sales-Campos H. Microbial-Based Therapies in the Treatment of Inflammatory Bowel Disease—An Overview of Human Studies. Front Pharmacol. 2018; 9:1571. Epub 2019/01/29. doi: 10.3389/fphar.2018.01571. PubMed PMID: 30687107; PubMed Central PMCID: PMCPMC6335320.
14. Rangan K J, Pedicord V A, Wang Y C, Kim B, Lu Y, Shaham S, et al. A secreted bacterial peptidoglycan hydrolase enhances tolerance to enteric pathogens. Science. 2016; 353(6306):1434-7. Epub 2016/10/07. doi: 10.1126/science.aaf3552. PubMed PMID: 27708039; PubMed Central PMCID: PMCPMC5158264.
15. Lightfoot Y L, Selle K, Yang T, Goh Y J, Sahay B, Zadeh M, et al. SIGNR3-dependent immune regulation by *Lactobacillus acidophilus* surface layer protein A in colitis. Embo J. 2015; 34(7):881-95. doi: 10.15252/embj.201490296. PubMed PMID: 25666591; PubMed Central PMCID: PMC4388597.
16. Konstantinov S R, Smidt H, de Vos W M, Bruijns S C, Singh S K, Valence F, et al. S layer protein A of *Lactobacillus acidophilus* NCFM regulates immature dendritic cell and T cell functions. Proc Natl Acad Sci USA. 2008; 105(49):19474-9. Epub 2008/12/03. doi: 10.1073/

17. Sahay B, Ge Y, Colliou N, Zadeh M, Weiner C, Mila A, et al. Advancing the use of *Lactobacillus acidophilus* surface layer protein A for the treatment of intestinal disorders in humans. Gut Microbes. 2015; 6(6):392-7. doi: 10.1080/19490976.2015.1107697. PubMed PMID: 26647142.
18. Parker J, Pollard J W, Friesen J D, Stanners C P. Stuttering: high-level mistranslation in animal and bacterial cells. Proc Natl Acad Sci USA. 1978; 75(3):1091-5. Epub 1978/03/01. doi: 10.1073/pnas.75.3.1091. PubMed PMID: 349556; PubMed Central PMCID: PMCPMC411414.
19. Leenhouts K J, Kok J, Venema G. Replacement recombination in *Lactococcus lactis*. J Bacteriol. 1991; 173(15): 4794-8. Epub 1991/08/01. doi: 10.1128/jb.173.15.4794-4798.1991. PubMed PMID: 1906872; PubMed Central PMCID: PMCPMC208158.
20. Steidler L. Gene exchange of thyA for interleukin-10 secures live GMO bacterial therapeutics. Discovery medicine. 2003; 3(19):49-51. Epub 2003/12/01. PubMed PMID: 20705040.
21. Simons G, Nijhuis M, de Vos W M. Integration and gene replacement in the *Lactococcus lactis* lac operon: induction of a cryptic phospho-beta-glucosidase in LacG-deficient strains. J Bacteriol. 1993; 175(16):5168-75. Epub 1993/08/01. doi: 10.1128/jb.175.16.5168-5175.1993. PubMed PMID: 8349556; PubMed Central PMCID: PMCPMC204984.
22. Steidler L. Genetically engineered probiotics. Best Pract Res Clin Gastroenterol. 2003; 17(5):861-76. Epub 2003/09/26. doi: 10.1016/si521-6918(03)00072-6. PubMed PMID: 14507594.
23. Schaaf A, McNealy T, Steidler A, Alken P, Michel M S. [A New Ex-Vivo 3D Bladder Matrix Model for Standardised Evaluation of Urothelial Transfection Methods]. Aktuelle Urol. 2003; 34(3):172-5. Epub 2003/10/21. doi: 10.1055/s-2003-40235. PubMed PMID: 14566689.
24. Sasaki Y, Ito Y, Sasaki T. ThyA as a selection marker in construction of food-grade host-vector and integration systems for *Streptococcus thermophilus*. Appl Environ Microbiol. 2004; 70(3):1858-64. Epub 2004/03/10. doi: 10.1128/aem.70.3.1858-1864.2004. PubMed PMID: 15006818; PubMed Central PMCID: PMCPMC368358.
25. Wong Q N, Ng V C, Lin M C, Kung H F, Chan D, Huang J D. Efficient and seamless DNA recombineering using a thymidylate synthase A selection system in *Escherichia coli*. Nucleic acids research. 2005; 33 (6):e59. Epub 2005/04/01. doi: 10.1093/nar/gni059. PubMed PMID: 15800210; PubMed Central PMCID: PMCPMC1072810.
26. Weiss A A, Babyatsky M W, Ogata S, Chen A, Itzkowitz S H. Expression of MUC2 and MUC3 mRNA in human normal, malignant, and inflammatory intestinal tissues. J Histochem Cytochem. 1996; 44(10):1161-6. Epub 1996/10/01. doi: 10.1177/44.10.8813081. PubMed PMID: 8813081.
27. Bergstrom K S, Kissoon-Singh V, Gibson D L, Ma C, Montero M, Sham H P, et al. Muc2 protects against lethal infectious colitis by disassociating pathogenic and commensal bacteria from the colonic mucosa. PLoS Pathog. 2010; 6 (5):e1000902. Epub 2010/05/21. doi: 10.1371/journal.ppat.1000902. PubMed PMID: 20485566; PubMed Central PMCID: PMC2869315.
28. Van der Sluis M, De Koning B A, De Bruijn A C, Velcich A, Meijerink J P, Van Goudoever J B, et al. Muc2-deficient mice spontaneously develop colitis, indicating that MUC2 is critical for colonic protection. Gastroenterology. 2006; 131(1):117-29. Epub 2006/07/13. doi: 10.1053/j.gastro.2006.04.020. PubMed PMID: 16831596.
29. Liu B, Yang L, Cui Z, Zheng J, Huang J, Zhao Q, et al. Anti-TNF-alpha therapy alters the gut microbiota in proteoglycan-induced ankylosing spondylitis in mice. Microbiologyopen. 2019; 8(12):e927. Epub 2019/09/27. doi: 10.1002/mbo3.927. PubMed PMID: 31556231; PubMed Central PMCID: PMCPMC6925169.
30. Kennedy N A, Heap G A, Green H D, Hamilton B, Bewshea C, Walker G J, et al. Predictors of anti-TNF treatment failure in anti-TNF-naive patients with active luminal Crohn's disease: a prospective, multicentre, cohort study. Lancet Gastroenterol Hepatol. 2019; 4(5): 341-53. Epub 2019/03/03. doi: 10.1016/S2468-1253(19) 30012-3. PubMed PMID: 30824404.
31. Lin I Y, Van T T, Smooker P M. Live-Attenuated Bacterial Vectors: Tools for Vaccine and Therapeutic Agent Delivery. Vaccines (Basel). 2015; 3(4):940-72. Epub 2015/11/17. doi: 10.3390/vaccines3040940. PubMed PMID: 26569321; PubMed Central PMCID: PMCPMC4693226.
32. Steidler L, Neirynck S, Huyghebaert N, Snoeck V, Vermeire A, Goddeeris B, et al. Biological containment of genetically modified *Lactococcus lactis* for intestinal delivery of human interleukin 10. Nat Biotechnol. 2003; 21(7):785-9. Epub 2003/06/17. doi: 10.1038/nbt840. PubMed PMID: 12808464.
33. Dorofeyev A E, Vasilenko I V, Rassokhina O A, Kondratiuk R B. Mucosal barrier in ulcerative colitis and Crohn's disease. Gastroenterology research and practice. 2013; 2013:431231. Epub 2013/06/06. doi: 10.1155/2013/431231. PubMed PMID: 23737764; PubMed Central PMCID: PMCPMC3664489.
34. Carrato C, Balague C, de Bolos C, Gonzalez E, Gambus G, Planas J, et al. Differential apomucin expression in normal and neoplastic human gastrointestinal tissues. Gastroenterology. 1994; 107(1):160-72. Epub 1994/07/01. doi: 10.1016/0016-5085(94)90073-6. PubMed PMID: 8020658.
35. Singer, I I, Kawka D W, Schloemann S, Tessner T, Riehl T, Stenson W F. Cyclooxygenase 2 is induced in colonic epithelial cells in inflammatory bowel disease. Gastroenterology. 1998; 115(2):297-306. Epub 1998/07/25. doi: 10.1016/s0016-5085(98)70196-9. PubMed PMID: 9679035.
36. Cox D G, Crusius J B, Peeters P H, Bueno-de-Mesquita H B, Pena A S, Canzian F. Haplotype of prostaglandin synthase 2/cyclooxygenase 2 is involved in the susceptibility to inflammatory bowel disease. World J Gastroenterol. 2005; 11(38):6003-8. Epub 2005/11/08. doi: 10.3748/wjg.v11.i38.6003. PubMed PMID: 16273614; PubMed Central PMCID: PMCPMC4436724.
37. Kabashima K, Saji T, Murata T, Nagamachi M, Matsuoka T, Segi E, et al. The prostaglandin receptor EP4 suppresses colitis, mucosal damage and CD4 cell activation in the gut. J Clin Invest. 2002; 109(7):883-93. Epub 2002/04/03. doi: 10.1172/JCI14459. PubMed PMID: 11927615; PubMed Central PMCID: PMCPMC150928.
38. Osaka T, Moriyama E, Arai S, Date Y, Yagi J, Kikuchi J, et al. Meta-Analysis of Fecal Microbiota and Metabolites in Experimental Colitic Mice during the Inflammatory and Healing Phases. Nutrients. 2017; 9 (12). Epub 2017/12/07. doi: 10.3390/nu9121329. PubMed PMID: 29211010; PubMed Central PMCID: PMCPMC5748779.

39. Togo A H, Diop A, Dubourg G, Khelaifia S, Richez M, Armstrong N, et al. Anaerotruncus massiliensis sp. nov., a succinate-producing bacterium isolated from human stool from an obese patient after bariatric surgery. New Microbes New Infect. 2019; 29:100508. Epub 2019/03/21. doi: 10.1016/j.nmni.2019.01.004. PubMed PMID: 30891246; PubMed Central PMCID: PMCPMC6403417.

40. Fischbach M A, Sonnenburg J L. Eating for two: how metabolism establishes interspecies interactions in the gut. Cell Host Microbe. 2011; 10(4):336-47. Epub 2011/10/25. doi: 10.1016/j.chom.2011.10.002. PubMed PMID: 22018234; PubMed Central PMCID: PMCPMC3225337.

41. Louis P, Flint H J. Formation of propionate and butyrate by the human colonic microbiota. Environ Microbiol. 2017; 19(1):29-41. Epub 2016/12/09. doi: 10.1111/1462-2920.13589. PubMed PMID: 27928878.

42. Banerjee A, Herring C A, Chen B, Kim H, Simmons A J, Southard-Smith A N, et al. Succinate Produced by Intestinal Microbes Promotes Specification of Tuft Cells to Suppress Ileal Inflammation. Gastroenterology. 2020; 159(6):2101-15 e5. Epub 2020/08/24. doi: 10.1053/j.gastro.2020.08.029. PubMed PMID: 32828819; PubMed Central PMCID: PMCPMC7725941.

43. Han R, Ma Y, Xiao J, You L, Pedisic S, Liao L. The possible mechanism of the protective effect of a sulfated polysaccharide from Gracilaria Lemaneiformis against colitis induced by dextran sulfate sodium in mice. Food Chem Toxicol. 2021; 149:112001. Epub 2021/01/23. doi: 10.1016/j.fct.2021.112001. PubMed PMID: 33482260.

44. Antharam V C, Li E C, Ishmael A, Sharma A, Mai V, Rand K H, et al. Intestinal dysbiosis and depletion of butyrogenic bacteria in Clostridium difficile infection and nosocomial diarrhea. Journal of clinical microbiology. 2013; 51(9):2884-92. Epub 2013/06/28. doi: 10.1128/JCM.00845-13. PubMed PMID: 23804381; PubMed Central PMCID: PMCPMC3754663.

45. Bajaj J S, Heuman D M, Hylemon P B, Sanyal A J, White M B, Monteith P, et al. Altered profile of human gut microbiome is associated with cirrhosis and its complications. Journal of hepatology. 2014; 60(5):940-7. Epub 2014/01/01. doi: 10.1016/j.jhep.2013.12.019. PubMed PMID: 24374295; PubMed Central PMCID: PMCPMC3995845.

46. Saresella M, Mendozzi L, Rossi V, Mazzali F, Piancone F, LaRosa F, et al. Immunological and Clinical Effect of Diet Modulation of the Gut Microbiome in Multiple Sclerosis Patients: A Pilot Study. Frontiers in immunology. 2017; 8:1391. Epub 2017/11/10. doi: 10.3389/fimmu.2017.01391. PubMed PMID: 29118761; PubMed Central PMCID: PMCPMC5661395.

47. Pasolli E, Truong D T, Malik F, Waldron L, Segata N. Machine Learning Meta-analysis of Large Metagenomic Datasets: Tools and Biological Insights. PLoS Comput Biol. 2016; 12 (7):e1004977. Epub 2016/07/12. doi: 10.1371/journal.pcbi.1004977. PubMed PMID: 27400279; PubMed Central PMCID: PMCPMC4939962.

48. Gopalakrishnan V, Spencer C N, Nezi L, Reuben A, Andrews M C, Karpinets T V, et al. Gut microbiome modulates response to anti-PD-1 immunotherapy in melanoma patients. Science. 2018; 359(6371):97-103. Epub 2017/11/04. doi: 10.1126/science.aan4236. PubMed PMID: 29097493; PubMed Central PMCID: PMCPMC5827966.

49. Allegretti J R, Kearney S, Li N, Bogart E, Bullock K, Gerber G K, et al. Recurrent Clostridium difficile infection associates with distinct bile acid and microbiome profiles. Alimentary pharmacology & therapeutics. 2016; 43(11): 1142-53. Epub 2016/04/19. doi: 10.1111/apt.13616. PubMed PMID: 27086647; PubMed Central PMCID: PMCPMC5214573.

50. Stappenbeck T S, Hooper L V, Gordon J I. Developmental regulation of intestinal angiogenesis by indigenous microbes via Paneth cells. Proc Natl Acad Sci USA. 2002; 99(24):15451-5. Epub 2002/11/15. doi: 10.1073/pnas.202604299. PubMed PMID: 12432102; PubMed Central PMCID: PMCPMC137737.

51. Human Microbiome Project C. Structure, function and diversity of the healthy human microbiome. Nature. 2012; 486(7402):207-14. Epub 2012/06/16. doi: 10.1038/nature11234. PubMed PMID: 22699609; PubMed Central PMCID: PMCPMC3564958.

52. Cash H L, Whitham C V, Behrendt C L, Hooper L V. Symbiotic bacteria direct expression of an intestinal bactericidal lectin. Science. 2006; 313(5790):1126-30. Epub 2006/08/26. doi: 10.1126/science.1127119. PubMed PMID: 16931762; PubMed Central PMCID: PMCPMC2716667.

53. Kamada N, Kim Y G, Sham H P, Vallance B A, Puente J L, Martens E C, et al. Regulated virulence controls the ability of a pathogen to compete with the gut microbiota. Science. 2012; 336(6086):1325-9. Epub 2012/05/15. doi: 10.1126/science.1222195. PubMed PMID: 22582016; PubMed Central PMCID: PMCPMC3439148.

54. Zhu W, Yan J, Zhi C, Zhou Q, Yuan X. 1,25(OH)2D3 deficiency-induced gut microbial dysbiosis degrades the colonic mucus barrier in Cyp27b1 knockout mouse model. Gut Pathog. 2019; 11:8. Epub 2019/03/05. doi: 10.1186/s13099-019-0291-z. PubMed PMID: 30828386; PubMed Central PMCID: PMCPMC6381729.

55. Fukatsu S, Horinouchi H, Nagata S, Kamei R, Tanaka D, Hong W, et al. Post-translational suppression of the high affinity IgE receptor expression on mast cells by an intestinal bacterium. Immunobiology. 2021; 226(2): 152056. Epub 2021/02/04. doi: 10.1016/j.imbio.2021.152056. PubMed PMID: 33535092.

56. Yanagibashi T, Hosono A, Oyama A, Tsuda M, Suzuki A, Hachimura S, et al. IgA production in the large intestine is modulated by a different mechanism than in the small intestine: Bacteroides acidifaciens promotes IgA production in the large intestine by inducing germinal center formation and increasing the number of IgA+B cells. Immunobiology. 2013; 218(4):645-51. Epub 2012/09/04. doi: 10.1016/j.imbio.2012.07.033. PubMed PMID: 22940255.

57. Then C K, Paillas S, Wang X, Hampson A, Kiltie A E. Association of Bacteroides acidifaciens relative abundance with high-fibre diet-associated radiosensitisation. BMC Biol. 2020; 18(1):102. Epub 2020/08/20. doi: 10.1186/s12915-020-00836-x. PubMed PMID: 32811478; PubMed Central PMCID: PMCPMC7437060.

58. Miki T, Goto R, Fujimoto M, Okada N, Hardt W D. The Bactericidal Lectin RegIIIbeta Prolongs Gut Colonization and Enteropathy in the Streptomycin Mouse Model for Salmonella Diarrhea. Cell Host Microbe. 2017; 21(2): 195-207. Epub 2017/01/24. doi: 10.1016/j.chom.2016.12.008. PubMed PMID: 28111202.

59. Wu L, Yan Q, Chen F, Cao C, Wang S. Bupleuri radix extract ameliorates impaired lipid metabolism in high-fat diet-induced obese mice via gut microbia-mediated regulation of FGF21 signaling pathway. Biomed Pharmacother. 2021; 135:111187. Epub 2021/02/09. doi: 10.1016/j.biopha.2020.111187. PubMed PMID: 33556916.

60. Wang H, Zhang X, Wang S, Li H, Lu Z, Shi J, et al. Mannan-oligosaccharide modulates the obesity and gut microbiota in high-fat diet-fed mice. Food Funct. 2018; 9(7):3916-29. Epub 2018/07/06. doi: 10.1039/c8fo00209f. PubMed PMID: 29974116.

61. Yang J Y, Lee Y S, Kim Y, Lee S H, Ryu S, Fukuda S, et al. Gut commensal *Bacteroides acidifaciens* prevents obesity and improves insulin sensitivity in mice. Mucosal Immunol. 2017; 10(1):104-16. Epub 2016/04/28. doi: 10.1038/mi.2016.42. PubMed PMID: 27118489.

62. Fang S, Chen X, Pan J, Chen Q, Zhou L, Wang C, et al. Dynamic distribution of gut microbiota in meat rabbits at different growth stages and relationship with average daily gain (ADG). BMC Microbiol. 2020; 20(1):116. Epub 2020/05/16. doi: 10.1186/s12866-020-01797-5. PubMed PMID: 32410629; PubMed Central PMCID: PMCPMC7227296.

63. Li A, Wang N, Li N, Li B, Yan F, Song Y, et al. Modulation effect of chenpi extract on gut microbiota in high-fat diet-induced obese C57BL/6 mice. J Food Biochem. 2021:e13541. Epub 2021/02/12. doi: 10.1111/jfbc.13541. PubMed PMID: 33570789.

64. Volk J K, Nystrom E E L, van der Post S, Abad B M, Schroeder B O, Johansson A, et al. The Nlrp6 inflammasome is not required for baseline colonic inner mucus layer formation or function. J Exp Med. 2019; 216(11): 2602-18. Epub 2019/08/20. doi: 10.1084/jem.20190679. PubMed PMID: 31420376; PubMed Central PMCID: PMCPMC6829596.

65. De A, Chen W, Li H, Wright J R, Lamendella R, Lukin D J, et al. Bacterial Swarmers Enriched during Intestinal Stress Ameliorate Damage. Gastroenterology. 2021. Epub 2021/03/21. doi: 10.1053/j.gastro.2021.03.017. PubMed PMID: 33741315.

66. Ma D Y, Clark E A. The role of CD40 and CD154/CD40L in dendritic cells. Semin Immunol. 2009; 21(5): 265-72. Epub 2009/06/16. doi: 10.1016/j.smim.2009.05.010. PubMed PMID: 19524453; PubMed Central PMCID: PMCPMC2749083.

67. Martin S, Agarwal R, Murugaiyan G, Saha B. CD40 expression levels modulate regulatory T cells in *Leishmania donovani* infection. J Immunol. 2010; 185(1):551-9. Epub 2010/06/08. doi: 10.4049/jimmunol.0902206. PubMed PMID: 20525887.

68. Guiducci C, Valzasina B, Dislich H, Colombo M P. CD40/CD40L interaction regulates CD4+CD25+ T reg homeostasis through dendritic cell-produced IL-2. Eur J Immunol. 2005; 35(2):557-67. Epub 2005/02/01. doi: 10.1002/eji.200425810. PubMed PMID: 15682445.

69. Zheng Y, Manzotti C N, Liu M, Burke F, Mead K I, Sansom D M. CD86 and CD80 differentially modulate the suppressive function of human regulatory T cells. J Immunol. 2004; 172(5):2778-84. Epub 2004/02/24. doi: 10.4049/jimmunol.172.5.2778. PubMed PMID: 14978077.

70. Li J G, Du Y M, Yan Z D, Yan J, Zhuansun Y X, Chen R, et al. CD80 and CD86 knockdown in dendritic cells regulates Th1/Th2 cytokine production in asthmatic mice. Exp Ther Med. 2016; 11(3):878-84. Epub 2016/03/22. doi: 10.3892/etm.2016.2989. PubMed PMID: 26998006; PubMed Central PMCID: PMCPMC4774365.

71. Brckalo T, Calzetti F, Perez-Cabezas B, Borras F E, Cassatella M A, Lopez-Botet M. Functional analysis of the CD300e receptor in human monocytes and myeloid dendritic cells. Eur J Immunol. 2010; 40(3):722-32. Epub 2009/12/30. doi: 10.1002/eji.200939468. PubMed PMID: 20039296.

72. Aarhus R, Graeff R M, Dickey D M, Walseth T F, Lee H C. ADP-ribosyl cyclase and CD38 catalyze the synthesis of a calcium-mobilizing metabolite from NADP. J Biol Chem. 1995; 270(51):30327-33. Epub 1995/12/22. doi: 10.1074/jbc.270.51.30327. PubMed PMID: 8530456.

73. Lischke T, Heesch K, Schumacher V, Schneider M, Haag F, Koch-Nolte F, et al. CD38 controls the innate immune response against *Listeria monocytogenes*. Infect Immun. 2013; 81(11):4091-9. Epub 2013/08/28. doi: 10.1128/IAI.00340-13. PubMed PMID: 23980105; PubMed Central PMCID: PMCPMC3811837.

74. Viegas M S, do Carmo A, Silva T, Seco F, Serra V, Lacerda M, et al. CD38 plays a role in effective containment of mycobacteria within granulomata and polarization of Th1 immune responses against *Mycobacterium avium*. Microbes Infect. 2007; 9(7):847-54. Epub 2007/05/30. doi: 10.1016/j.micinf.2007.03.003. PubMed PMID: 17533152.

75. Partida-Sanchez S, Cockayne D A, Monard S, Jacobson E L, Oppenheimer N, Garvy B, et al. Cyclic ADP-ribose production by CD38 regulates intracellular calcium release, extracellular calcium influx and chemotaxis in neutrophils and is required for bacterial clearance in vivo. Nat Med. 2001; 7(11):1209-16. Epub 2001/11/02. doi: 10.1038/nm1101-1209. PubMed PMID: 11689885.

76. Jablonski K A, Amici S A, Webb L M, Ruiz-Rosado Jde D, Popovich P G, Partida-Sanchez S, et al. Novel Markers to Delineate Murine M1 and M2 Macrophages. PLoS One. 2015; 10(12):e0145342. Epub 2015/12/25. doi: 10.1371/journal.pone.0145342. PubMed PMID: 26699615; PubMed Central PMCID: PMCPMC4689374.

77. Chen P, Zuo H, Xiong H, Kolar M J, Chu Q, Saghatelian A, et al. Gpr132 sensing of lactate mediates tumor-macrophage interplay to promote breast cancer metastasis. Proc Natl Acad Sci USA. 2017; 114(3):580-5. Epub 2017/01/05. doi: 10.1073/pnas.1614035114. PubMed PMID: 28049847; PubMed Central PMCID: PMCPMC5255630.

78. Kern K, Schafer S M G, Cohnen J, Pierre S, Osthues T, Tarighi N, et al. The G2A Receptor Controls Polarization of Macrophage by Determining Their Localization Within the Inflamed Tissue. Frontiers in immunology. 2018; 9:2261. Epub 2018/10/18. doi: 10.3389/fimmu.2018.02261. PubMed PMID: 30327654; PubMed Central PMCID: PMCPMC6174245.

79. Osthues T, Zimmer B, Rimola V, Klann K, Schilling K, Mathoor P, et al. The Lipid Receptor G2A (GPR132) Mediates Macrophage Migration in Nerve Injury-Induced Neuropathic Pain. Cells. 2020; 9(7). Epub 2020/07/28. doi: 10.3390/cells9071740. PubMed PMID: 32708184; PubMed Central PMCID: PMCPMC7409160.

80. Park A J, Agak G W, Qin M, Hisaw L D, Pirouz A, Kao S, et al. G2A Attenuates *Propionibacterium acnes* Induction of Inflammatory Cytokines in Human Monocytes. Ann Dermatol. 2017; 29(6):688-98. Epub 2017/12/05. doi: 10.5021/ad.2017.29.6.688. PubMed PMID: 29200756; PubMed Central PMCID: PMCPMC5705349.

81. Xiu W, Chen Q, Wang Z, Wang J, Zhou Z. Microbiota-derived short chain fatty acid promotion of Amphiregulin expression by dendritic cells is regulated by GPR43 and Blimp-1. Biochem Biophys Res Commun. 2020; 533(3): 282-8. Epub 2020/09/23. doi: 10.1016/j.bbrc.2020.09.027. PubMed PMID: 32958255.

82. Wu W, Sun M, Chen F, Cao A T, Liu H, Zhao Y, et al. Microbiota metabolite short-chain fatty acid acetate promotes intestinal IgA response to microbiota which is mediated by GPR43. Mucosal Immunol. 2017; 10(4):946-

83. Lavoie S, Chun E, Bae S, Brennan C A, Gallini Comeau C A, Lang J K, et al. Expression of Free Fatty Acid Receptor 2 by Dendritic Cells Prevents Their Expression of Interleukin 27 and Is Required for Maintenance of Mucosal Barrier and Immune Response Against Colorectal Tumors in Mice. Gastroenterology. 2020; 158(5):1359-72 e9. Epub 2020/01/10. doi: 10.1053/j.gastro.2019.12.027. PubMed PMID: 31917258; PubMed Central PMCID: PMCPMC7291292.
84. Yoshida H, Hunter Cc A. The Immunobiology of Interleukin-27. Annu Rev Immunol. 2015; 33(1):417-43. doi: 10.1146/annurev-immunol-032414-112134. PubMed PMID: 25861977.
85. Zhang H, Madi A, Yosef N, Chihara N, Awasthi A, Pot C, et al. An IL-27-Driven Transcriptional Network Identifies Regulators of IL-10 Expression across T Helper Cell Subsets. Cell Rep. 2020; 33(8):108433. Epub 2020/11/26. doi: 10.1016/j.celrep.2020.108433. PubMed PMID: 33238123; PubMed Central PMCID: PMCPMC7771052.
86. Wheaton J D, Yeh C H, Ciofani M. Cutting Edge: c-Maf Is Required for Regulatory T Cells To Adopt RORgammat (+) and Follicular Phenotypes. J Immunol. 2017; 199(12):3931-6. Epub 2017/11/12. doi: 10.4049/jimmunol.1701134. PubMed PMID: 29127150; PubMed Central PMCID: PMCPMC5728164.
87. Neumann C, Blume J, Roy U, Teh P P, Vasanthakumar A, Beller A, et al. c-Maf-dependent Treg cell control of intestinal TH17 cells and IgA establishes host-microbiota homeostasis. Nat Immunol. 2019; 20(4):471-81. Epub 2019/02/20. doi: 10.1038/s41590-019-0316-2. PubMed PMID: 30778241.
88. Apetoh L, Quintana F J, Pot C, Joller N, Xiao S, Kumar D, et al. The aryl hydrocarbon receptor interacts with c-Maf to promote the differentiation of type 1 regulatory T cells induced by IL-27. Nat Immunol. 2010; 11(9):854-61. Epub 2010/08/03. doi: 10.1038/ni.1912. PubMed PMID: 20676095; PubMed Central PMCID: PMCPMC2940320.
89. Carrier Y, Whitters M J, Miyashiro J S, LaBranche T P, Ramon H E, Benoit S E, et al. Enhanced GITR/GITRL interactions augment IL-27 expression and induce IL-10-producing Tr-1 like cells. Eur J Immunol. 2012; 42(6):1393-404. Epub 2012/06/09. doi: 10.1002/eji.201142162. PubMed PMID: 22678896.
90. Pot C, Jin H, Awasthi A, Liu S M, Lai C Y, Madan R, et al. Cutting edge: IL-27 induces the transcription factor c-Maf, cytokine IL-21, and the costimulatory receptor ICOS that coordinately act together to promote differentiation of IL-10-producing Tr cells. J Immunol. 2009; 183(2):797-801. Epub 2009/07/03. doi: 10.4049/jimmunol.0901233. PubMed PMID: 19570826; PubMed Central PMCID: PMCPMC2768608.
91. Vasanthakumar A, Kallies A. IL-27 paves different roads to Tr1. Eur J Immunol. 2013; 43(4):882-5. Epub 2013/03/19. doi: 10.1002/eji.201343479. PubMed PMID: 23504674.
92. Greenwell-Wild T, Vazquez N, Jin W, Rangel Z, Munson P J, Wahl S M. Interleukin-27 inhibition of HIV-1 involves an intermediate induction of type I interferon. Blood. 2009; 114(9):1864-74. Epub 2009/06/27. doi: 10.1182/blood-2009-03-211540. PubMed PMID: 19556424; PubMed Central PMCID: PMCPMC2738572.
93. Guo B, Chang E Y, Cheng G. The type I IFN induction pathway constrains Th17-mediated autoimmune inflammation in mice. J Clin Invest. 2008; 118(5):1680-90. Epub 2008/04/03. doi: 10.1172/JCI33342. PubMed PMID: 18382764; PubMed Central PMCID: PMCPMC2276397.
94. Iyer S S, Ghaffari A A, Cheng G. Lipopolysaccharide-mediated IL-10 transcriptional regulation requires sequential induction of type I IFNs and IL-27 in macrophages. J Immunol. 2010; 185(11):6599-607. Epub 2010/11/03. doi: 10.4049/jimmunol.1002041. PubMed PMID: 21041726; PubMed Central PMCID: PMCPMC4103176.
95. McNab F W, Ewbank J, Howes A, Moreira-Teixeira L, Martirosyan A, Ghilardi N, et al. Type I IFN induces IL-10 production in an IL-27-independent manner and blocks responsiveness to IFN-gamma for production of IL-12 and bacterial killing in *Mycobacterium tuberculosis*-infected macrophages. J Immunol. 2014; 193(7):3600-12. Epub 2014/09/05. doi: 10.4049/jimmunol.1401088. PubMed PMID: 25187652; PubMed Central PMCID: PMCPMC4170673.

We claim:

1. An isolated bacterial surface layer protein A (SlpA) protein comprising SEQ ID NO: 5.

2. The SlpA protein of claim 1, wherein the protein:
   a) comprises a molecular label conjugated to the protein, or
   b) is a multimeric protein.

3. The SlpA protein of claim 2, wherein the molecular label is a radiolabel, fluorescent label, affinity label or targeting label.

4. A composition comprising the SlpA protein according to claim 1 and a pharmaceutically acceptable carrier and/or excipient, optionally in combination with sulfasalazine, cyclosporine, prednisone, methylprednisone, budesonide, mesalamine, azathioprine, tumor necrosis factor (TNF) inhibitors, methotrexate, 6-mercaptopurine, a corticosteroid, infliximab or combinations thereof.

5. A recombinant bacterium genetically modified to express a surface layer protein A (SlpA) comprising SEQ ID NO: 5.

6. The recombinant bacterium of claim 5, wherein said recombinant bacterium secretes SlpA.

7. The recombinant bacterium of claim 5, wherein said recombinant bacterium is selected from the group consisting of *Lactococcus* (*L.*) *chungangensis, L. formosensis, L. fujiensis, L. hircilactis, L. garvieae, L. lactis, L. laudensis, L. nasutitermitis, L. piscium, L. plantarum, L. raffinolactis,* and *L. taiwanensis*.

8. The recombinant bacterium of claim 7, wherein said recombinant bacterium is *L. lactis*.

9. The recombinant bacterium of claim 5, wherein said recombinant bacterium is a lactic acid bacterium.

10. The recombinant bacterium of claim 9, wherein said lactic acid bacterium is a *Lactococcus* species.

11. A probiotic food comprising the recombinant bacterium of claim 5.

12. The probiotic food of claim 11, wherein the food is yogurt, fermented vegetable, kefir, sauerkraut, miso soup, pickle, tempeh or kimchi.

* * * * *

```
SEQUENCE LISTING

<160> NUMBER OF SEQ ID NOS: 21

<210> SEQ ID NO 1
<211> LENGTH: 22
<212> TYPE: DNA
<213> ORGANISM: Artificial Sequence
<220> FEATURE:
<223> OTHER INFORMATION: Oligonucleotide primer 132

<400> SEQUENCE: 1
gaccgccttt ccgttattat cc                                              22

<210> SEQ ID NO 2
<211> LENGTH: 26
<212> TYPE: DNA
<213> ORGANISM: Artificial Sequence
<220> FEATURE:
<223> OTHER INFORMATION: Oligonucleotide primer 133

<400> SEQUENCE: 2
```

```
tggggcggaa gtggaaatac ttatgg                                        26
```

<210> SEQ ID NO 3
<211> LENGTH: 33
<212> TYPE: DNA
<213> ORGANISM: Artificial Sequence
<220> FEATURE:
<223> OTHER INFORMATION: Oligonucleotide primer 123

<400> SEQUENCE: 3

```
gcatgctcga gtctagaagt cttataacta tac                                33
```

<210> SEQ ID NO 4
<211> LENGTH: 34
<212> TYPE: DNA
<213> ORGANISM: Artificial Sequence
<220> FEATURE:
<223> OTHER INFORMATION: Oligonucleotide primer 126

<400> SEQUENCE: 4

```
gtcgaccggt ttatcgaaaa ttagctactt ttac                               34
```

<210> SEQ ID NO 5
<211> LENGTH: 447
<212> TYPE: PRT
<213> ORGANISM: Artificial Sequence
<220> FEATURE:
<223> OTHER INFORMATION: Recombinant SlpA

<400> SEQUENCE: 5

```
Met Gln Ser Ser Leu Lys Lys Ser Leu Tyr Leu Gly Leu Ala Ala Leu
1               5                   10                  15

Ser Phe Ala Gly Val Ala Ala Val Ser Thr Thr Ala Ser Ala Lys Ser
                20                  25                  30

Arg Met Ala Thr Thr Ile Asn Ala Ser Ser Ala Ile Asn Thr Asn
        35                  40                  45

Thr Asn Ala Lys Tyr Asp Val Asp Val Thr Pro Ser Val Ser Ala Val
    50                  55                  60

Ala Ala Asn Thr Ala Asn Asn Thr Pro Ala Ile Ala Gly Asn Leu Thr
65                  70                  75                  80

Gly Thr Ile Ser Ala Ser Tyr Asn Gly Lys Thr Tyr Thr Ala Asn Leu
                85                  90                  95

Lys Ala Asp Thr Glu Asn Ala Thr Ile Thr Ala Ala Gly Ser Thr Thr
            100                 105                 110

Ala Val Lys Pro Ala Glu Leu Ala Ala Gly Val Ala Tyr Thr Val Thr
        115                 120                 125

Val Asn Asp Val Ser Phe Asn Phe Gly Ser Glu Asn Ala Gly Lys Thr
    130                 135                 140

Val Thr Leu Gly Ser Ala Asn Ser Asn Val Lys Phe Thr Gly Thr Asn
145                 150                 155                 160

Ser Asp Asn Gln Thr Glu Thr Asn Val Ser Thr Leu Lys Val Lys Leu
                165                 170                 175

Asp Gln Asn Gly Val Ala Ser Leu Thr Asn Val Ser Ile Ala Asn Val
            180                 185                 190

Tyr Ala Ile Asn Thr Thr Asp Asn Ser Asn Val Asn Phe Tyr Asp Val
        195                 200                 205

Thr Ser Gly Ala Thr Val Thr Asn Gly Ala Val Ser Val Asn Ala Asp
    210                 215                 220

Asn Gln Gly Gln Val Asn Val Ala Asn Val Val Ala Ala Ile Asn Ser
```

```
            225                 230                 235                 240

Lys Tyr Phe Ala Ala Gln Tyr Ala Asp Lys Lys Leu Asn Thr Arg Thr
                    245                 250                 255

Ala Asn Thr Glu Asp Ala Ile Lys Ala Ala Leu Lys Asp Gln Lys Ile
                260                 265                 270

Asp Val Asn Ser Val Gly Tyr Phe Lys Ala Pro His Thr Phe Thr Val
            275                 280                 285

Asn Val Lys Ala Thr Ser Asn Thr Asn Gly Lys Ser Ala Thr Leu Pro
        290                 295                 300

Val Val Val Thr Val Pro Asn Val Ala Glu Pro Thr Val Ala Ser Val
    305                 310                 315                 320

Ser Lys Arg Ile Met His Asn Ala Tyr Tyr Tyr Asp Lys Asp Ala Lys
                    325                 330                 335

Arg Val Gly Thr Asp Ser Val Lys Arg Tyr Asn Ser Val Ser Val Leu
                340                 345                 350

Pro Asn Thr Thr Thr Ile Asn Gly Lys Thr Tyr Tyr Gln Val Val Glu
            355                 360                 365

Asn Gly Lys Ala Val Asp Lys Tyr Ile Asn Ala Ala Asn Ile Asp Gly
        370                 375                 380

Thr Lys Arg Thr Leu Lys His Asn Ala Tyr Val Tyr Ala Ser Ser Lys
    385                 390                 395                 400

Lys Arg Ala Asn Lys Val Val Leu Lys Lys Gly Glu Val Val Thr Thr
                    405                 410                 415

Tyr Gly Ala Ser Tyr Thr Phe Lys Asn Gly Gln Lys Tyr Tyr Lys Ile
                420                 425                 430

Gly Asp Asn Thr Asp Lys Thr Tyr Val Lys Val Ala Asn Phe Arg
            435                 440                 445

<210> SEQ ID NO 6
<211> LENGTH: 1344
<212> TYPE: DNA
<213> ORGANISM: Artificial Sequence
<220> FEATURE:
<223> OTHER INFORMATION: Recombinant slpA nucleotide sequence encoding
      SEQ ID NO: 5

<400> SEQUENCE: 6
atgcaatcaa gtttaaagaa atctctttac ttgggccttg ccgcattgag ctttgctggt       60
gttgctgccg tttcaacgac tgcttcagct aagtcgcgaa tggcgacaac tattaacgcg      120
tcttcatctg ctattaatac gaacacaaat gctaaatatg acgttgatgt caccccttct      180
gtgagtgctg tcgcagcaaa caccgctaat aatactcctg ccattgctgg taatttaaca      240
ggaacaatct cagcgagtta caatggtaaa acttatacag cgaaccttaa ggccgacact      300
gaaaatgcaa ccataactgc cgccggatca acaacagccg tcaaaccagc cgaattagca      360
gcaggtgttg cctatactgt cacagttaat gacgtttctt ttaattttgg ttctgaaaat      420
gctggtaaaa ctgtcacgtt gggatctgcc aattcaaatg tcaaattcac agggacaaat      480
tcagataacc aaaccgaaac taatgttagt acattgaaag ttaaattaga tcagaacgga      540
gtcgcatctt aacaaacgt ttctattgct aatgtctatg ctattaacac aacggacaac      600
tctaatgtaa acttttatga tgttacctca ggcgcaacag taactaatgg agcagtatct      660
gtcaacgccg ataatcaagg acaagttaat gttgccaacg tcgtagcagc tattaattct      720
aaatattttg ccgctcaata tgcagacaaa aaattgaata cacgaaccgc aaataccgaa      780
gatgcaatca agccgcccct taaagaccaa aaaatcgatg taaactcagt aggttatttt      840
```

-continued

```
aaagcacctc ataccttac agttaatgtt aaagccacat caaataccaa tggaaaatct    900
gctacattgc ctgttgtagt tactgtgcca atgttgccg aacctacagt tgcctcagtg    960
tcaaaacgaa tcatgcataa tgcctactat tatgataaag atgctaaacg tgtaggaact  1020
gattcagtaa aaagatataa ctctgtaagt gtacttccaa acacaacaac aattaatgga  1080
aaaacgtatt atcaagtagt tgaaaatggg aaagcggtgg ataaatacat taatgcggca  1140
aatattgacg gtacgaaaag aacattaaaa cataatgcat atgtgtatgc ctctagtaaa  1200
aaacgagcta ataagtagt cttaaaaaa ggtgaagttg taacaactta tggggcctct  1260
tatactttca aaatggtca aaatattat aaaattggag ataatacaga taagacatat  1320
gtaaaagtag ctaattttcg ataa                                        1344
```

<210> SEQ ID NO 7
<211> LENGTH: 288
<212> TYPE: PRT
<213> ORGANISM: Lactobacillus acidophilus

<400> SEQUENCE: 7

```
Ala Ala Thr Thr Ile Asn Ala Ser Ser Ala Ile Asn Thr Asn Thr
1               5                   10                  15

Asn Ala Lys Tyr Asp Val Asp Val Thr Pro Ser Val Ser Ala Val Ala
                20                  25                  30

Ala Val Ala Ala Asn Thr Ala Asn Asn Thr Pro Ala Ile Ala Gly Asn
            35                  40                  45

Leu Thr Gly Thr Ile Ser Ala Ser Tyr Asn Gly Lys Thr Tyr Thr Ala
        50                  55                  60

Asn Leu Lys Ala Asp Thr Glu Asn Ala Thr Ile Thr Ala Ala Gly Ser
65                  70                  75                  80

Thr Thr Ala Val Lys Pro Ala Glu Leu Ala Ala Gly Val Ala Tyr Thr
                85                  90                  95

Val Thr Val Asn Asp Val Ser Phe Asn Phe Gly Ser Glu Asn Ala Gly
                100                 105                 110

Lys Thr Val Thr Leu Gly Ser Ala Asn Ser Asn Val Lys Phe Thr Gly
            115                 120                 125

Thr Asn Ser Asp Asn Gln Thr Glu Thr Asn Val Ser Thr Leu Lys Val
        130                 135                 140

Lys Leu Asp Gln Asn Gly Val Ala Ser Leu Thr Asn Val Ser Ile Ala
145                 150                 155                 160

Asn Val Tyr Ala Ile Asn Thr Asp Asn Ser Asn Val Asn Phe Tyr
                165                 170                 175

Asp Val Thr Ser Gly Ala Thr Val Thr Asn Gly Ala Val Ser Val Asn
                180                 185                 190

Ala Asp Asn Gln Gly Gln Val Asn Val Ala Asn Val Val Ala Ala Ile
            195                 200                 205

Asn Ser Lys Tyr Phe Ala Ala Gln Tyr Ala Asp Lys Lys Leu Asn Thr
        210                 215                 220

Arg Thr Ala Asn Thr Glu Asp Ala Ile Lys Ala Ala Leu Lys Asp Gln
225                 230                 235                 240

Lys Ile Asp Val Asn Ser Val Gly Tyr Phe Lys Ala Pro His Thr Phe
                245                 250                 255

Thr Val Asn Val Lys Ala Thr Ser Asn Thr Asn Gly Lys Ser Ala Thr
                260                 265                 270

Leu Pro Val Val Val Thr Val Pro Asn Val Ala Glu Pro Thr Val Ala
```

```
                     275                 280                 285

<210> SEQ ID NO 8
<211> LENGTH: 444
<212> TYPE: PRT
<213> ORGANISM: Lactobacillus acidophilus

<400> SEQUENCE: 8

Met Lys Lys Asn Leu Arg Ile Val Ser Ala Ala Ala Ala Leu Leu
1               5                   10                  15

Ala Val Ala Pro Val Ala Ala Ser Ala Val Ser Thr Val Ser Ala Ala
                20                  25                  30

Thr Thr Ile Asn Ala Ser Ser Ala Ile Asn Thr Asn Thr Asn Ala
                35                  40                  45

Lys Tyr Asp Val Asp Val Thr Pro Ser Val Ser Ala Val Ala Ala Asn
    50                  55                  60

Thr Ala Asn Asn Thr Pro Ala Ile Ala Gly Asn Leu Thr Gly Thr Ile
65                  70                  75                  80

Ser Ala Ser Tyr Asn Gly Lys Thr Tyr Thr Ala Asn Leu Lys Ala Asp
                85                  90                  95

Thr Glu Asn Ala Thr Ile Thr Ala Ala Gly Ser Thr Thr Ala Val Lys
                100                 105                 110

Pro Ala Glu Leu Ala Ala Gly Val Ala Tyr Thr Val Thr Val Asn Asp
                115                 120                 125

Val Ser Phe Asn Phe Gly Ser Glu Asn Ala Gly Lys Thr Val Thr Leu
                130                 135                 140

Gly Ser Ala Asn Ser Asn Val Lys Phe Thr Gly Thr Asn Ser Asp Asn
145                 150                 155                 160

Gln Thr Glu Thr Asn Val Ser Thr Leu Lys Val Lys Leu Asp Gln Asn
                165                 170                 175

Gly Val Ala Ser Leu Thr Asn Val Ser Ile Ala Asn Val Tyr Ala Ile
                180                 185                 190

Asn Thr Thr Asp Asn Ser Asn Val Asn Phe Tyr Asp Val Thr Ser Gly
                195                 200                 205

Ala Thr Val Thr Asn Gly Ala Val Ser Val Asn Ala Asp Asn Gln Gly
                210                 215                 220

Gln Val Asn Val Ala Asn Val Val Ala Ile Asn Ser Lys Tyr Phe
225                 230                 235                 240

Ala Ala Gln Tyr Ala Asp Lys Lys Leu Asn Thr Arg Thr Ala Asn Thr
                245                 250                 255

Glu Asp Ala Ile Lys Ala Ala Leu Lys Asp Gln Lys Ile Asp Val Asn
                260                 265                 270

Ser Val Gly Tyr Phe Lys Ala Pro His Thr Phe Thr Val Asn Val Lys
                275                 280                 285

Ala Thr Ser Asn Thr Asn Gly Lys Ser Ala Thr Leu Pro Val Val Val
                290                 295                 300

Thr Val Pro Asn Val Ala Glu Pro Thr Val Ala Ser Val Ser Lys Arg
305                 310                 315                 320

Ile Met His Asn Ala Tyr Tyr Tyr Asp Lys Asp Ala Lys Arg Val Gly
                325                 330                 335

Thr Asp Ser Val Lys Arg Tyr Asn Ser Val Ser Val Leu Pro Asn Thr
                340                 345                 350

Thr Thr Ile Asn Gly Lys Thr Tyr Tyr Gln Val Val Glu Asn Gly Lys
                355                 360                 365
```

```
Ala Val Asp Lys Tyr Ile Asn Ala Ala Asn Ile Asp Gly Thr Lys Arg
    370                 375                 380

Thr Leu Lys His Asn Ala Tyr Val Tyr Ala Ser Ser Lys Lys Arg Ala
385                 390                 395                 400

Asn Lys Val Val Leu Lys Lys Gly Glu Val Val Thr Thr Tyr Gly Ala
                405                 410                 415

Ser Tyr Thr Phe Lys Asn Gly Gln Lys Tyr Tyr Lys Ile Gly Asp Asn
                420                 425                 430

Thr Asp Lys Thr Tyr Val Lys Val Ala Asn Phe Arg
            435                 440

<210> SEQ ID NO 9
<211> LENGTH: 469
<212> TYPE: PRT
<213> ORGANISM: Levilactobacillus brevis

<400> SEQUENCE: 9

Met Phe Gly Gly Arg Lys Ile Met Gln Ser Ser Leu Lys Lys Ser Leu
1               5                   10                  15

Tyr Leu Gly Leu Ala Ala Leu Ser Phe Ala Gly Val Ala Ala Val Ser
                20                  25                  30

Thr Thr Ala Ser Ala Lys Ser Tyr Ala Thr Ala Gly Ala Tyr Thr Thr
                35                  40                  45

Leu Lys Thr Asp Ala Thr Lys Arg Asn Val Glu Ala Thr Gly Thr Asn
    50                  55                  60

Ala Leu Tyr Thr Lys Pro Gly Thr Val Lys Gly Ala Lys Val Val Ala
65                  70                  75                  80

Ser Lys Ala Thr Met Ala Lys Leu Ala Ser Ser Lys Lys Ser Ala Asp
                85                  90                  95

Tyr Phe Arg Ala Tyr Gly Val Lys Thr Thr Asn Arg Gly Ser Val Tyr
                100                 105                 110

Tyr Arg Val Val Ser Met Asp Gly Lys Tyr Arg Gly Tyr Val Tyr Gly
                115                 120                 125

Gly Lys Ser Asp Thr Ala Phe Ala Gly Gly Ile Lys Ser Ala Asp Thr
    130                 135                 140

Thr Thr Thr Ala Thr Thr Pro Thr Arg Thr Thr Gly Tyr Tyr Leu Lys
145                 150                 155                 160

Asp Val Ser Lys Asn Thr Leu Trp Thr Ala Pro Lys Asn Thr Gln Tyr
                165                 170                 175

Lys Ala Ser Lys Val Ser Leu Tyr Gly Val Lys Ser Thr Asp Thr Phe
                180                 185                 190

Lys Val Asp Ser Ala Ala Thr Lys Thr Arg Glu Gly Ser Leu Tyr Tyr
                195                 200                 205

His Val Thr Asp Thr Gln Asn Thr Ser Val Ser Gly Trp Ile Tyr Ala
    210                 215                 220

Gly Lys Gly Tyr Val Ala Gly Thr Thr Gln Asp Leu Gly Leu
225                 230                 235                 240

Ser Leu Thr Met Ser Asp Ala Ala Thr Ser Asp Asn Ser Val Lys
                245                 250                 255

Val Val Tyr Arg Ala Ser Gly Ser Gln Val Gly Thr Ala Thr Trp Val
                260                 265                 270

Thr Ala Ala Ala Gly Thr Lys Ala Gly Ala Thr Val Gly Thr Thr Ala
                275                 280                 285

Val Asn Ala Ala Gly Val Lys Leu Ala Asp Phe Val Thr Asn Ser Leu
                290                 295                 300
```

Pro Ser Gly Tyr Thr Thr Thr Gly Thr Val Asp Thr Ala Ser Ala Thr
305                 310                 315                 320

Tyr Gly Asn Thr Val Tyr Val Asp Val Thr Ala Ala Thr Ser Lys
                325                 330                 335

Val Gln Leu Val Ala Asp Asn Val Asp Asn Thr Ala Ser Thr Thr Asp
            340                 345                 350

Asn Ala Val Ala Gly Val Leu Ala Asn Gly Ala Lys Leu Ser Ser Ser
            355                 360                 365

Asp Leu Ser Ala Thr Leu Lys Glu Ala Gly Ile Lys Ala Leu Thr Gly
370                 375                 380

Thr Lys Gly Glu Ala Ile Gly Ala Thr Asn Leu Ala Thr Ile Ser Gly
385                 390                 395                 400

Ala Phe Asp Thr Ala Glu Ile Asn Gly Ser Lys Thr Tyr Tyr Ala Ala
                405                 410                 415

Asn Gly Asp Ala Tyr His Tyr Val Phe Thr Tyr Glu Pro Ala Asn Phe
            420                 425                 430

Ala Asn Asp Asn Arg Leu Ala Thr Tyr Gly Asp Thr Leu Thr Ala Ser
            435                 440                 445

Phe Lys Ala Val Leu Thr Lys Gly Ala Pro Ser Ala Ser Ser Ser Asn
450                 455                 460

Ser Ser Trp Ile Ala
465

<210> SEQ ID NO 10
<211> LENGTH: 451
<212> TYPE: PRT
<213> ORGANISM: Lactobacillus crispatus

<400> SEQUENCE: 10

Met Lys Lys Asn Leu Arg Ile Val Ser Ala Ala Ala Ala Leu Leu
1               5                   10                  15

Ala Val Ala Pro Val Ala Ala Ser Ala Val Ser Val Asn Ala Ala Asp
            20                  25                  30

Asn Thr Val Ala Thr Thr Thr Asn Thr Ala Asn Thr Val Ile Asn Ala
            35                  40                  45

Asp Gly Thr Ala Ile Asn Thr Pro Ala Asp Ala Lys Tyr Asp Val Asp
50                  55                  60

Val Thr Pro Asn Leu Thr Ala Thr Ala Ala Ser Thr Val Asn Gly Gln
65                  70                  75                  80

Thr Ile Asn Gly Ser Ile Thr Gly Asn Ile Thr Ala Ser Tyr Asn Gly
                85                  90                  95

Gln Ser Tyr Thr Gly Thr Leu Asp Thr Lys Asn Gly Lys Val Ser Val
            100                 105                 110

Ala Asp Ser Lys Gly Thr Ala Val Thr Asp Phe Ser Lys Leu Thr Asn
            115                 120                 125

Gly Ser Tyr Thr Val Thr Val Ser Gly Val Ser Phe Asn Phe Gly Thr
            130                 135                 140

Ala Asn Ala Asn Lys Thr Ile Thr Leu Gly Ser Lys Asn Ser Asn Val
145                 150                 155                 160

Lys Phe Ala Gly Ala Asp Gly Lys Phe Ala Asp Thr Val Lys Val Glu
                165                 170                 175

Leu Gly Gln Asn Gly Thr Leu Thr Thr Pro Ile Ser Val Gln Val Ser
            180                 185                 190

Asn Val Asn Ala Leu Asp Leu Ser Asn Ala Asn Gly Val Asn Phe Tyr

```
                195                 200                 205
Asn Ala Ser Asn Gly Ser Gln Val Thr Lys Gly Ser Val Asn Val Thr
210                 215                 220

Ala Gly Leu Ile Gly Arg Leu Asn Val Ser Thr Val Ala Ser Glu Ile
225                 230                 235                 240

Leu Lys Asn Cys Ala Ala Tyr Gln Val Ser Asn Gly Lys Pro Val Ser
                245                 250                 255

Gln Leu Pro Asp Gln Lys Ala Val Val Ala Asp Val Asn Ala Ala Leu
                260                 265                 270

Lys Ala Ala Asn Ile Pro Val Asp Asn Ala Gly Trp Phe Thr Ala Pro
                275                 280                 285

Ile Ser Leu Ser Val Asn Val Lys Ala Ser Ser Ile Asn Gly Val
290                 295                 300

Gly Cys Tyr Phe Thr Cys Thr Val Asn Val Ala Asn Gly Lys Asp Met
305                 310                 315                 320

Thr Val Pro Ser Gln Ser Lys Thr Ile Met His Asn Ala Tyr Tyr Tyr
                325                 330                 335

Asp Lys Asp Ala Lys Arg Val Gly Thr Asp Lys Leu Thr Arg Tyr Asn
                340                 345                 350

Ser Val Thr Val Ala Met Asn Thr Thr Ile Asn Gly Lys Ala Tyr
                355                 360                 365

Tyr Glu Val Ile Glu Asn Gly Lys Ala Thr Gly Lys Phe Ile Asn Ala
370                 375                 380

Asp Asn Ile Asp Gly Thr Lys Arg Thr Leu Lys His Asn Ala Tyr Val
385                 390                 395                 400

Tyr Lys Thr Ser Lys Lys Arg Ala Asn Lys Val Thr Leu Lys Lys Gly
                405                 410                 415

Thr Glu Val Thr Thr Tyr Gly Gly Thr Tyr Thr Phe Lys Asn Gly Lys
                420                 425                 430

Gln Tyr Tyr Lys Ile Gly Asn Asn Thr Asp Lys Thr Tyr Val Lys Ala
                435                 440                 445

Ser Asn Phe
    450

<210> SEQ ID NO 11
<211> LENGTH: 439
<212> TYPE: PRT
<213> ORGANISM: Lactobacillus crispatus

<400> SEQUENCE: 11

Met Lys Lys Asn Leu Arg Ile Val Ser Ala Ala Ala Ala Ala Leu Leu
1               5                   10                  15

Ala Val Ala Pro Val Ala Ala Gly Val Ser Ser Val Thr Ala Ser
                20                  25                  30

Ser Ile Glu Phe Val Gly Ser Ser Asn Ser Ser Leu Leu Pro Glu Val
            35                  40                  45

Asn Asp His Thr Val Asn Phe Gly Ile Asn Phe Asn Ala Ile Gly Ala
        50                  55                  60

Tyr Gly Asn Val Pro Ser Ser Val Ser Ala Thr Ala Glu Val Thr Ile
65                  70                  75                  80

Asn Gly Gln Lys Thr Thr Ile Asn Leu Pro Glu Asn Gln Lys Ser Tyr
                85                  90                  95

Ile Tyr Tyr Ala Thr Thr Asn Glu Ser Val Asp Ala Ser Lys Leu Val
            100                 105                 110
```

```
Ala Gly Gln Lys Tyr Tyr Thr Gly Ile Asn Asn Ala Ser Leu Asn Leu
            115                 120                 125

Gly Ser Pro Asn His Asp Lys Asp Ile Thr Leu Glu Gly Ser Asn Val
130                 135                 140

Ser Phe Lys Thr Asn Asp Ser Asp Pro Tyr Thr Lys Thr Leu Lys Val
145                 150                 155                 160

Asn Thr Asp Lys Asn Gly Val Ile Ser Asn Leu Ser Ile Lys Ser Ala
                165                 170                 175

Asn Phe Asp Ala Val Asp Val Asn Asn Ala Arg Thr Val Ser Phe Tyr
            180                 185                 190

Asp Ala Asp Thr Gly Asn Ile Val Thr Ser Gly Ala Leu Glu Ile Asn
        195                 200                 205

Ala Gly Pro Asn Ala Gln Met Asn Val Gln Thr Ile Leu Ala Lys Phe
    210                 215                 220

Glu Gln Lys Tyr Gln Ala Ala Gln Leu Asn Asn Ala Gly Thr Thr Asn
225                 230                 235                 240

Asn Val Ser Tyr Asn Asn Asp Leu Ile Ser Thr Thr Pro Ala Asp Leu
                245                 250                 255

Ala Ala Gln Leu Lys Lys Ala Gly Tyr Ser Val Asp Asn Asn Gly Tyr
            260                 265                 270

Phe Thr Ala Lys His Ser Phe Thr Val Asn Phe Ser Ala Lys Ser Gly
        275                 280                 285

Gln Asn Gly Tyr Thr Thr Thr Met Pro Val Thr Val Thr Val Pro Asn
    290                 295                 300

Val Ala Glu Glu Thr Val Pro Ser Gln Ile Arg Thr Val Met His Asn
305                 310                 315                 320

Ala Phe Phe Tyr Asp Lys Asn Gly Lys Arg Val Gly Ser Asp Lys Val
                325                 330                 335

Thr Arg Tyr Asn Ser Ala Thr Val Ala Met Asn Thr Thr Ile Ile
            340                 345                 350

Gly Lys Ala Tyr Tyr Glu Val Ile Glu Asn Gly Lys Ala Thr Gly Lys
        355                 360                 365

Phe Ile Asn Ala Ala Asn Ile Asp Gly Thr Lys Arg Thr Leu Lys His
    370                 375                 380

Asn Ala Tyr Val Tyr Lys Ser Ser Lys Lys Arg Ala Asn Lys Val Val
385                 390                 395                 400

Leu Lys Lys Gly Glu Thr Val Val Thr Tyr Gly Ala Tyr Thr Phe
                405                 410                 415

Lys Asn Gly Lys Gln Tyr Lys Ile Gly Asn Thr Asp Lys Thr
            420                 425                 430

Tyr Val Lys Val Ala Asn Phe
        435

<210> SEQ ID NO 12
<211> LENGTH: 442
<212> TYPE: PRT
<213> ORGANISM: Lactobacillus crispatus

<400> SEQUENCE: 12

Met Lys Lys Asn Leu Arg Ile Val Ser Ala Ala Ala Ala Leu Leu
1               5                   10                  15

Ala Val Ala Pro Val Ala Ala Ser Ala Val Ser Val Asn Ala Ala Ser
            20                  25                  30

Ser Ser Ala Val Gln Thr Ala Thr Asn Ile Gly Thr Val Leu Pro Leu
        35                  40                  45
```

Thr Asp Gly Ser Thr Val Asn Val Lys Pro Asn Ile Ser Leu Asn Thr
 50                  55                  60

Ser Ala Tyr Glu Gly Val Lys Ala Asn Ile Ser Val Ser Phe Ser Ala
 65                  70                  75                  80

Thr Val Asp Gly Thr Thr Ala Thr Ser Asn Phe Thr Pro Asn Ala Ser
                 85                  90                  95

Thr Ile Glu Leu Trp Lys Asn Glu Lys Asn Lys Val Thr Gln Val Thr
            100                 105                 110

Tyr Leu Gln Gln Val Thr Ser Ser Asn Ala Gly Ala Thr Tyr Gln Val
        115                 120                 125

Lys Met Thr Gln Val Gly Leu Asn Phe Gly Ser Gln Asn Ala Asn Lys
    130                 135                 140

Lys Val Thr Leu Thr Phe Pro Glu Gly Asp Met Phe Lys Thr Ala Asp
145                 150                 155                 160

Thr Ser Leu Ala Gln Ser His Glu Val Lys Leu Asp Gln Asn Gly Thr
                165                 170                 175

Ile Thr Leu Pro Glu Val Val Met Asn Val Thr Ala Lys Asp Phe Ala
            180                 185                 190

Asn Pro Ala Val Val Asn Trp Tyr Asn Thr Ala Thr Asn Ala Val Val
        195                 200                 205

Ser Thr Gly Asn Ile Glu Leu Phe Ala Gly Ser Asp Ala Gly Lys Met
    210                 215                 220

Asn Val Ala Gln Val Val Ser Ala Thr Glu Lys Lys Tyr His Ala Ser
225                 230                 235                 240

Asn Tyr Gly Thr Lys Ala Asn Gln Glu Ser Ser Thr Ile Ser Tyr Thr
                245                 250                 255

Asn Asn Leu Lys Asp Ala Leu Lys Ala Met Asn Val Asp Val Asp Ala
            260                 265                 270

Gln Gly Trp Phe Val Ala Pro Lys Ser Phe Thr Phe Asn Met Thr Ala
        275                 280                 285

Lys Ala Asn Asn Asn Asp Ala Ser Ser Thr Leu Ala Val Thr Val Ser
    290                 295                 300

Val Pro Asn Gly Lys Asp Met Thr Val Pro Ser Gln Ser Lys Thr Val
305                 310                 315                 320

Met His Asn Ala Phe Phe Tyr Asp Lys Asn Gly Lys Arg Val Gly Ser
                325                 330                 335

Asp Lys Val Thr Arg Tyr Asn Ser Ala Thr Val Ala Met Asn Thr Thr
            340                 345                 350

Thr Ile Asn Gly Lys Ala Tyr Tyr Glu Val Ile Glu Asn Gly Lys Ala
        355                 360                 365

Thr Gly Lys Phe Ile Asn Ala Ala Asn Ile Asp Gly Thr Lys Arg Thr
    370                 375                 380

Leu Lys His Asn Ala Tyr Val Tyr Lys Ser Ser Lys Lys Arg Ala Asn
385                 390                 395                 400

Lys Val Val Leu Lys Lys Gly Thr Glu Val Thr Tyr Gly Gly Ala
                405                 410                 415

Tyr Thr Phe Lys Asn Gly Lys Gln Tyr Tyr Lys Ile Gly Asn Asn Thr
            420                 425                 430

Asp Lys Thr Tyr Val Lys Val Ser Asn Phe
        435                 440

<210> SEQ ID NO 13
<211> LENGTH: 322

```
<212> TYPE: PRT
<213> ORGANISM: Lactobacillus helveticus

<400> SEQUENCE: 13

Ser Val Ser Glu Ser Lys Asp Thr Val Asn Val Thr Pro Ser Phe Thr
1               5                   10                  15

Leu Thr Ser Ala Ile Pro Ala Lys Gly Val Pro Ala Thr Leu Gln Gly
            20                  25                  30

Ser Ile Glu Ala Ser Leu Asn Gly Thr Ser Val Thr Ala Asp Val Ala
        35                  40                  45

Asp Val Ala Lys Asp Val Thr Leu Thr Asp Gly Asn Lys Thr Val Tyr
    50                  55                  60

Ser Tyr Asn Glu Arg Glu Asn Lys Val Asp Asn Asn Leu Ser Ala Val
65              70                  75                  80

Glu Ala Ser Lys Glu Tyr Thr Met Thr Leu Ser Gly Val Gly Phe Ser
                85                  90                  95

Phe Gly Lys Ala Asn Ala Gly Lys Thr Leu Thr Phe Lys Leu Pro Lys
            100                 105                 110

Asn Val Lys Val Asn Asp Thr Ser Asn Asp Val Lys Val Ser Leu Asp
        115                 120                 125

Gln Tyr Gly Asn Ala Thr Asn Leu Lys Phe Val Ile Ser Asn Ile Lys
    130                 135                 140

Ala Tyr Asp Ser Ala Asn Thr Asn Ala Val Ser Phe Tyr Ala Ala Lys
145                 150                 155                 160

Ser Gly Leu Val Ala Thr Gln Gly Ser Tyr Met Thr Leu Ala Asp Glu
                165                 170                 175

Asn Gly Asn Leu Asn Val Asn Thr Leu Leu Asp Lys Leu Lys Gly Lys
            180                 185                 190

Tyr Glu Ala Met Gln Phe Lys Asp Ser Lys Phe Glu Thr Val Asn Val
        195                 200                 205

Asn Thr Thr Ala Asp Asp Val Lys Ala Glu Leu Glu Lys Ala Gly Ile
    210                 215                 220

Lys Val Asp Ala Ala Asn Asn Phe Glu Ala Pro Asp Thr Phe Thr Val
225                 230                 235                 240

Thr Leu Asn Ala Lys Ser Asp Val Asn Gly Lys Thr Ala Ser Leu Pro
                245                 250                 255

Val Val Val Thr Val Pro Asn Gly Lys Ser Thr Val Pro Ser Gln
            260                 265                 270

Ser Lys Thr Ile Met His Asn Ala Tyr Tyr Asp Lys Asp Ala Lys
        275                 280                 285

Arg Val Gly Thr Asp Lys Val Thr Arg Tyr Asn Ala Val Thr Val Ala
    290                 295                 300

Met Asn Thr Thr Lys Leu Ala Asn Gly Ile Ser Tyr Tyr Glu Val Ile
305                 310                 315                 320

Glu Asn

<210> SEQ ID NO 14
<211> LENGTH: 330
<212> TYPE: PRT
<213> ORGANISM: Lactobacillus helveticus

<400> SEQUENCE: 14

Ala Asp Ser Ala Ile Asn Ala Asn Thr Asn Lys Tyr Asp Val Asp
1               5                   10                  15

Val Thr Pro Ser Ile Ser Ala Ile Ala Ala Val Ala Lys Ser Asp Thr
```

```
            20                  25                  30
Met Pro Ala Ile Pro Gly Ser Leu Thr Gly Ser Ile Ser Ala Ser Tyr
         35                  40                  45

Asn Gly Lys Ser Tyr Thr Ala Asn Leu Pro Lys Asp Ser Gly Asn Ala
 50                  55                  60

Thr Ile Thr Asp Ser Asn Asn Thr Val Lys Pro Ala Lys Leu Glu
 65                  70                  75                  80

Ala Asp Lys Ala Tyr Thr Val Thr Val Pro Asp Val Ser Phe Asn Phe
                 85                  90                  95

Gly Ser Glu Asn Ala Gly Lys Val Ile Thr Ile Gly Ser Ala Asn Pro
            100                 105                 110

Asn Val Thr Phe Thr Lys Lys Thr Gly Asp Gln Pro Ala Ser Thr Val
            115                 120                 125

Lys Val Thr Leu Asp Gln Asp Gly Val Ala Lys Leu Ser Ser Val Gln
            130                 135                 140

Ile Lys Asn Val Tyr Ala Ile Asp Thr Tyr Asn Ser Asn Val Asn
145                 150                 155                 160

Phe Tyr Asp Val Thr Thr Gly Ala Ile Val Thr Thr Gly Ala Val Ser
                165                 170                 175

Ile Asp Ala Asp Asn Gln Gly Gln Leu Asn Ile Thr Ser Val Val Ala
            180                 185                 190

Ala Ile Asn Ser Lys Tyr Phe Ala Ala Gln Tyr Asp Lys Lys Gln Leu
            195                 200                 205

Thr Asn Asp Val Thr Phe Asp Thr Glu Thr Ala Val Lys Asp Ala Leu
            210                 215                 220

Lys Ala Gln Lys Ile Glu Val Ser Ser Val Gly Tyr Phe Lys Ala Pro
225                 230                 235                 240

His Thr Phe Thr Val Asn Val Lys Ala Thr Ser Asn Lys Asn Gly Lys
                245                 250                 255

Ser Ala Thr Leu Pro Val Thr Val Thr Val Pro Asn Val Ala Asp Pro
            260                 265                 270

Val Val Pro Ser Gln Ser Lys Thr Ile Met His Asn Ala Tyr Phe Tyr
            275                 280                 285

Asp Lys Asp Ala Lys Arg Val Gly Thr Asp Lys Val Thr Arg Tyr Asn
            290                 295                 300

Thr Val Thr Val Ala Met Asn Thr Thr Lys Leu Ala Asn Gly Ile Ser
305                 310                 315                 320

Tyr Tyr Glu Val Ile Glu Asn Gly Lys Ala
                325                 330

<210> SEQ ID NO 15
<211> LENGTH: 475
<212> TYPE: PRT
<213> ORGANISM: Lactobacillus helveticus

<400> SEQUENCE: 15

Met Asp His Val Ser Lys Gly Phe Val His Tyr Arg Leu Leu Ser His
 1               5                  10                  15

Ala Glu Pro Met Ala Tyr Tyr Ile Phe Tyr Ile Ser Arg Arg Lys Asp
                20                  25                  30

His Met Lys Lys Asn Leu Arg Ile Val Ser Ala Ala Ala Ala Leu
             35                  40                  45

Leu Ala Val Ala Pro Val Ala Ala Thr Ala Met Pro Val Asn Ala Ala
 50                  55                  60
```

```
Thr Thr Ile Asn Ala Asp Ser Ala Ile Asn Ala Asn Thr Asn Ala Lys
 65                  70                  75                  80

Tyr Asp Val Asp Val Thr Pro Ser Ile Ser Ala Ile Ala Lys Val Thr
                 85                  90                  95

Gly Ser Ala Thr Ile Pro Gly Ser Leu Thr Gly Ser Ile Ser Ala Ser
            100                 105                 110

Tyr Asn Gly Lys Ser Tyr Thr Ala Asn Leu Pro Lys Asp Ser Gly Asn
        115                 120                 125

Ala Thr Ile Ala Asp Lys His Gly Asn Pro Val Lys Pro Ala Asp Leu
    130                 135                 140

Glu Ala Asp Lys Ala Tyr Thr Val Thr Val Pro Asp Val Ser Phe Asn
145                 150                 155                 160

Phe Gly Ser Glu Asn Ala Gly Lys Glu Ile Thr Ile Gly Ser Ala Asn
                165                 170                 175

Gln Asn Val Thr Phe Thr Thr Lys Asp Ser Gln Ser Gly Ser Thr Val
            180                 185                 190

Ser Gly Ser Thr Val Lys Val Thr Leu Asp Gln Asp Gly Val Ala Lys
        195                 200                 205

Leu Ser Ser Val Gln Ile Lys Asp Val Tyr Ala Ile Asp Thr Thr Tyr
210                 215                 220

Asn Ser Asn Val Asn Phe Tyr Asp Val Thr Thr Gly Ala Ile Val Thr
225                 230                 235                 240

Thr Gly Ala Val Ser Ile Asp Ala Asp Asn Gln Gly Gln Leu Asn Thr
                245                 250                 255

Ala Ser Val Val Ala Ile Ser Ser Lys Tyr Phe Ala Gln Tyr
            260                 265                 270

Ala Asp Lys Asn Leu Thr Ser Asp Asn Val Tyr Asn Ile Glu Thr
        275                 280                 285

Ala Val Lys Asp Ala Leu Lys Ala Gln Lys Ile Glu Val Ser Ser Val
    290                 295                 300

Gly Tyr Phe Lys Ala Pro His Thr Phe Thr Val Asn Val Lys Ala Thr
305                 310                 315                 320

Ser Asn Lys Asn Gly Lys Ser Ala Thr Leu Pro Val Thr Val Thr Val
                325                 330                 335

Pro Asn Val Ala Asp Pro Val Val Pro Ser Gln Ser Lys Thr Ile Met
            340                 345                 350

His Asn Ala Tyr Phe Tyr Asp Lys Asp Ala Lys Arg Val Gly Thr Asp
        355                 360                 365

Lys Val Thr Arg Tyr Asn Thr Val Thr Val Ala Met Asn Thr Thr Lys
    370                 375                 380

Leu Ala Asn Gly Ile Ser Tyr Tyr Glu Val Ile Glu Asn Gly Lys Ala
385                 390                 395                 400

Thr Gly Lys Tyr Ile Asn Ala Asp Asn Ile Asp Gly Thr Lys Arg Thr
                405                 410                 415

Leu Lys His Asn Ala Tyr Val Tyr Lys Thr Ser Lys Lys Arg Ala Asn
            420                 425                 430

Lys Val Val Leu Lys Lys Gly Thr Glu Val Thr Thr Tyr Gly Gly Ser
        435                 440                 445

Tyr Lys Phe Lys Asn Gly Lys Lys Tyr Tyr Lys Ile Gly Ala Asp Thr
    450                 455                 460

Lys Lys Thr Tyr Val Arg Val Glu Asn Phe Asp
465                 470                 475
```

```
<210> SEQ ID NO 16
<211> LENGTH: 30
<212> TYPE: PRT
<213> ORGANISM: Artificial Sequence
<220> FEATURE:
<223> OTHER INFORMATION: Signal Peptide of Recombinant SlpA of SEQ ID
      NO: 5

<400> SEQUENCE: 16

Met Gln Ser Ser Leu Lys Lys Ser Leu Tyr Leu Gly Leu Ala Ala Leu
1               5                   10                  15

Ser Phe Ala Gly Val Ala Ala Val Ser Thr Thr Ala Ser Ala
            20                  25                  30

<210> SEQ ID NO 17
<211> LENGTH: 417
<212> TYPE: PRT
<213> ORGANISM: Artificial Sequence
<220> FEATURE:
<223> OTHER INFORMATION: Mature Protein of Recombinant SlpA of SEQ ID
      NO: 5

<400> SEQUENCE: 17

Lys Ser Arg Met Ala Thr Thr Ile Asn Ala Ser Ser Ser Ala Ile Asn
1               5                   10                  15

Thr Asn Thr Asn Ala Lys Tyr Asp Val Asp Val Thr Pro Ser Val Ser
            20                  25                  30

Ala Val Ala Ala Asn Thr Ala Asn Thr Pro Ala Ile Ala Gly Asn
        35                  40                  45

Leu Thr Gly Thr Ile Ser Ala Ser Tyr Asn Gly Lys Thr Tyr Thr Ala
50                  55                  60

Asn Leu Lys Ala Asp Thr Glu Asn Ala Thr Ile Thr Ala Ala Gly Ser
65                  70                  75                  80

Thr Thr Ala Val Lys Pro Ala Glu Leu Ala Ala Gly Val Ala Tyr Thr
                85                  90                  95

Val Thr Val Asn Asp Val Ser Phe Asn Phe Gly Ser Glu Asn Ala Gly
            100                 105                 110

Lys Thr Val Thr Leu Gly Ser Ala Asn Ser Asn Val Lys Phe Thr Gly
        115                 120                 125

Thr Asn Ser Asp Asn Gln Thr Glu Thr Asn Val Ser Thr Leu Lys Val
130                 135                 140

Lys Leu Asp Gln Asn Gly Val Ala Ser Leu Thr Asn Val Ser Ile Ala
145                 150                 155                 160

Asn Val Tyr Ala Ile Asn Thr Thr Asp Asn Ser Asn Val Asn Phe Tyr
                165                 170                 175

Asp Val Thr Ser Gly Ala Thr Val Thr Asn Gly Ala Val Ser Val Asn
            180                 185                 190

Ala Asp Asn Gln Gly Gln Val Asn Val Ala Asn Val Val Ala Ala Ile
        195                 200                 205

Asn Ser Lys Tyr Phe Ala Ala Gln Tyr Ala Asp Lys Lys Leu Asn Thr
210                 215                 220

Arg Thr Ala Asn Thr Glu Asp Ala Ile Lys Ala Ala Leu Lys Asp Gln
225                 230                 235                 240

Lys Ile Asp Val Asn Ser Val Gly Tyr Phe Lys Ala Pro His Thr Phe
                245                 250                 255

Thr Val Asn Val Lys Ala Thr Ser Asn Thr Asn Gly Lys Ser Ala Thr
            260                 265                 270

Leu Pro Val Val Val Thr Val Pro Asn Val Ala Glu Pro Thr Val Ala
```

275                 280                 285
Ser Val Ser Lys Arg Ile Met His Asn Ala Tyr Tyr Tyr Asp Lys Asp
    290                 295                 300

Ala Lys Arg Val Gly Thr Asp Ser Val Lys Arg Tyr Asn Ser Val Ser
305                 310                 315                 320

Val Leu Pro Asn Thr Thr Thr Ile Asn Gly Lys Thr Tyr Tyr Gln Val
                    325                 330                 335

Val Glu Asn Gly Lys Ala Val Asp Lys Tyr Ile Asn Ala Ala Asn Ile
                340                 345                 350

Asp Gly Thr Lys Arg Thr Leu Lys His Asn Ala Tyr Val Tyr Ala Ser
                355                 360                 365

Ser Lys Lys Arg Ala Asn Lys Val Val Leu Lys Lys Gly Glu Val Val
    370                 375                 380

Thr Thr Tyr Gly Ala Ser Tyr Thr Phe Lys Asn Gly Gln Lys Tyr Tyr
385                 390                 395                 400

Lys Ile Gly Asp Asn Thr Asp Lys Thr Tyr Val Lys Val Ala Asn Phe
                    405                 410                 415

Arg

<210> SEQ ID NO 18
<211> LENGTH: 20
<212> TYPE: DNA
<213> ORGANISM: Artificial Sequence
<220> FEATURE:
<223> OTHER INFORMATION: Forward primer

<400> SEQUENCE: 18
aatgcaacca taactgccgc                                                   20

<210> SEQ ID NO 19
<211> LENGTH: 20
<212> TYPE: DNA
<213> ORGANISM: Artificial Sequence
<220> FEATURE:
<223> OTHER INFORMATION: Reverse primer

<400> SEQUENCE: 19
tgttgcgcct gaggtaacat                                                   20

<210> SEQ ID NO 20
<211> LENGTH: 21
<212> TYPE: DNA
<213> ORGANISM: Artificial Sequence
<220> FEATURE:
<223> OTHER INFORMATION: Forward primer

<400> SEQUENCE: 20
ccagctattg ccggtaacct t                                                 21

<210> SEQ ID NO 21
<211> LENGTH: 20
<212> TYPE: DNA
<213> ORGANISM: Artificial Sequence
<220> FEATURE:
<223> OTHER INFORMATION: Reverse primer

<400> SEQUENCE: 21
aacggcagta gtgctaccag                                                   20